United States Patent
Jaganathan et al.

(10) Patent No.: US 11,397,889 B2
(45) Date of Patent: *Jul. 26, 2022

(54) ABERRANT SPLICING DETECTION USING CONVOLUTIONAL NEURAL NETWORKS (CNNS)

(71) Applicant: Illumina, Inc., San Diego, CA (US)

(72) Inventors: Kishore Jaganathan, San Francisco, CA (US); Kai-How Farh, San Mateo, CA (US); Sofia Kyriazopoulou Panagiotopoulou, Redwood City, CA (US); Jeremy Francis McRae, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 755 days.

This patent is subject to a terminal disclaimer.

(21) Appl. No.: 16/160,984

(22) Filed: Oct. 15, 2018

(65) Prior Publication Data

US 2019/0197401 A1 Jun. 27, 2019

Related U.S. Application Data

(60) Provisional application No. 62/573,125, filed on Oct. 16, 2017, provisional application No. 62/573,131, (Continued)

(51) Int. Cl.
*G06N 3/08* (2006.01)
*G06K 9/62* (2022.01)
(Continued)

(52) U.S. Cl.
CPC ............. *G06N 3/08* (2013.01); *G06K 9/6267* (2013.01); *G06N 3/04* (2013.01); *G06N 3/0472* (2013.01);
(Continued)

(58) Field of Classification Search
CPC .......... G06N 3/08; G06N 3/04; G06N 3/0472; G06N 3/0481; G06N 3/084; G16B 40/00; G06K 9/6267
See application file for complete search history.

(56) References Cited

U.S. PATENT DOCUMENTS 10,423,861 B2   9/2019  Gao et al.
2017/0356976 A1  12/2017  Shapiro et al.
(Continued)

FOREIGN PATENT DOCUMENTS

CA      2894317 A1    12/2016
JP    2008027244 A     2/2008
(Continued)

OTHER PUBLICATIONS

Chen et al., "DeepLab: Semantic Image Segmentation with Deep Convolutional Nets, Atrous Convolution, and Fully Connected CRFs", Date of publication Apr. 26, 2017, pp. 834-848. (Year: 2017).*

(Continued)

*Primary Examiner* — Ying Yu Chen
(74) *Attorney, Agent, or Firm* — Haynes Beffel & Wolfeld, LLP; Ernest J. Beffel, Jr.

(57) ABSTRACT

The technology disclosed relates to constructing a convolutional neural network-based classifier for variant classification. In particular, it relates to training a convolutional neural network-based classifier on training data using a backpropagation-based gradient update technique that progressively match outputs of the convolutional network network-based classifier with corresponding ground truth labels. The convolutional neural network-based classifier comprises groups of residual blocks, each group of residual blocks is parameterized by a number of convolution filters in the residual blocks, a convolution window size of the residual blocks, and an atrous convolution rate of the (Continued)

residual blocks, the size of convolution window varies between groups of residual blocks, the atrous convolution rate varies between groups of residual blocks. The training data includes benign training examples and pathogenic training examples of translated sequence pairs generated from benign variants and pathogenic variants.

20 Claims, 37 Drawing Sheets
(2 of 37 Drawing Sheet(s) Filed in Color)

Related U.S. Application Data filed on Oct. 16, 2017, provisional application No. 62/573,135, filed on Oct. 16, 2017, provisional application No. 62/726,158, filed on Aug. 31, 2018.

(51) Int. Cl.
| | | |
|---|---|---|
| *G16B 20/00* | (2019.01) | |
| *G16B 40/00* | (2019.01) | |
| *G16B 50/00* | (2019.01) | |
| *G16B 40/20* | (2019.01) | |
| *G16B 30/00* | (2019.01) | |
| *G06N 3/04* | (2006.01) | |

(52) U.S. Cl.
CPC ........... *G06N 3/0481* (2013.01); *G06N 3/084* (2013.01); *G16B 20/00* (2019.02); *G16B 30/00* (2019.02); *G16B 40/00* (2019.02); *G16B 40/20* (2019.02); *G16B 50/00* (2019.02)

(56) References Cited

U.S. PATENT DOCUMENTS

| | | | |
|---|---|---|---|
| 2018/0075343 A1 | 3/2018 | van den Oord et al. | |
| 2018/0107927 A1 | 4/2018 | Frey | |
| 2020/0143205 A1* | 5/2020 | Yao | G06K 9/6262 |

FOREIGN PATENT DOCUMENTS

| | | |
|---|---|---|
| RU | 2371735 C2 | 10/2009 |
| WO | 2005050160 A2 | 6/2005 |
| WO | 2016145516 A1 | 9/2016 |
| WO | 2016201564 A1 | 12/2016 |

OTHER PUBLICATIONS

Lanchantin et al., "Deep Motif Dashboard: Visualizing and Understanding Genomic Sequences Using Deep Neural Networks", Oct. 18, 2016, arXiv:1608.03644v4, pp. 1-11. (Year: 2016).*
Jimenez et al., "DeepSite: protein-binding site predictor using 3D-convolutional neural networks", May 31, 2017, Bioinformatics, 33(19), 2017, pp. 3036-3042. (Year: 2017).*
Lee et al., "DNA-Level Splice Junction Prediction using Deep Recurrent Neural Networks", Dec. 16, 2015, arXiv:1512.05135v1, pp. 1-6. (Year: 2015).*
He-etal_Deep Residual Learning for Image Recognition_Dec. 10, 2015_12pgs.
Huang-etal_Densely Connected Convolutional Networks_Aug. 27, 2017_9pgs.
Leung-etal_Deep-learning-of-the-tissue-regulated-splicing-code_ 2014_9pgs.
Leung-etal_Inference-of-the-Human-Polyadenylation-Code-Apr. 27, 2017_13pgs.
Leung-etal_Machine-Learning-in-Genomic-Medicine_Jan. 1, 2016_ 22pgs.
Park-etal_Deep-Learning-for-Regulatory-Genomics_Aug. 2015_ 2pgs.
Piqueras Autoregressive model based on a deep CNN for audio generation, Mar. 2017, 58pgs.
Srivastava-etal_Highway Networks_Nov. 3, 2015_6pgs.
Szegedy-etal_Going deeper with convolutions_Sep. 17, 2014_ 12pgs.
Van den Oord et al., WaveNet: A Generative Model for Raw Audio, Sep. 19, 2016, 15 pages.
Wolterink-etal_Dilated Convolutional Neural Networks for Cardiovascular MR Segmentation_Apr. 12, 2017_9pgs.
Wu "Intro to CNN", May 1, 2017, 31pgs.
Xiong-etal_The-human-splicing-code-reveals-new-insights-into-the-genetic-determinants-of-disease_Jan. 9, 2015_20pgs.
Yue-etal_Deep-Learning-for-Genomics:A-Concise-Overview_from-internet-May 8, 2018_40pgs.
Yuen-etal_Genome-wide-characteristics-of-de-novo-mutations-in-autism_Jun. 13, 2016_10pgs.
Yu-etal_Multi-Scale Context Aggregation by Dilated Convolutions_ Apr. 30, 2016_13pgs.
XIONG-etal_The-human-splicing-code-reveals-new-insights-into-the-genetic-determinants-of-disease_Dec. 18, 2014_10pgs.
Jian-etal_In-silico-prediction-of-splice-altering-single-nucleotide-variants-in-the-human-genome_Nov. 21, 2014_11pages.
Houdayer-etal_Guidelines-for-splicing-analysis-in-molecular-diagnosis-derived-BRCA1-BRCA2-variants_Apr. 12, 2012_12pages.
Zhang-etal_DeepSplice-Deep-Classification-of-Novel-Splice-Junctions-Revealed-by-RNA-seq_Dec. 1, 2016_4pages.
PCT/US2018/055919—International Search Report and Written Opinion dated Feb. 11, 2019, 15 pages.
PCT/US2018/055915—International Search Report and Written Opinion dated Feb. 11, 2019, 14 pages.
PCT/US2018/055923—International Search Report and Written Opinion dated Feb. 11, 2019, 19 pages.
Hebsgaard, et al., "Splice site prediction in *Arabidopsis thaliana* pre mRNA by combining local and global sequence", Jan. 1, 1996, 14 pages.
Sonnenburg, et.al., "New Methods for Splice Site Recognition", 2002, 7pages.
Reed, R., and Maniatis, T. (1988). The role of the mammalian branchpoint sequence in pre-mRNA splicing. Genes Dev. 2, 1268-1276.
Reese, M.G., Eeckman, F.H., Kulp, D., and Haussler, D. (1997). Improved splice site detection in Genie. J. Comput. Biol. 4, 42 pages.
Robinson, E.B., Samocha, K.E., Kosmicki, J.A., McGrath, L., Neale, B.M., Perlis, R.H., and Daly, M.J. (2014). Autism spectrum disorder severity reflects the average contribution of de novo and familial influences. Proc. Natl. Acad. Sci. U. S. A. 111, 15161-15165.
Samocha, K.E., Robinson, E.B., Sanders, S.J., Stevens, C., Sabo, A., Mcgrath, L.M., Kosmicki, J.A., Rehnström, K., Mallick, S., Kirby, A., et al. (2014). A framework for the interpretation of de novo variation in human disease. Nat. Genet. 46, 19 pages.
Sanders, S.J., He, X., Willsey, A.J., Ercan-Sencicek, A.G., Samocha, K.E., Cicek, A.E., Murtha, M.T., Bal, V.H., Bishop, S.L., Dong, S., et al. (2015). Insights into Autism Spectrum Disorder Genomic Architecture and Biology from 71 Risk Loci. Neuron 87, 38 pages.
Sanders, S.J., Murtha, M.T., Gupta, A.R., Murdoch, J.D., Raubeson, M.J., Willsey, A.J., Ercan-Sencicek, A.G., DiLullo, N.M., Parikshak, N.N., Stein, J.L., et al. (2012). De novo mutations revealed by whole-exome sequencing are strongly associated with autism. Nature 485, 237-241.
Sanz, D.J., Acedo, A., Infante, M., Durán, M., Pérez-Cabornero, L., Esteban-Cardeñosa, E., Lastra, E., Pagani, F., Miner, C., and Velasco, E.A. (2010). A high proportion of DNA variants of BRCA1 and BRCA2 is associated with aberrant splicing in breast/ovarian cancer patients. Clin. Cancer Res. 16, 1957-1967.
Schwartz, S., Meshorer, E., and Ast, G. (2009). Chromatin organization marks exon-intron structure. Nat. Struct. Mol. Biol. 16, 7 pages.
Scotti, M.M., and Swanson, M.S. (2016). RNA mis-splicing in disease. Nat. Rev. Genet. 17, 19-32.

(56) References Cited

OTHER PUBLICATIONS

Su et al., A comprehensive assessment of RNA-seq accuracy, reproducibility and information content by the Sequencing Quality Control Consortium. Nat. Biotechnol, 2014, 32, 36 pages.
Shirai, C.L., Ley, J.N., White, B.S., Kim, S., Tibbitts, J., Shao, J., Ndonwi, M., Wadugu, B., Duncavage, E.J., Okeyo-Owuor, T., et al. (2015). Mutant U2AF1 Expression Alters Hematopoiesis and Pre-mRNA Splicing In Vivo. Cancer Cell 27, 631-643.
Shukla, S., Kavak, E., Gregory, M., Imashimizu, M., Shutinoski, B., Kashlev, M., Oberdoerffer, P., Sandberg, R., and Oberdoerffer, S. (2011). CTCF-promoted RNA polymerase II pausing links DNA methylation to splicing. Nature 479, 74-79.
Soemedi, R., Cygan, K.J., Rhine, C.L., Wang, J., Bulacan, C., Yang, J., Bayrak-Toydemir, P., McDonald, J., and Fairbrother, W.G. (2017) Pathogenic variants that alter protein code often disrupt splicing Nat. Genet. 49, 848-855.
Spies, N., Nielsen, C.B., Padgett, R.A., and Burge, C.B. (2009). Biased chromatin signatures around polyadenylation sites and exons. Mol Cell 36, 245-254.
Stark, Z., Tan, T.Y., Chong, B., Brett, G.R., Yap, P., Walsh, M., Yeung, A., Peters, H., Mordaunt, D., Cowie, S., et al. (2016). A prospective evaluation of whole-exome sequencing as a first-tier molecular test in infants with suspected monogenic disorders. Genet. Med. 18, 9 pages.
Supek, F., Miñana, B., Valcárcel, J., Gabaldón, T., and Lehner, B. (2014). Synonymous mutations frequently act as driver mutations in human cancers. Cell 156, 1324-1335.
Tennessen, J.A., Bigham, A.W., O'Connor, T.D., Fu, W., Kenny, E.E., Gravel, S., McGee, S., Do, R., Liu, X., Jun, G., et al. (2012). Evolution and Functional Impact of Rare Coding Variation from Deep Sequencing of Human Exomes. Science (80-.). 337, 64-69.
Welter, D., MacArthur, J., Morales, J., Burdett, T., Hall, P., Junkins, H., Klemm, A., Flicek, P., Manolio, T., et al. (2015). The Genotype-Tissue Expression (GTEx) pilot analysis: multitissue gene regulation in humans. Science (80-.). 348, 648-660.
Tilgner, H., Knowles, D.G., Johnson, R., Davis, C.A., Chakrabortty, S., Djebali, S., Curado, J., Snyder, M., Gingeras, T.R., and Guigó, R. (2012). Deep sequencing of subcellular RNA fractions shows splicing to be predominantly co-transcriptional in the human genome but inefficient for lncRNAs. Genome Res. 22, 1616-1625.
Tilgner, H., Nikolaou, C., Althammer, S., Sammeth, M., Beato, M., Valcárcel, J., and Guigó, R. (2009). Nucleosome positioning as a determinant of exon recognition Nat. Struct. Mol. Biol. 16, 996-1001.
Trujillano, D., Bertoli-Avella, A.M., Kumar Kandaswamy, K., Weiss, M.E., Köster, J., Marais, A., Paknia, O., Schröder, R., Garcia-Aznar, J.M., Werber, M., et al. (2017). Clinical exome sequencing: Results from 2819 samples reflecting 1000 families. Eur. J. Hum. Genet. 25, 176-182.
Turner, T.N., Hormozdiari, F., Duyzend, M.H., McClymont, S.A., Hook, P.W., Iossifov, I., Raja, A., Baker, C., Hoekzema, K., Stessman, H.A., et al. (2016). Genome Sequencing of Autism-Affected Families Reveals Disruption of Putative Noncoding Regulatory DNA. Am. J. Hum. Genet. 98, 58-74.
Ule, J., Jensen, K.B., Ruggiu, M., Mele, A., Ule, A., and Darnell, R.B. (2003). CLIP Identifies Nova-Regulated RNA Networks in the Brain. Science (80-. ). 302, 1212-1215.
Veloso, A., Kirkconnell, K.S., Magnuson, B., Biewen, B., Paulsen, M.T., Wilson, T.E., and Ljungman, M. (2014). Rate of elongation by RNA polymerase II is associated with specific gene features and epigenetic modifications. Genome Res. 24, 896-905.
Wang, E.T., Sandberg, R., Luo, S., Khrebtukova, I., Zhang, L., Mayr, C., Kingsmore, S.F., Schroth, G.P., and Burge, C.B. (2008). Alternative isoform regulation in human tissue transcriptomes. Nature 456, 470-476.
Wang, G.-S., and Cooper, T.A. (2007). Splicing in disease: disruption of the splicing code and the decoding machinery. Nat. Rev. Genet. 8, 749-761.

Wang, Z., and Burge, C.B. (2008). Splicing regulation: from a parts list of regulatory elements to an integrated splicing code. RNA 14, 802-813.
Wang, Z., Rolish, M.E., Yeo, G., Tung, V., Mawson, M., and Burge, C.B. (2004). Systematic identification and analysis of exonic splicing silencers. Cell 119, 831-845.
Wu, J., Anczukow, O., Krainer, A.R., Zhang, M.Q., and Zhang, C. (2013). OLego: Fast and sensitive mapping of spliced mRNA-Seq reads using small seeds Nucleic Acids Res. 41, 5149-5163.
Farh, K.K.H., Marson, A., Zhu, J., Kleinewietfeld, M., Housley, W.J., Beik, S., Shoresh, N., Whitton, H., Ryan, R.J.H., Shishkin, A.A., et al. (2015). Genetic and epigenetic fine mapping of causal autoimmune disease variants. Nature 518, 337-343.
Gelfman, S., Burstein, D., Penn, O., Savchenko, A., Amit, M., Schwartz, S., Pupko, T., and Ast, G. (2012). Changes in exon-intron structure during vertebrate evolution affect the splicing pattern of exons. Genome Res. 22, 35-50.
Jha, A., Gazzara, M.R., and Barash, Y. (2017). Integrative deep models for alternative splicing. 274-282.
Kingma, D.P., and Ba, J.L. (2015). Adam: A Method for Stochastic Optimization. Int. Conf. Learn. Represent, pp. 1-11.
Licatalosi, D.D., and Darnell, R.B. (2006). Splicing Regulation in Neurologic Disease. Neuron 52, 93-101.
McLaren, W., Gil, L., Hunt, S.E., Riat, H.S., Ritchie, G.R.S., Thormann, A., Flicek, P., and Cunningham, F. (2016). The Ensembl Variant Effect Predictor. Genome Biol. 17, 122, 14 pages.
Shrikumar, A., Greenside, P., and Kundaje, A. (2017). Learning Important Features Through Propagating Activation Differences. Proc. Mach. Learn. Res. 70, 9 pages.
Tan, T.Y., Dillon, O.J., Stark, Z., Schofield, D., Alam, K., Shrestha, R., Chong, B., Phelan, D., Brett, G.R., Creed, E., et al. (2017). Diagnostic impact and cost-effectiveness of whole-exome sequencing for ambulant children with suspected monogenic conditions. JAMA Pediatr. 171, 855-862.
Yang, et al., "Molecular Findings Among Patients Referred for Clinical Whole-Exome Sequencing", Nov. 12, 2014, JAMA 312, 1870-1879.
Yeo, G., and Burge, C.B. (2004). Maximum Entropy Modeling of Short Sequence Motifs with Applications to RNA Splicing Signals. J. Comput. Biol. 11, 377-394.
Yoshida, K., Sanada, M., Shiraishi, Y., Nowak, D., Nagata, Y., Yamamoto, R., Sato, Y., Sato-Otsubo, A., Kon, A., Nagasaki, M., et al. (2011). Frequent pathway mutations of splicing machinery in myelodysplasia. Nature 478, 64-69.
Zhou, J., and Troyanskaya, O.G. (2015). Predicting effects of noncoding variants with deep learning-based sequence model. Nat. Methods 12, 931-934.
Libbrecht, et. al., "Machine learning in genetics and genomics", Jan. 2, 2017, 30pgs.
Alipanahi-etal_Predicting-the-Sequence-Specificities-of-DNA-and-RNA-Binding-Proteins-by-Deep-Learning_Aug. 2015_9pgs.
Angermueller-etal_Accurate-Prediction-Of-Single-Cell-DNA-Methylation-States-Using-Deep-Learning_33pgs.
Angermueller-etal_Deep-Learning-for-Computational-Biology_2016_16pgs.
Arik-etal_Deep Voice: Real-time Neural Text-to-Speech_Mar. 7, 2017_17pgs.
Ching-etal_Opportunities-and-Obstacles-for-Deep-Learning-in-Biology-and-Medicine_Jan. 19, 2018_123pgs.
Ching-etal_Opportunities-and-Obstacles-for-Deep-Learning-in-Biology-and-Medicine_May 26, 2017_47pgs.
Goodfellow-etal_Deep Learing—Chapter 9—Convolutional Networks_2016_41 pgs.
Gu-etal_Recent Advances in Convolutional Neural Networks_Jan. 5, 2017_37pgs.
Amit, M., Donyo, M., Hollander, D., Goren, A., Kim, E., Gelfman, S., Lev-Maor, G., Burstein, D., Schwartz, S., Postolsky, B., et al. (2012). Differential GC Content between Exons and Introns Establishes Distinct Strategies of Splice-Site Recognition. Cell Rep. 1, 543-556.

(56) References Cited

OTHER PUBLICATIONS

Andersson, R., Enroth, S., Rada-Iglesias, A., Wadelius, C., and Komorowski, J. (2009). Nucleosomes are well positioned in exons and carry characteristic histone modifications. Genome Res. 19, 1732-1741.
Azad, A., Rajwa, B., and Pothen, A. (2016). flowVS: channel-specific variance stabilization in flow cytometry. BMC Bioinformatics 17, 291.
Barash, Y., Calarco, J.A., Gao, W., Pan, Q., Wang, X., Shai, O., Blencowe, B.J., and Frey, B.J. (2010). Deciphering the splicing code. Nature 465, 53-59.
Berget, S.M. (1995). Exon recognition in vertebrate splicing. J. Biol. Chem. 270, 2411-2414.
Blencowe, B.J. (2006). Alternative Splicing: New Insights from Global Analyses. Cell 126, 37-47.
Boerkoel, C.F., Exelbert, R., Nicastri, C., Nichols, R.C., Miller, F.W., Plotz, P.H., and Raben, N. (1995). Leaky splicing mutation in the acid maltase gene is associated with delayed onset of glycogenosis type II. Am. J. Hum. Genet. 56, 887-897.
Boyd, S., Cortes, C., Mohri, M., and Radovanovic, A. (2012). Accuracy at the Top. In Advances in Neural Processing Systems, pp. 953-961.
Close, P., East, P., Dirac-Svejstrup, A.B., Hartmann, H., Heron, M., Maslen, S., Chariot, A., Sorting, J., Skehel, M., and Svejstrup, J.Q. (2012). DBIRD complex integrates alternative mRNA splicing with RNA polymerase II transcript elongation. Nature 484, 386-389.
Cooper, T.A., Wan, L., and Dreyfuss, G. (2009). RNA and Disease. Cell 136, 777-793.
Cramer, P., Pesce, C.G., Baralle, F.E., and Kornblihtt, a R. (1997). Functional association between promoter structure and transcript alternative splicing. Proc. Natl. Acad. Sci. U. S. A. 94, 11456-11460.
Cummings, B.B., Marshall, J.L., Tukiainen, T., Lek, M., Donkervoort, S., Foley, A.R., Bolduc, V., Waddell, L.B., Sandaradura, S.A., O'Grady, G.L., et al. (2017). Improving genetic diagnosis in Mendelian disease with transcriptome sequencing. Sci. Transl. Med. 9, eaal5209.
De Rubeis, S., He, X., Goldberg, A.P., Poultney, C.S., Samocha, K., Ercument Cicek, A., Kou, Y., Liu, L., Fromer, M., Walker, S., et al. (2014). Synaptic, transcriptional and chromatin genes disrupted in autism. Nature 515, 209-215.
Dong, S., Walker, M.F., Camera, N.J., DiCola, M., Willsey, A.J., Ye, A.Y., Waqar, Z., Gonzalez, L.E., Overton, J.D., Frahm, S., et al. (2014). De novo insertions and deletions of predominantly paternal origin are associated with autism spectrum disorder. Cell Rep. 9, 16-23.
Ernst, J., Kheradpour, P., Mikkelsen, T.S., Shoresh, N., Ward, L.D., Epstein, C.B., Zhang, X., Wang, L., Issner, R., Coyne, M., et al. (2011). Mapping and analysis of chromatin state dynamics in nine human cell types. Nature 473, 43-49.
Fairbrother, et. al., "Predictive identification of exonic splicing enhancers in human genes. Science", 2002, pp. 1007-1013.
Finkel, R.S., Mercuri, E., Darras, B.T., Connolly, A.M., Kuntz, N.L., Kirschner, J., Chiriboga, C.A., Saito, K., Servais, L., Fizzano, E., et al. (2017). Nusinersen versus Sham Control in Infantile-Onset Spinal Muscular Atrophy. N. Engl. J. Med. 377, 1723-1732.
Fitzgerald, T.W., Gerety, S.S., Jones, W.D., van Kogelenberg, M., King, D.A., McRae, J., Morley, K.I., Parthiban, V., Al-Turki, S., Ambridge, K., et al. (2015). Large-scale discovery of novel genetic causes of developmental disorders. Nature 519, 223-228.
Gelfman, S., Cohen, N., Yearim, A., and Ast, G. (2013). DNA-methylation effect on cotranscriptional splicing is dependent on GC architecture of the exon-intron structure. Genome Res. 23, 789-799.
Glorot, X., and Bengio, Y. (2010). Understanding the difficulty of training deep feedforward neural networks. Proc. 13th Int. Conf. Artif. Intell. Stat. 9, 249-256.
Gouya, L., Puy, H., Robreau, A.-M., Bourgeois, M., Lamoril, J., Silva, V. Da, Grandchamp, B., and Deybach, J.-C. (2002). The penetrance of dominant erythropoietic protoporphyria is modulated by expression of wildtype FECH. Nat. Genet. 30, 27-28.

Graubert, T.A., Shen, D., Ding, L., Okeyo-Owuor, T., Lunn, C.L., Shao, J., Krysiak, K., Harris, C.C., Koboldt, D.C., Larson, D.E., et al. (2012). Recurrent mutations in the U2AF1 splicing factor in myelodysplastic syndromes. Nat. Genet. 44, 53-57.
Harrow, J., Frankish, A., Gonzalez, J.M., Tapanari, E., Diekhans, M., Kokocinski, F., Aken, B.L., Barrell, D., Zadissa, A., Searle, S., et al. (2012). GENCODE: the reference human genome annotation for The ENCODE Project. Genome Res. 22, 1760-1774.
He, K., Zhang, X., Ren, S., and Sun, J. (2016b). Identity mappings in deep residual networks. In European Conference on Computer Vision, pp. 630-645.
Herring, C.A., Banerjee, A., McKinley, E.T., Simmons, A.J., Ping, J., Roland, J.T., Franklin, J.L., Liu, Q., Gerdes, M.J., Coffey, R.J., et al. (2018). Unsupervised Trajectory Analysis of Single-Cell RNA-Seq and Imaging Data Reveals Alternative Tuft Cell Origins in the Gut. Cell Syst. 6, 37-51.e9.
Hoffman, M.M., Buske, O.J., Wang, J., Weng, Z., Bilmes, J.A., and Noble, W.S. (2012). Unsupervised pattern discovery in human chromatin structure through genomic segmentation. Nat. Methods 9, 473-476.
Ioffe-etal_Batch Normalization: Accelerating Deep Network Training_ Mar. 2, 2015_11pgs.
Iossifov, I., O'Roak, B.J., Sanders, S.J., Ronemus, M., Krumm, N., Levy, D., Stessman, H.A., Witherspoon, K.T., Vives, L., Patterson, K.E., et al. (2014). The contribution of de novo coding mutations to autism spectrum disorder. Nature 515, 216-221.
Irimia, M., Weatheritt, R.J., Ellis, J.D., Parikshak, N.N., Gonatopoulos-Pournatzis, T., Babor, M., Quesnel-Vallières, M., Tapial, J., Raj, B., O'Hanlon, D., et al. (2014). A highly conserved program of neuronal microexons is misregulated in autistic brains. Cell 159, 1511-1523.
Jonkers, I., Kwak, H., and Lis, J.T. (2014). Genome-wide dynamics of Pol II elongation and its interplay with promoter proximal pausing, chromatin, and exons Elife 3, e02407.
Jung, H., Lee, D., Lee, J., Park, D., Kim, Y.J., Park, W.-Y., Hong, D., Park, P.J., and Lee, E. (2015). Intron retention is a widespread mechanism of tumor-suppressor inactivation. Nat. Genet. 47, 1242-1248.
Kasowski, M., Kyriazopoulou-Panagiotopoulou, S., Grubert, F., Zaugg, J.B., Kundaje, A., Liu, Y., Boyle, A.P., Zhang, Q.C., Zakharia, F., Spacek, D.V., et al. (2013). Extensive variation in chromatin states across humans. Science (80-. ). 342.
Katz, Y., Wang, E.T., Airoldi, E.M., and Burge, C.B. (2010). Analysis and design of RNA sequencing experiments for identifying isoform regulation. Nat. Methods 7, 1009-1015.
Keren, H., Lev-Maor, G., and Ast, G. (2010). Alternative splicing and evolution: Diversification, exon definition and function. Nat. Rev. Genet. 11, 345-355.
Kosmicki, J.A., Samocha, K.E., Howrigan, D.P., Sanders, S.J., Slowikowski, K., Lek, M., Karczewski, K.J., Cutler, D.J., Devlin, B., Roeder, K., et al. (2017). Refining the role of de novo protein-truncating variants in neurodevelopmental disorders by using population reference samples. Nat. Genet. 49, 504-510.
Kremer, L.S., Bader, D.M., Mertes, C., Kopajtich, R., Pichler, G., Iuso, A., Haack, T.B., Graf, E., Schwarzmayr, T., Terrile, C., et al. (2017). Genetic diagnosis of Mendelian disorders via RNA sequencing. Nat. Commun. 8, 15824, pp. 1-11.
Krishnamoorthy, K., and Thomson, J. (2004). A more powerful test for comparing two Poisson means. J. Stat. Plan. Inference 119, 23-35.
Lee, H., Deignan, J.L., Dorrani, N., Strom, S.P., Kantarci, S., Quintero-Rivera, F., Das, K., Toy, T., Harry, B., Yourshaw, M., et al. (2014). Clinical Exome Sequencing for Genetic Identification of Rare Mendelian Disorders. JAMA 312, 1880-1887.
Lek, M., Karczewski, K.J., Minikel, E. V., Samocha, K.E., Banks, E., Fennell, T., O'Donnell-Luria, A.H., Ware, U.S., Hill, A.J., Cummings, B.B., et al. (2016). Analysis of protein-coding genetic variation in 60,706 humans. Nature 536, 285-291.
Li, Y.I., Knowles, D.A., Humphrey, J., Barbeira, A.N., Dickinson, S.P., Im, H.K., and Pritchard, J.K. (2018). Annotation-free quantification of RNA splicing using LeafCutter. Nat. Genet. 50, 151-158.
Li, Y.I., Sanchez-Pulido, L., Haerty, W., and Ponting, C.P. (2015). RBFOX and PTBP1 proteins regulate the alternative splicing of micro-exons in human brain transcripts. Genome Res. 25, 1-13.

(56) References Cited

OTHER PUBLICATIONS

Lonsdale, J., Thomas, J., Salvatore, M., Phillips, R., Lo, E., Shad, S., Hasz, R., Walters, G., Garcia, F., Young, N., et al. (2013) The Genotype-Tissue Expression (GTEx) project. Nat. Genet. 45, 580-585.
Luco, R.F., Allo, M., Schor, I.E., Kornblihtt, A.R., and Misteli, T. (2011). Epigenetics in Alternative Pre-mRNA Splicing. Cell 144, 16-26.
Luco, R.F., Pan, Q., Tominaga, K., Blencowe, B.J., Pereira-Smith, O.M., and Misteli, T. (2010). Regulation of alternative splicing by histone modifications. Science 327, 996-1000.
Maurano, M.T., Humbert, R., Rynes, E., Thurman, R.E., Haugen, E., Wang, H., Reynolds, A.P., Sandstrom, R., Qu, H., Brody, J., et al. (2012). Systematic Localization of Common Disease-Associated Variation in Regulatory DNA. Science (80-. ). 337, 1190-1195.
McRae, J.F., Clayton, S., Fitzgerald, T.W., Kaplanis, J., Prigmore, E., Rajan, D., Sifrim, A., Aitken, S., Akawi, N., Alvi, M., et al. (2017) Prevalence and architecture of de novo mutations in developmental disorders. Nature 542, 433-438.
Monroe, G.R., Frederix, G.W., Savelberg, S.M.C., de Vries, T.I., Duran, K.J., van der Smagt, J.J., Terhal, P.A., van Hasselt, P.M., Kroes, H.Y., Verhoeven-Duif, N.M., et al. (2016). Effectiveness of whole-exome sequencing and costs of the traditional diagnostic trajectory in children with intellectual disability. Genet. Med. 18, 949-956.
Neale, B.M., Kou, Y., Liu, L., Ma'ayan, A., Samocha, K.E., Sabo, A., Lin, C.-F., Stevens, C., Wang, L.-S., Makarov, V., et al. (2012). Patterns and rates of exonic de novo mutations in autism spectrum disorders. Nature 485, 13 pages.
Padgett, R.A. (2012). New connections between splicing and human disease. Trends Genet. 28, 14 pages.
Pertea, M., Lin, X., and Salzberg, S.L. (2001). GeneSplicer: a new computational method for splice site prediction. Nucleic Acids Res. 29, 1185-1190.
Alom, et. al. ,"The History Began from AlexNet A Comprehensive Survey on Deep Learning Approaches", 2018, 39 pages.
Louadi, et. al. ,"Deep Splicing Code Classifying Alternative Splicing Events Using Deep Learning", Aug. 1, 2019, 15 pages.
Degroeve, et. al. ,"SpliceMachine: predicting splice sites from high dimensional local context representations", Nov. 25, 2004, 7pages.
Dvinge, et. al.,"RNA splicing factors as oncoproteins and tumour suppressors", Jun. 10, 2016, 18pgs.
Gupta, et. al.,"Dilated Convolutions for Modeling Long Distance Genomic Dependencies", Oct. 3, 2017, 8 pages.
Xiong, et. al.,"Bayesian prediction of tissue regulated splicing using RNA sequence and cellular context", Jul. 29, 2011, 9 pages.
Zuallaert, et. al.,"SpliceRover: Interpretable convolutional neural networks for improved splice site prediction", Jun. 21, 2018, 9 pages.
Zuallaert, et. al.,"Supplemental_Materials_for SpliceRover: Interpretable convolutional neural networks for improved splice site prediction", Jun. 21, 2018, 11 pages.
PCT/US2018/055915—Amendment Under Article 34 dated Oct. 14, 2019, 31 pages.
PCT/US2018/055919—Amendment Under Article 34 dated Oct. 11, 2019, 36 pages.
PCT/US2018/055923—Amendment Under Article 34 dated Oct. 11, 2019, 85 pages.
PCT/US2018/055919—Amendment Under Article 34 dated Dec. 13, 2019, 25 pages.
PCT/US2018/055923—Amendment Under Article 34 dated Dec. 13, 2019, 27 pages.
PCT/US2018/055919—International Preliminary Report on Patentability dated Jan. 20, 2020, 25 pages.
Zhang et al., "DeepSplice: Deep classification of novel splice junctions revealed by RNA-seq." In 2016 IEEE International conference on bioinformatics and biomedicine (BIBM), pp. 330-333. IEEE, 2016.

Hebsgaard et al., "Splice site prediction in *Arabidopsis thaliana* pre-mRNA by combining local and global sequence information." Nucleic acids research 24, No. 17 (1996): 3439-3452.
Sonnenburg et al., "New methods for splice site recognition." In International Conference on Artificial Neural Networks, pp. 329-336. Springer, Berlin, Heidelberg, 2002.
PCT/US2018/055923—International Preliminary Report on Patentability dated Jan. 28, 2020, 29 pages.
PCT/US2018/055915—International Preliminary Report on Patentability dated Jan. 28, 2020, 26 pages.
PCT/US2018/055915—Amendment Under Article 34 dated Dec. 31, 2019, 19 pages.
PCT/US2018/055915—Amendment Under Article 34 dated Dec. 12, 2019, 33 pages.
AU 2018350905—Voluntary Amendments filed on Aug. 3, 2020, 89 pages.
JP 2019-567663—Voluntary Amendments filed May 25, 2020, 9 pages.
MX MX/a/2019/014689—Voluntary Amendments filed Jul. 7, 2020, 47 pages.
MY PI 2019007228—Voluntary Amendments filed May 4, 2020, 15 pages.
ZA 2019/08143—Voluntary Amendments filed Jul. 17, 2020, 14 pages.
AU 2018350907—Voluntary Amendments filed Apr. 28, 2020, 194 pages.
CN 2018800438296—Voluntary Amendments filed Jul. 6, 2020, 15 pages.
EP 18796346-7—Voluntary Amendments filed Jul. 27, 2020, 14 pages.
CN 2018800438671—Voluntary Amendments filed Jun. 28, 2020, 19 pages.
EP 18796347-5—Voluntary Amendments filed Jul. 27, 2020, 11 pages.
JP 2019-567670—Voluntary Amendments filed May 25, 2020, 8 pages.
MY PI 2019007228—First Office Action dated Jul. 29, 2020, 4 pages.
AU 2018350907—First Office Action dated Jun. 12, 2020, 4 pages.
AU 2018350907—First Office Action dated Jun. 12, 2020, 12 pages.
AU 2018350909—First Office Action dated Nov. 2, 2020, 9 pages.
CN 2018800430487—Voluntary Amendment filed Jul. 21, 2020, 19 pages with English translation.
CN 2018800438296—Voluntary Amendment filed Jul. 6, 2020, 15 pages with English translation.
CN 2018800438671—Voluntary Amendment Filed Jun. 28, 2020, 19 pages with English translation.
EP 18796345.9—Response to Rule 161(1) & 162 Communication dated Jan. 24, 2020, filed Aug. 3, 2020, 13 pages.
EP 18796345.9—Rule 161(1) & 162 Communication dated Jan. 24, 2020, 3 pages.
EP 18796346.7—Response to Rule 161(1) & 162 Communication dated Jan. 16, 2020, filed Jul. 27, 2020, 14 pages.
EP 18796346.7—Rule 161(1) & 162 Communication dated Jan. 16, 2020, 3 pages.
EP 18796347.5—Response to Rule 161(1) & 162 Communication dated Jan. 16, 2020, filed Jul. 27, 2020, 11 pages.
EP 18796347.5—Rule 161(1) & 162 Communication dated Jan. 16, 2020, 3 pages.
EP 18796345.9—First Office Action dated Feb. 5, 2021, 5 pages.
IL 271150 Notice before Acceptance, dated Apr. 8, 2021, 162 pages.
IL 271150 Response to First Office Action, dated Feb. 11, 2021 (OA dated Oct. 11, 2020), 190 pages.
IL 271150, First Office Action dated Oct. 11, 2020, 9 pages.
JP 2019-567663 Notice of Allowance, dated Aug. 31, 2020, 3 pages.
KR10-2019-7036420 First Office Action, dated Feb. 22, 2021, 6 pages.
KR 10-2019-7036420 Voluntary Amendment and Accelerated Examination Request, dated Nov. 3, 2020, 17 pages.
MX 2019014689 Office Action dated Oct. 16, 2020, 2 pages.
IL 271118 Notice before Acceptance, dated Feb. 14, 2021, 161 pages.

(56) References Cited

OTHER PUBLICATIONS

IL 271118 Minor Amendment made to Specification, dated Feb. 11, 2021, 186 pages.
IL 271118 Response to Notice before Allowance, dated Jan. 21, 2021, 187 pages.
IL 211178 Notice Before Allowance, dated Sep. 21, 2020, 4 pages.
JP 2019-567669 Response to First Office Action, dated Mar. 1, 2021, 13 pages.
JP 2019-567669 First Office Action, dated Aug. 31, 2020, 11 pages.
KR 10-2019-7038078 Notice of Allowance, dated Nov. 25, 2020, 4 pages.
KR 10-2019-7038078 Response to Office Action, dated Oct. 12, 2020, 14 pages.
KR 10-2019-7038078 First Office Action, dated Aug. 11, 2020, 6 pages.
SG 11201912746Q Request for Exam and Voluntary Amendments, dated Aug. 25, 2020, 50 pages.
IL 271115 Notice before Acceptance, dated Mar. 8, 2021, 184 pages.
IL 271115 Response to First Office Action, dated Mar. 1, 2021, 317 pages.
IL 271115 First Office Action, dated Nov. 1, 2020, 3 pages.
JP 2019-567670 Certificate of Grant, dated Feb. 19, 2021, 3 pages.
JP 2019-567670 Notice of Allowance, dated Jan. 18, 2021, 6 pages.
JP 2019-567670 Response to First Office Action, dated Nov. 27, 2020, 8 pages.
JP 2019-567670 First Office Action dated Aug. 31, 2020, 6 pages.
JP 2019-567670 PPH and Voluntary Amendment, dated May 25, 2020, 8 pages.
KR 10-2019-7038079 Voluntary Amendment and Accelerated Examination Filed, dated Nov. 6, 2020, 16 pages.
KR 10-2019-7038079 First Office Action, dated Mar. 8, 2021, 9 pages.
NZ 759846 First Office Action, dated May 4, 2021, 3 pages.
JP 2019-567670 Notice of Allowance, dated May 10, 2021, 3 pages.
NZ 759880 First Office Action, dated Apr. 23, 2021, 3 pages.
IL 283203 Notice Before Examination, dated May 18, 2021, 2 pages.
AU 2018350907 Response to First Office Action, dated Jun. 23, 2021, 230 pages.
AU 2018350907 Second Office Action, dated Jul. 9, 2021, 3 pages.
RU 2019139175 First Office Action, dated Jul. 27, 2021, 8 pages.
KR 10-2019-7036420 Response to First Office Action dated Feb. 22, 2021, filed Jun. 21, 2021, 14 pages.
KR 10-2019-7036420 Notice of Allowance, dated Jul. 20, 2021, 3 pages.
AU 2018350905—Second Office Action dated Aug. 27, 2021, 3 pages.
AU 2018350909—Response to First Office Action, dated Aug. 6, 2021, 34 pages.
AU 2018350907—Response to Second Office Action, filed Aug. 5, 2021, 11 pages.
AU 2018350905—Response to First Office Action, filed Oct. 26, 2021, 406 pages.
AU 2018350905—Response to Second Office Action, filed Nov. 10, 2021, 200 pages.
NZ 759880—Response to First Office Action, filed Oct. 22, 2021, 16 pages.
JP 2020-163488 Notice of Allowance, dated Oct. 20, 2021, 6 pages.
AU 2018350907 Notice of Acceptance, dated Aug. 16, 2021, 3 pages.
IL 283203 Response to Notice Before Examination dated May 18, 2021, filed Sep. 13, 2021, 5 pages.
JP 2019-567669 Notice of Allowance, dated May 10, 2021, 6 pages.
NZ 759879 First Office Action, dated Apr. 29, 2021, 3 pages.
SG 11201912746Q Response to Written Opinion, filed Jul. 23, 2021, 20 pages.
SG 11201912746Q Notice of Grant, dated Oct. 21, 2021, 6 pages.
SG 11201912746Q Written Opinion, dated Feb. 23, 2021, 6 pages.
AU 2018350909 Notice of Acceptance, dated Sep. 9, 2021, 3 pages.
KR 10-2019-7038079 Response to First Office Action dated Mar. 8, 2021, filed Sep. 8, 2021, 29 pages.
NZ 759880 Notice of Acceptance, dated Oct. 26, 2021, 1 page.
AU 2018350905 Response to Office Action, filed Nov. 17, 2021, 197 pages.
EP 18796345.9 Response to Office Action, filed Nov. 16, 2021, 12 pages.
NZ 759879 Response to Office Action, filed Nov. 19, 2021, 183 pages.
NZ 759846 Response to Office Action, filed Nov. 30, 2021, 14 pages.
IL 283203 First Office Action, dated Dec. 14, 2021, 5 pages.
Johansen et al. Splice Site Prediction Using Artifical Neural Networks, Computational Intelligence Methods for Bioinformatics and Biostatistics, 5th International Meeting, CIBB 2008, Vietri sul Mare, Italy, Oct. 3-4, 2008, pp. 102-113.
JP 2021-023537 Office Action, dated Jan. 11, 2022, 3 pages.
Xu etal., iSS-PC-Identifying Splicing Sites via Physical-Chemical Properties Using Deep Sparse Auto-Encoder_Scientific Reports_Online-Aug. 15, 2017_12pags.
Xueqiu Jian, et al_In Silico Tools for Splicing Defect Prediction, a Survey from the Viewpoint of End Users_Dec. 12, 2011_7pages.
Neelam Goel, et al._An improved method for splice site prediction in DNA sequences using support vector machines_Dec. 2015_10pages.

\* cited by examiner

Residual Block and Skip-Connections used in Convolutional Neural Networks

Batch Normalization Forward Pass with Convolutional Neural Networks

$$\mu_B = \frac{1}{n}\sum_{i=1}^{n} x_i^{(\ell-1)}$$

$$\sigma_B^2 = \frac{1}{n}\sum_{i=1}^{n} (x_i^{(\ell-1)} - \mu_B)^2$$

$$\hat{x}^{(\ell-1)} = \frac{x^{(\ell-1)} - \mu_B}{\sqrt{\sigma_B^2 + \epsilon}}$$

$$x^{(\ell)} = \gamma^{(\ell)} \hat{x}^{(\ell-1)} + \beta^{(\ell)}$$

FIG. 12

Batch Normalization – Inference with Convolutional Neural Networks $$\hat{x}^{(\ell-1)} = \frac{x^{(\ell-1)} - \mu_\mathcal{D}}{\sqrt{\sigma_\mathcal{D}^2 + \epsilon}}$$

$$x_i^{(\ell)} = \gamma^{(\ell)} \hat{x}_i^{(\ell-1)} + \beta^{(\ell)}$$

FIG. 13

Batch Normalization Backward Pass with
Convolutional Neural Networks $$\nabla_{\gamma^{(\ell)}} \mathcal{L} = \sum_{i=1}^{n} (\nabla_{x^{(\ell+1)}} \mathcal{L})_i \cdot \hat{x}_i^{(\ell)}$$

$$\nabla_{\beta^{(\ell)}} \mathcal{L} = \sum_{i=1}^{n} (\nabla_{x^{(\ell+1)}} \mathcal{L})_i$$

FIG. 14

Batch Normalization in Convolution Layers

```
conv_model.add(layers.Conv2D(32, 3, activation='relu'))
conv_model.add(layers.BatchNormalization())         <----- After a Conv layer
dense_model.add(layers.Dense(32, activation='relu'))
dense_model.add(layers.BatchNormalization())        <----- After a Dense layer
```

FIG. 15

Global Average Pooling (GAP) in Convolutional Neural Networks

Residual Block (RB) (N, W, D)

N: Number of Convolution Filters
W: Convolution Window Size
D: Atrous Convolution Rate

| | A | C | G | T | T | T | G | C | A | C | A | C | G | ? | G | T | A | T | A | T |
|---|---|---|---|---|---|---|---|---|---|---|---|---|---|---|---|---|---|---|---|---|
| A | 1 | 0 | 0 | 0 | 0 | 0 | 0 | 0 | 1 | 0 | 1 | 0 | 0 | 0 | 0 | 0 | 1 | 0 | 1 | 0 |
| C | 0 | 1 | 0 | 0 | 0 | 0 | 0 | 1 | 0 | 1 | 0 | 1 | 0 | 0 | 0 | 0 | 0 | 0 | 0 | 0 |
| G | 0 | 0 | 1 | 0 | 0 | 0 | 1 | 0 | 0 | 0 | 0 | 0 | 1 | 0 | 1 | 0 | 0 | 0 | 0 | 0 |
| T | 0 | 0 | 0 | 1 | 1 | 1 | 0 | 0 | 0 | 0 | 0 | 0 | 0 | 0 | 0 | 1 | 0 | 1 | 0 | 1 |
| N | 0 | 0 | 0 | 0 | 0 | 0 | 0 | 0 | 0 | 0 | 0 | 0 | 0 | 1 | 0 | 0 | 0 | 0 | 0 | 0 |

One-hot Encoding ←

ABERRANT SPLICING DETECTION USING CONVOLUTIONAL NEURAL NETWORKS (CNNS)

PRIORITY APPLICATIONS

This application claims priority to or the benefit of U.S. Provisional Patent Application No. 62/573,125, titled, "Deep Learning-Based Splice Site Classification," by Kishore Jaganathan, Kai-How Farh, Sofia Kyriazopoulou Panagiotopoulou and Jeremy Francis McRae, filed Oct. 16, 2017; U.S. Provisional Patent Application No. 62/573,131, titled, "Deep Learning-Based Aberrant Splicing Detection," by Kishore Jaganathan, Kai-How Farh, Sofia Kyriazopoulou Panagiotopoulou and Jeremy Francis McRae, filed Oct. 16, 2017; U.S. Provisional Patent Application No. 62/573,135, titled, "Aberrant Splicing Detection Using Convolutional Neural Networks (CNNs)," by Kishore Jaganathan, Kai-How Farh, Sofia Kyriazopoulou Panagiotopoulou and Jeremy Francis McRae, filed Oct. 16, 2017; and U.S. Provisional Patent Application No. 62/726,158, titled, "Predicting Splicing from Primary Sequence with Deep Learning," by Kishore Jaganathan, Kai-How Farh, Sofia Kyriazopoulou Panagiotopoulou and Jeremy Francis McRae, filed Aug. 31, 2018. The provisional applications are hereby incorporated by reference for all purposes.

INCORPORATIONS

The following are incorporated by reference for all purposes as if fully set forth herein:

Contemporaneously filed PCT Patent Application No. PCT/US18/55915, titled "Deep Learning-Based Splice Site Classification," by Kishore Jaganathan, Kai-How Farh, Sofia Kyriazopoulou Panagiotopoulou and Jeremy Francis McRae, filed on Oct. 15, 2018.

Contemporaneously filed PCT Patent Application No. PCT/US18/55919, titled "Deep Learning-Based Aberrant Splicing Detection," by Kishore Jaganathan, Kai-How Farh, Sofia Kyriazopoulou Panagiotopoulou and Jeremy Francis McRae, filed on Oct. 15, 2018.

Contemporaneously filed PCT Patent Application No. PCT/US18/55923, titled "Aberrant Splicing Detection Using Convolutional Neural Networks (CNNs)," by Kishore Jaganathan, Kai-How Farh, Sofia Kyriazopoulou Panagiotopoulou and Jeremy Francis McRae, filed on Oct. 15, 2018.

U.S. Nonprovisional Patent Application titled "Deep Learning-Based Splice Site Classification," by Kishore Jaganathan, Kai-How Farh, Sofia Kyriazopoulou Panagiotopoulou and Jeremy Francis McRae, filed filed contemporaneously.

U.S. Nonprovisional Patent Application titled "Deep Learning-Based Aberrant Splicing Detection," by Kishore Jaganathan, Kai-How Farh, Sofia Kyriazopoulou Panagiotopoulou and Jeremy Francis McRae, filed contemporaneously.

U.S. Nonprovisional Patent Application titled "Aberrant Splicing Detection Using Convolutional Neural Networks (CNNs)," by Kishore Jaganathan, Kai-How Farh, Sofia Kyriazopoulou Panagiotopoulou and Jeremy Francis McRae, filed contemporaneously.

Document 1—S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

Document 2—S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv: 1702.07825, 2017;

Document 3—F. Yu and V. Koltun, "MULTI-SCALE CONTEXT AGGREGATION BY DILATED CONVOLUTIONS," arXiv:1511.07122, 2016;

Document 4—K. He, X. Zhang, S. Ren, and J. Sun, "DEEP RESIDUAL LEARNING FOR IMAGE RECOGNITION," arXiv:1512.03385, 2015;

Document 5—R. K. Srivastava, K. Greff, and J. Schmidhuber, "HIGHWAY NETWORKS," arXiv: 1505.00387, 2015;

Document 6—G. Huang, Z. Liu, L. van der Maaten and K. Q. Weinberger, "DENSELY CONNECTED CONVOLUTIONAL NETWORKS," arXiv: 1608.06993, 2017;

Document 7—C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

Document 8—S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

Document 9—J. M. Wolterink, T. Leiner, M. A. Viergever, and I. Isgum, "DILATED CONVOLUTIONAL NEURAL NETWORKS FOR CARDIOVASCULAR MR SEGMENTATION IN CONGENITAL HEART DISEASE," arXiv:1704.03669, 2017;

Document 10—L. C. Piqueras, "AUTOREGRESSIVE MODEL BASED ON A DEEP CONVOLUTIONAL NEURAL NETWORK FOR AUDIO GENERATION," Tampere University of Technology, 2016;

Document 11—J. Wu, "Introduction to Convolutional Neural Networks," Nanjing University, 2017;

Document 12—I. J. Goodfellow, D. Warde-Farley, M. Mirza, A. Courville, and Y. Bengio, "CONVOLUTIONAL NETWORKS", Deep Learning, MIT Press, 2016; and Document 13—J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv:1512.07108, 2017.

Document 1 describes deep convolutional neural network architectures that use groups of residual blocks with convolution filters having same convolution window size, batch normalization layers, rectified linear unit (abbreviated ReLU) layers, dimensionality altering layers, atrous convolution layers with exponentially growing atrous convolution rates, skip connections, and a softmax classification layer to accept an input sequence and produce an output sequence that scores entries in the input sequence. The technology disclosed uses neural network components and parameters described in Document 1. In one implementation, the technology disclosed modifies the parameters of the neural network components described in Document 1. For instance, unlike in Document 1, the atrous convolution rate in the technology disclosed progresses non-exponentially from a lower residual block group to a higher residual block group. In another example, unlike in Document 1, the convolution window size in the technology disclosed varies between groups of residual blocks.

Document 2 describes details of the deep convolutional neural network architectures described in Document 1.

Document 3 describes atrous convolutions used by the technology disclosed. As used herein, atrous convolutions are also referred to as "dilated convolutions". Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

Document 4 describes residual blocks and residual connections used by the technology disclosed.

Document 5 describes skip connections used by the technology disclosed. As used herein, skip connections are also referred to as "highway networks".

Document 6 describes densely connected convolutional network architectures used by the technology disclosed.

Document 7 describes dimensionality altering convolution layers and modules-based processing pipelines used by the technology disclosed. One example of a dimensionality altering convolution is a 1×1 convolution.

Document 8 describes batch normalization layers used by the technology disclosed.

Document 9 also describes atrous/dilated convolutions used by the technology disclosed.

Document 10 describes various architectures of deep neural networks that can be used by the technology disclosed, including convolutional neural networks, deep convolutional neural networks, and deep convolutional neural networks with atrous/dilated convolutions.

Document 11 describes details of a convolutional neural network that can be used by the technology disclosed, including algorithms for training a convolutional neural network with subsampling layers (e.g., pooling) and fully-connected layers.

Document 12 describes details of various convolution operations that can be used by the technology disclosed.

Document 13 describes various architectures of convolutional neural networks that can be used by the technology disclosed.

INCORPORATION BY REFERENCE OF TABLES SUBMITTED ELECTRONICALLY WITH APPLICATION

Three table files in ASCII text format are submitted with this application and incorporated by reference. The names, creation dates and sizes of the files are:

| | | |
|---|---|---|
| table_S4_mutation_rates.txt | Aug. 31, 2018 | 2,452 KB |
| table_S5_gene_enrichment.txt | Aug. 31, 2018 | 362 KB |
| table_S6_validation.txt | Aug. 31, 2018 | 362 KB |

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep learning-based techniques for training deep convolutional neural networks.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Machine Learning

In machine learning input variables are used to predict an output variable. The input variables are often called features and are denoted by $X=(X_1, X_2, \ldots, X_k)$, where each $X_i$, $i \in 1, \ldots, k$ is a feature. The output variable is often called the response or dependent variable and is denoted by the variable $Y_i$. The relationship between Y and the corresponding X can be written in a general form:

$$Y = f(X) + \in$$

In the equation above, $f$ is a function of the features ($X_1$, $X_2, \ldots, X_k$) and $\in$ is the random error term. The error term is independent of X and has a mean value of zero.

In practice, the features X are available without having Y or knowing the exact relation between X and Y. Since the error term has a mean value of zero, the goal is to estimate $f$.

$$\hat{Y} = \hat{f} = (X)$$

In the equation above, $\hat{f}$ is the estimate of $\in$, which is often considered a black box, meaning that only the relation between the input and output of $\hat{f}$ is known, but the question why it works remains unanswered.

The function $\hat{f}$ is found using learning. Supervised learning and unsupervised learning are two ways used in machine learning for this task. In supervised learning, labeled data is used for training. By showing the inputs and the corresponding outputs (=labels), the function $\hat{f}$ is optimized such that it approximates the output. In unsupervised learning, the goal is to find a hidden structure from unlabeled data. The algorithm has no measure of accuracy on the input data, which distinguishes it from supervised learning.

Neural Networks

The single layer perceptron (SLP) is the simplest model of a neural network. It comprises one input layer and one activation function as shown in FIG. 1. The inputs are passed through the weighted graph. The function $f$ uses the sum of the inputs as argument and compares this with a threshold θ.

FIG. 2 shows one implementation of a fully connected neural network with multiple layers. A neural network is a system of interconnected artificial neurons (e.g., $a_1$, $a_2$, $a_3$) that exchange messages between each other. The illustrated neural network has three inputs, two neurons in the hidden layer and two neurons in the output layer. The hidden layer has an activation function $f(\bullet)$ and the output layer has an activation function $g(\bullet)$. The connections have numeric weights (e.g., $w_{11}$, $w_{21}$, $w_{12}$, $w_{31}$, $w_{22}$, $w_{32}$, $v_{11}$, $v_{22}$) that are tuned during the training process, so that a properly trained network responds correctly when fed an image to recognize. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab. In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 12 shows the batch normalization forward pass.

FIG. 13 illustrates the batch normalization transform at test time.

FIG. 14 shows the batch normalization backward pass.

FIG. 15 depicts use of a batch normalization layer with convolutional or densely connected layer.

FIG. 29 illustrates a one-hot encoder.

DETAILED DESCRIPTION

Figure 1:
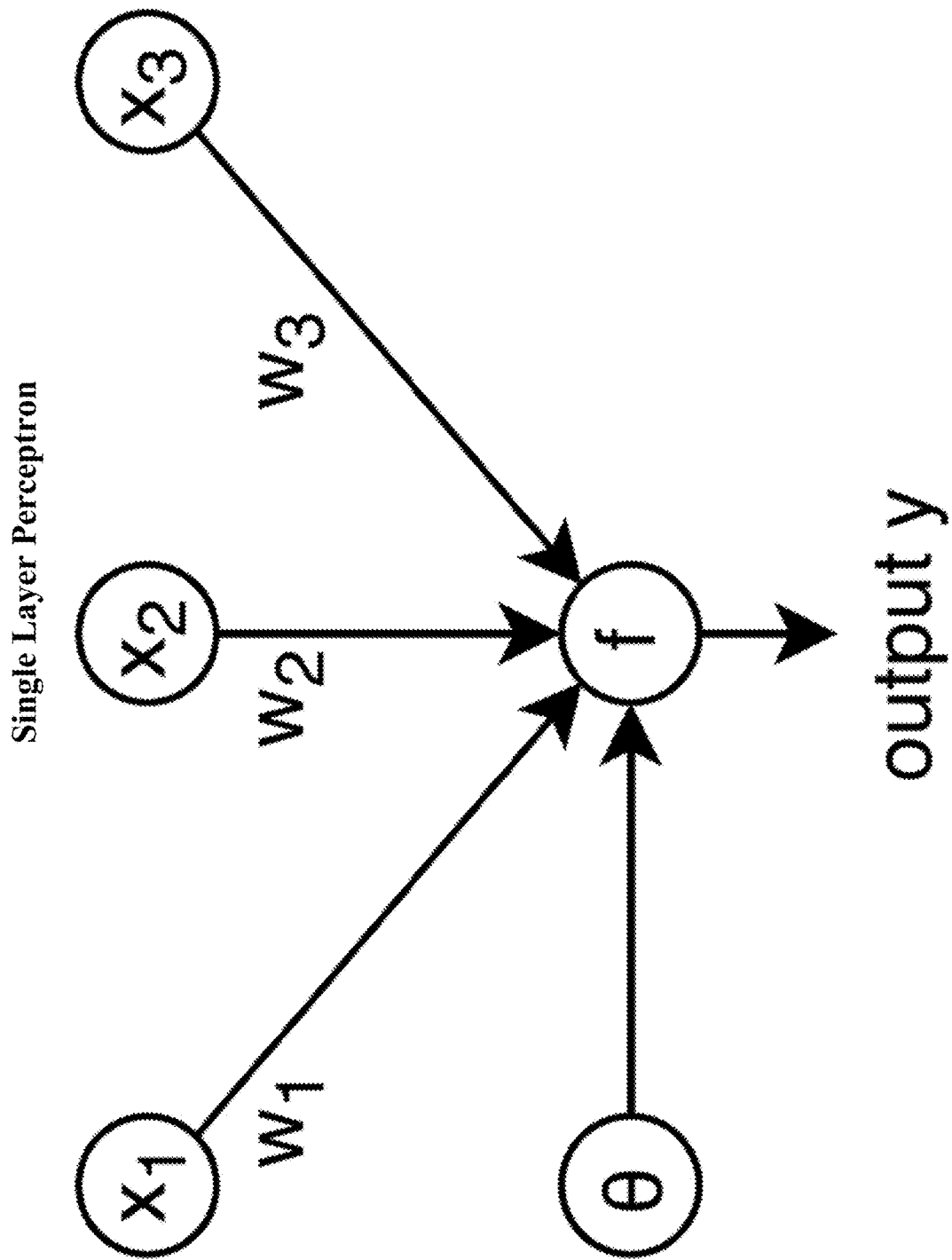
FIG. 1 shows a single layer perceptron (SLP).
Figure 2:
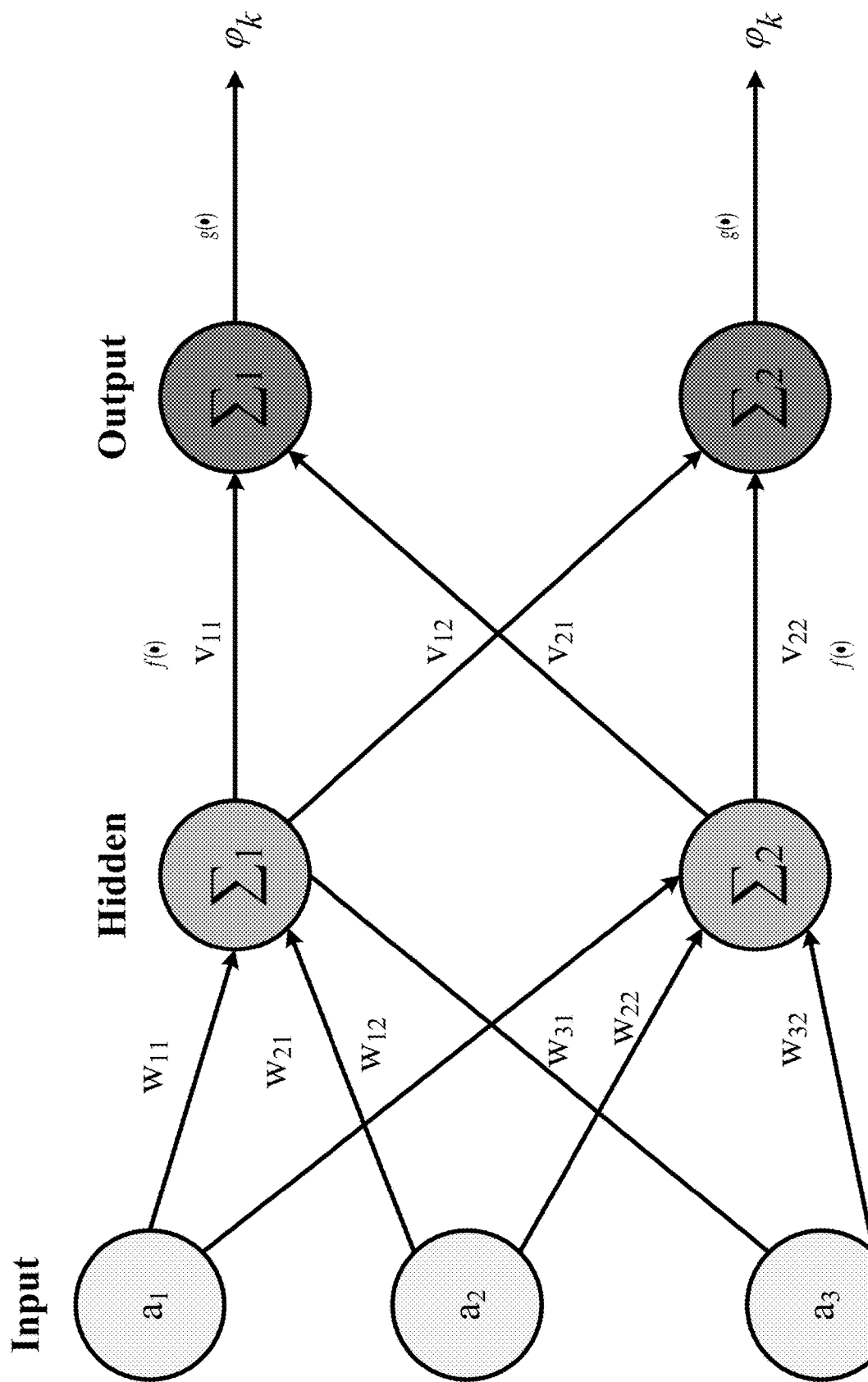
FIG. 2 shows one implementation of a feed-forward neural network with multiple layers.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

INTRODUCTION

Convolutional Neural Networks

A convolutional neural network is a special type of neural network. The fundamental difference between a densely connected layer and a convolution layer is this: Dense layers learn global patterns in their input feature space, whereas convolution layers learn local patters: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere: for example, in the upper-left corner. A densely connected network would have to learn the pattern anew if it appeared at a new location. This makes convolutional neural networks data efficient because they need fewer training samples to learn representations they have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

Figure 3:
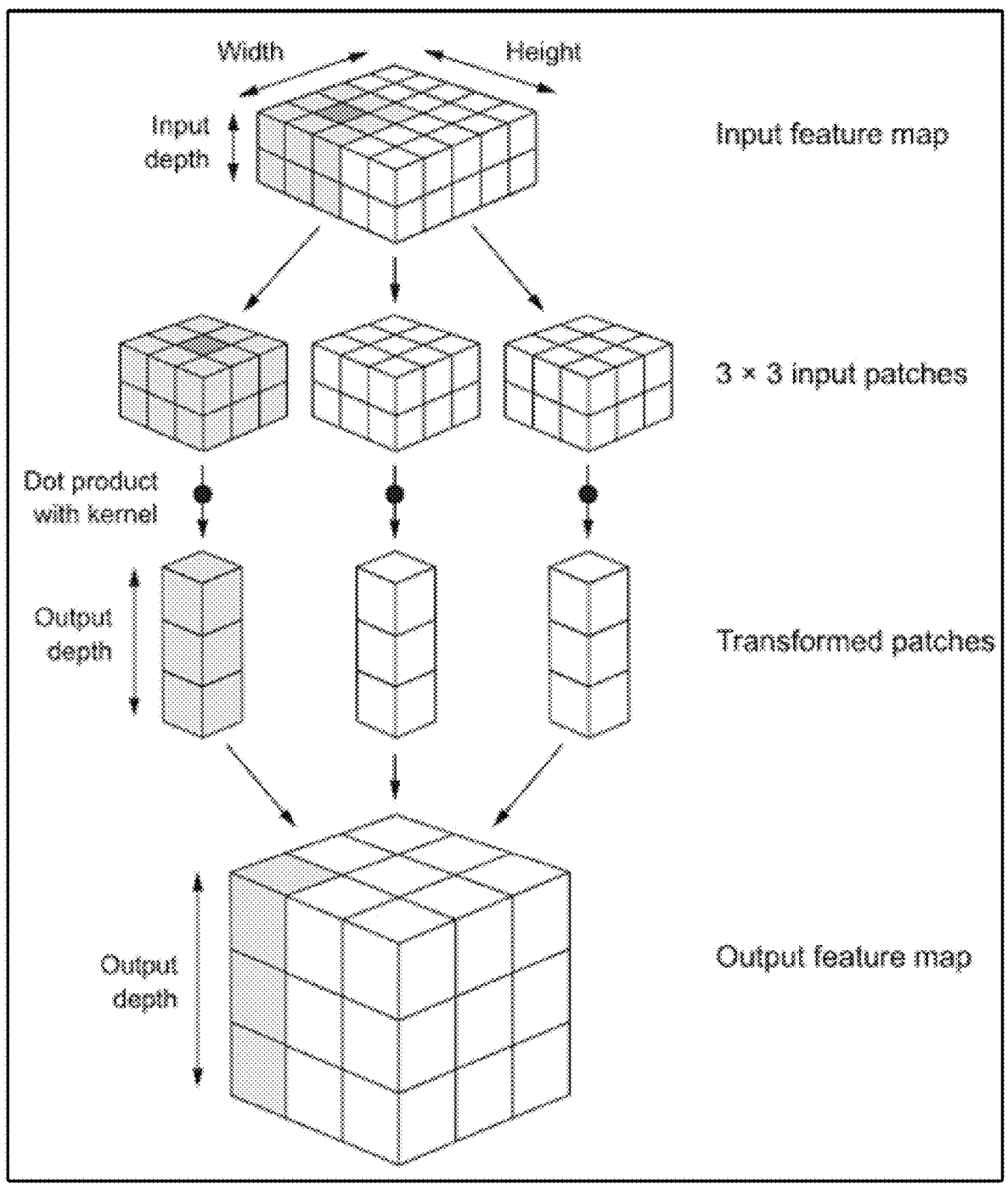
FIG. 3 depicts one implementation of workings of a convolutional neural network.

A convolution works by sliding these windows of size 3×3 or 5×5 over the 3D input feature map, stopping at every location, and extracting the 3D patch of surrounding features (shape (window_height, window_width, input_depth)). Each such 3D patch is ten transformed (via a tensor product with the same learned weight matrix, called the convolution kernel) into a 1D vector of shape (output_depth). All of these vectors are then spatially reassembled into a 3D output map of shape (height, width, output_depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i−1: i+1, j−1:J+1, :]. The full process is detailed in FIG. 3.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

Figure 4:
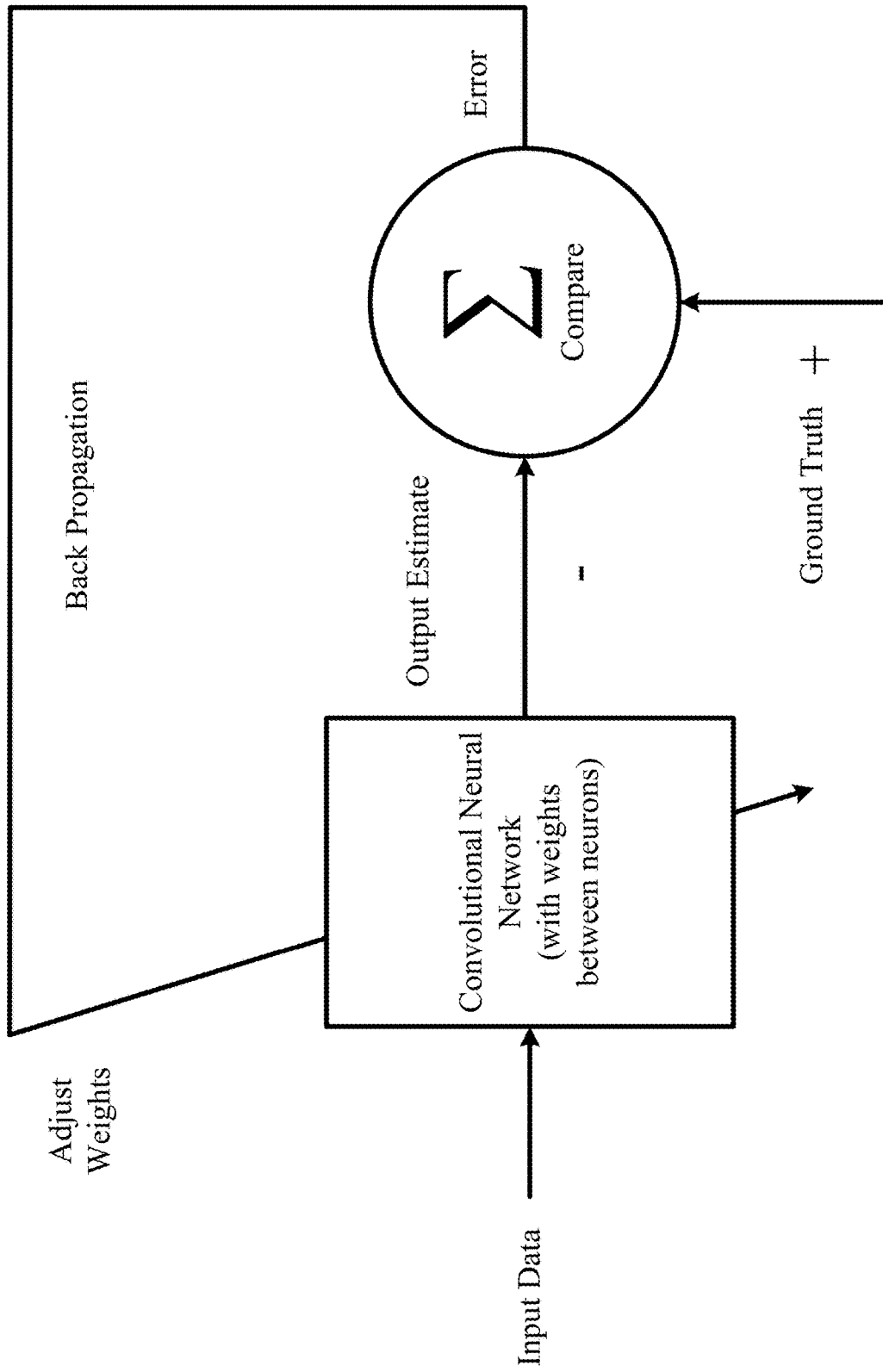
FIG. 4 depicts a block diagram of training a convolutional neural network in accordance with one implementation of the technology disclosed.

FIG. 4 depicts a block diagram of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where $\delta$ = (ground truth) − (actual output)

In one implementation, the training rule is defined as:

$$w_{nm} \leftarrow w_{nm} + \alpha(t_m - \varphi_m)a_n$$

In the equation above: the arrow indicates an update of the value; $t_m$ is the target value of neuron m; $\varphi_m$ is the computed current output of neuron m; $a_n$ is input n; and $\alpha$ is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1 + e^{-h}}$$

In the sigmoid function above, h is the weighted sum computed by a neuron. The sigmoid function has the following derivative:

$$\frac{\partial \varphi}{\partial h} = \varphi(1-\varphi)$$

The algorithm includes computing the activation of all neurons in the network, yielding an output for the forward pass. The activation of neuron m in the hidden layers is described as:

$$\varphi_m = \frac{1}{1+e^{-h_m}}$$

$$h_m = \sum_{n=1}^{N} a_n w_{nm}$$

This is done for all the hidden layers to get the activation described as:

$$\varphi_k = \frac{1}{1+e^{h_k}}$$

$$h_k = \sum_{m=1}^{M} \varphi_m v_{mk}$$

Then, the error and the correct weights are calculated per layer. The error at the output is computed as:

$$\delta_{ok} = (t_k - \varphi_k)\varphi_k(1-\varphi_k)$$

The error in the hidden layers is calculated as:

$$\delta_{hm} = \varphi_m(1-\varphi_m)\sum_{k=1}^{K} v_{mk}\delta_{ok}$$

The weights of the output layer are updated as:

$$v_{mk} \leftarrow v_{mk} + \alpha \delta_{ok}\varphi_m$$

The weights of the hidden layers are updated using the learning rate α as:

$$v_{nm} \leftarrow w_{nm} + \alpha \delta_{hm} a_n$$

In one implementation, the convolutional neural network uses a gradient descent optimization to compute the error across all the layers. In such an optimization, for an input feature vector x and the predicted output ŷ, the loss function is defined as l for the cost of predicting ŷ when the target is y, i.e. l(ŷ, y). The predicted output ŷ is transformed from the input feature vector x using function $f$. Function $f$ is parameterized by the weights of convolutional neural network, i.e. ŷ=$f_w$(x). The loss function is described as l(ŷ, y)=l($f_w$(x),y), or Q(z, w)=l($f_w$(x),y) where z is an input and output data pair (x, y). The gradient descent optimization is performed by updating the weights according to:

$$v_{t+1} = \mu v_t - \alpha \frac{1}{n}\sum_{i=1}^{N} \nabla wtQ(zt, wt)$$

$$w_{t+1} = w_t + v_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $z_t$, described as:

$$v_{t+1} = \mu v - \alpha \nabla_w Q(z_t, w_t)$$

$$w_{t+1} = w_t + v_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image and the other image, called the "kernel", applied as a filter on the input image, producing an output image. Thus, for an input vector $f$ of length n and a kernel g of length m, the convolution $f*g$ off and g is defined as:

$$(f*g)(i) = \sum_{j=1}^{m} g(j) \cdot f(i-j+m/2)$$

The convolution operation includes sliding the kernel over the input image. For each position of the kernel, the overlapping values of the kernel and the input image are multiplied and the results are added. The sum of products is the value of the output image at the point in the input image where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Non-Linear Layers

Figure 5:
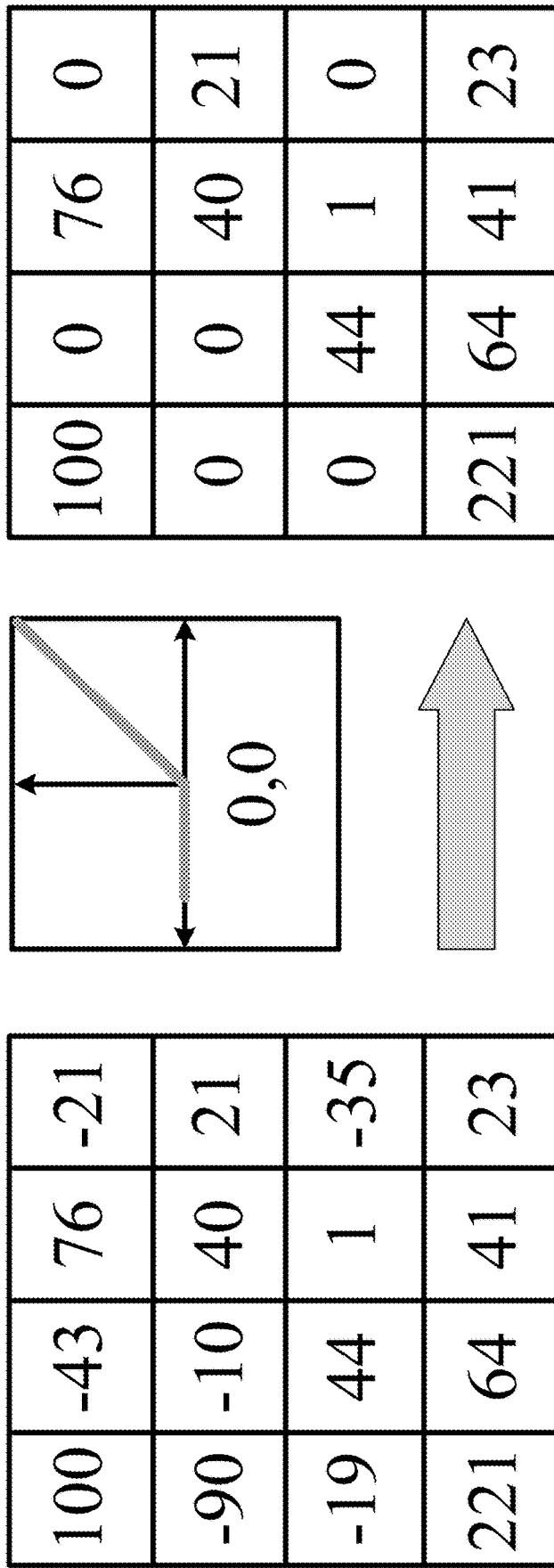
FIG. 5 shows one implementation of a ReLU non-linear layer in accordance with one implementation of the technology disclosed.

FIG. 5 shows one implementation of non-linear layers in accordance with one implementation of the technology disclosed. Non-linear layers use different non-linear trigger functions to signal distinct identification of likely features on each hidden layer. Non-linear layers use a variety of specific functions to implement the non-linear triggering, including the rectified linear units (ReLUs), hyperbolic tangent, absolute of hyperbolic tangent, sigmoid and continuous trigger (non-linear) functions. In one implementation, a ReLU activation implements the function y=max(x, 0) and keeps the input and output sizes of a layer the same. The advantage of using ReLU is that the convolutional neural network is trained many times faster. ReLU is a non-continuous, non-saturating activation function that is linear with respect to the input if the input values are larger than zero and zero otherwise. Mathematically, a ReLU activation function is described as:

$$\varphi(h) = \max(h, 0)$$

$$\varphi(h) = \begin{cases} h \text{ if } h > 0 \\ 0 \text{ if } h \leq 0 \end{cases}$$

In other implementations, the convolutional neural network uses a power unit activation function, which is a continuous, non-saturating function described by:

$$\varphi(h) = (a+bh)^c$$

In the equation above, a, b and c are parameters controlling the shift, scale and power respectively. The power activation function is able to yield x and y-antisymmetric activation if c is odd and y-symmetric activation if c is even. In some implementations, the unit yields a non-rectified linear activation.

In yet other implementations, the convolutional neural network uses a sigmoid unit activation function, which is a continuous, saturating function described by the following logistic function:

$$\varphi(h) = \frac{1}{1 + e^{-\beta h}}$$

In the equation above, β=1. The sigmoid unit activation function does not yield negative activation and is only antisymmetric with respect to the y-axis.

Dilated Convolutions

Figure 6:
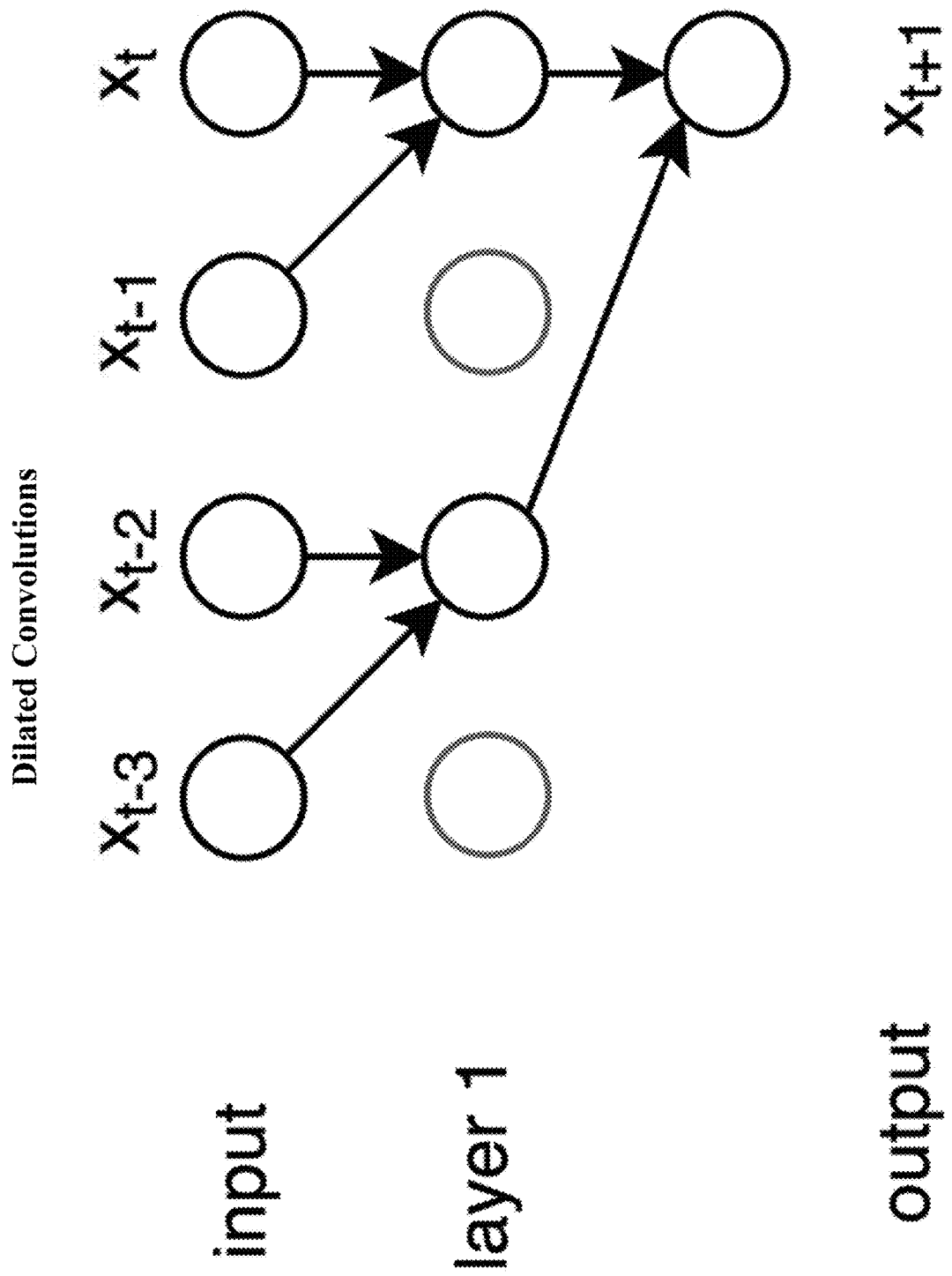
FIG. 6 illustrates dilated convolutions.

FIG. 6 illustrates dilated convolutions. Dilated convolutions, sometimes called atrous convolutions, which literally means with holes. The French name has its origins in the algorithme a trous, which computes the fast dyadic wavelet transform. In these type of convolutional layers, the inputs corresponding to the receptive field of the filters are not neighboring points. This is illustrated in FIG. 6. The distance between the inputs is dependent on the dilation factor.

Sub-Sampling Layers

Figure 7:
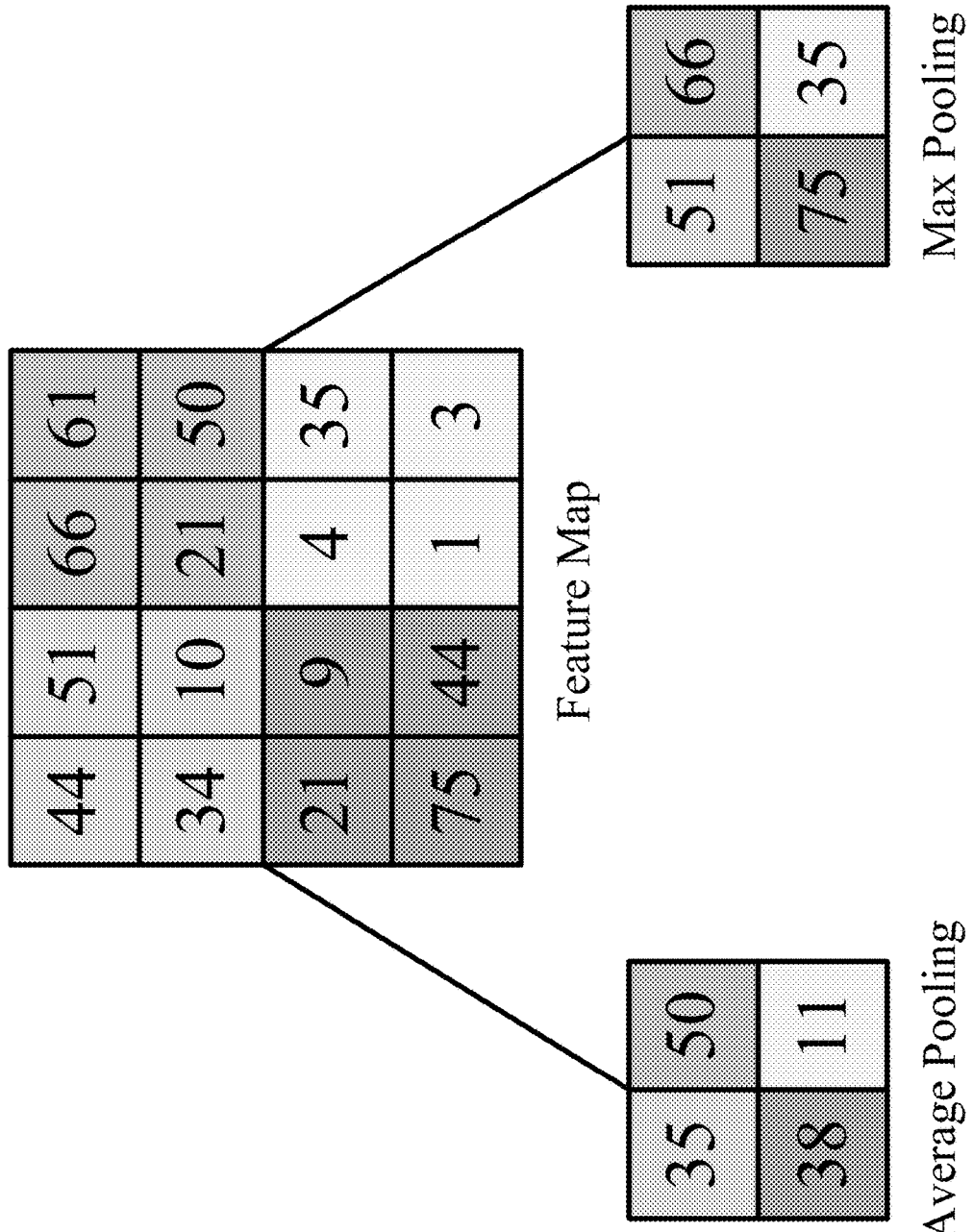
FIG. 7 is one implementation of sub-sampling layers (average/max pooling) in accordance with one implementation of the technology disclosed.

FIG. 7 is one implementation of sub-sampling layers in accordance with one implementation of the technology disclosed. Sub-sampling layers reduce the resolution of the features extracted by the convolution layers to make the extracted features or feature maps-robust against noise and distortion. In one implementation, sub-sampling layers employ two types of pooling operations, average pooling and max pooling. The pooling operations divide the input into non-overlapping two-dimensional spaces. For average pooling, the average of the four values in the region is calculated. For max pooling, the maximum value of the four values is selected.

In one implementation, the sub-sampling layers include pooling operations on a set of neurons in the previous layer by mapping its output to only one of the inputs in max pooling and by mapping its output to the average of the input in average pooling. In max pooling, the output of the pooling neuron is the maximum value that resides within the input, as described by:

$$\varphi_o = \max(\varphi_1, \varphi_2, \ldots, \varphi_N)$$

In the equation above, N is the total number of elements within a neuron set.

In average pooling, the output of the pooling neuron is the average value of the input values that reside with the input neuron set, as described by:

$$\varphi_o = \frac{1}{N} \sum_{n=1}^{N} \varphi_n$$

In the equation above, N is the total number of elements within input neuron set.

In FIG. 7, the input is of size 4×4. For 2×2 sub-sampling, a 4×4 image is divided into four non-overlapping matrices of size 2×2. For average pooling, the average of the four values is the whole-integer output. For max pooling, the maximum value of the four values in the 2×2 matrix is the whole-integer output.

Convolution Examples

Figure 8:
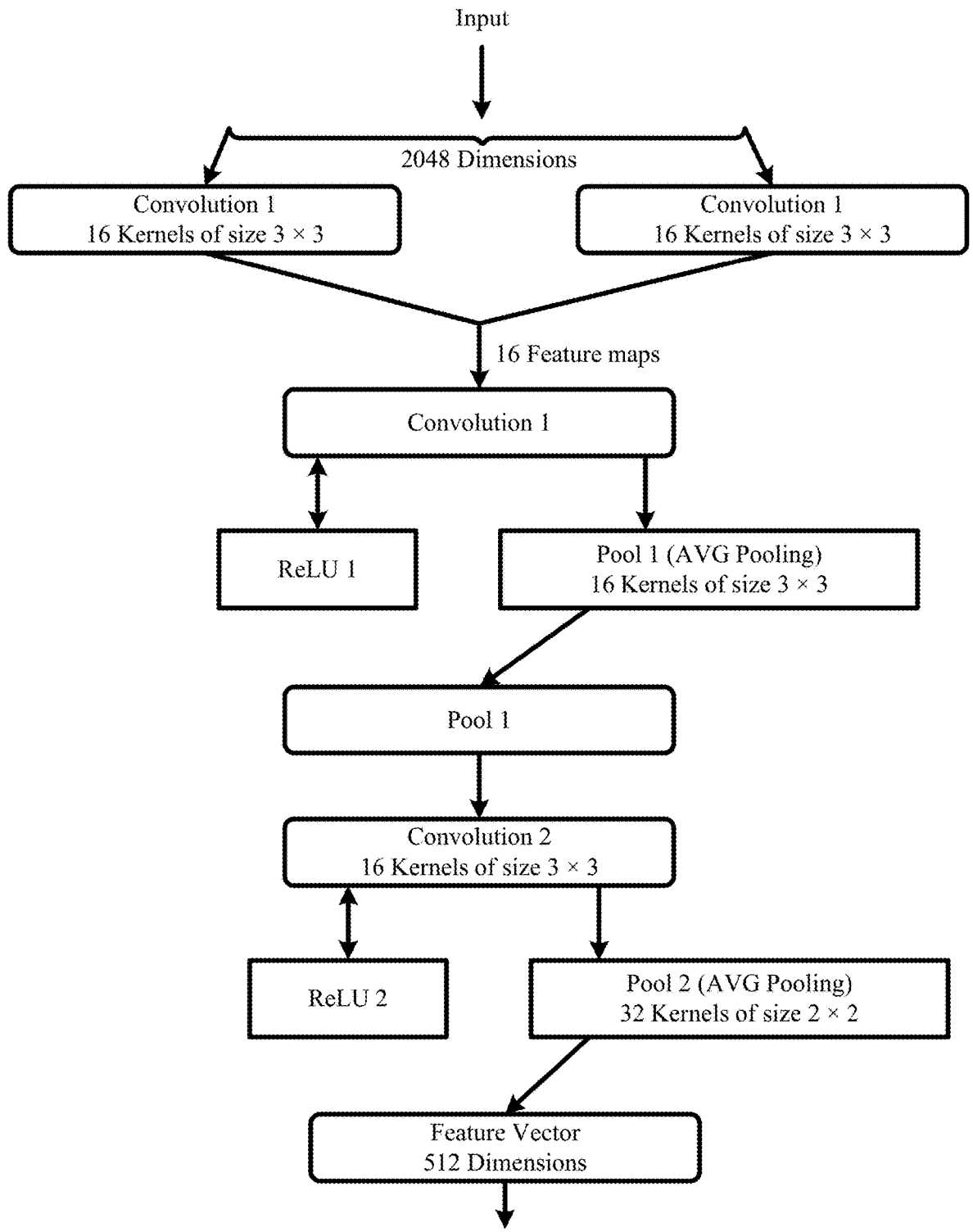
FIG. 8 depicts one implementation of a two-layer convolution of the convolution layers.

FIG. 8 depicts one implementation of a two-layer convolution of the convolution layers. In FIG. 8, an input of size 2048 dimensions is convolved. At convolution 1, the input is convolved by a convolutional layer comprising of two channels of sixteen kernels of size 3×3. The resulting sixteen feature maps are then rectified by means of the ReLU activation function at ReLU1 and then pooled in Pool 1 by means of average pooling using a sixteen channel pooling layer with kernels of size 3×3. At convolution 2, the output of Pool 1 is then convolved by another convolutional layer comprising of sixteen channels of thirty kernels with a size of 3×3. This is followed by yet another ReLU2 and average pooling in Pool 2 with a kernel size of 2×2. The convolution layers use varying number of strides and padding, for example, zero, one, two and three. The resulting feature vector is five hundred and twelve (512) dimensions, according to one implementation.

In other implementations, the convolutional neural network uses different numbers of convolution layers, sub-sampling layers, non-linear layers and fully connected layers. In one implementation, the convolutional neural network is a shallow network with fewer layers and more neurons per layer, for example, one, two or three fully connected layers with hundred (100) to two hundred (200) neurons per layer. In another implementation, the convolutional neural network is a deep network with more layers and fewer neurons per layer, for example, five (5), six (6) or eight (8) fully connected layers with thirty (30) to fifty (50) neurons per layer.

Forward Pass

The output of a neuron of row x, column y in the $l^{th}$ convolution layer and $k^{th}$ feature map for $f$ number of convolution cores in a feature map is determined by the following equation:

$$O_{x,y}^{(l,k)} = \tanh\left(\sum_{t=0}^{f-1} \sum_{r=0}^{k_h} \sum_{c=0}^{k_w} W_{(r,c)}^{(k,t)} O_{(x+r,x+c)}^{(l-1,t)} + Bias^{(l,k)}\right)$$

The output of a neuron of row x, column y in the $l^{th}$ sub-sample layer and $k^{th}$ feature map is determined by the following equation:

$$O_{x,y}^{(l,k)} = \tanh\left(W^{(k)}\sum_{r=0}^{S_h}\sum_{c=0}^{S_w} O_{(x\times S_h+r, y\times S_w+c)}^{(l-1,k)} + Bias^{(l,k)}\right)$$

The output of an $i^{th}$ neuron of the $l^{th}$ output layer is determined by the following equation:

$$O_{(l,i)} = \tanh\left(\sum_{j=0}^{H} O_{(l-1,j)} W_{(i,j)}^{l} + BIAS^{(l,j)}\right)$$

Backpropagation

The output deviation of a $k^{th}$ neuron in the output layer is determined by the following equation:

$$d(O_k^o) = y_k - t_k$$

The input deviation of a $k^{th}$ neuron in the output layer is determined by the following equation:

$$d(I_k^o) = (y_k - t_k)\varphi'(v_k) = \varphi'(v_k)d(O_k^o)$$

The weight and bias variation of a $k^{th}$ neuron in the output layer is determined by the following equation:

$$\Delta W_{k,x}^o = d(I_k^o) y_{k,x}$$

$$\Delta Bias_k^o = d(I_k^o)$$

The output bias of a $k^{th}$ neuron in the hidden layer is determined by the following equation:

$$d(O_k^H) = \sum_{i=0}^{i<84} d(I_i^o) W_{i,k}$$

The input bias of a $k^{th}$ neuron in the hidden layer is determined by the following equation:

$$d(I_k^H) = \varphi'(v_k) d(O_k^H)$$

The weight and bias variation in row x, column y in a $m^{th}$ feature map of a prior layer receiving input from k neurons in the hidden layer is determined by the following equation:

$$\Delta W_{m,x,y}^{H,k} = d(I_k^H) y_{x,y}^m$$

$$\Delta Bias_k^H = d(I_k^H)$$

The output bias of row x, column y in a $m^{th}$ feature map of sub-sample layer S is determined by the following equation:

$$d(O_{x,y}^{S,m}) = \sum_{k}^{170} d(I_{m,x,y}^H) W_{m,x,y}^{H,k}$$

The input bias of row x, column y in a $m^{th}$ feature map of sub-sample layer S is determined by the following equation:

$$d(I_{x,y}^{S,m}) = \varphi'(v_k) d(O_{x,y}^{S,m})$$

The weight and bias variation in row x, column y in a $m^{th}$ feature map of sub-sample layer S and convolution layer C is determined by the following equation:

$$\Delta W^{S,m} = \sum_{x=0}^{fh}\sum_{y=0}^{fw} d(I_{[x/2],[y/2]}^{S,m}) O_{x,y}^{C,m}$$

$$\Delta Bias^{S,m} = \sum_{x=0}^{fh}\sum_{y=0}^{fw} d(O_{x,y}^{S,m})$$

The output bias of row x, column y in a $k^{th}$ feature map of convolution layer C is determined by the following equation:

$$d(O_{x,y}^{C,k}) = d(I_{[x/2],[y/2]}^{S,k}) W^k$$

The input bias of row x, column y in a $k^{th}$ feature map of convolution layer C is determined by the following equation:

$$d(I_{x,y}^{C,k}) = \varphi'(v_k) d(O_{x,y}^{C,k})$$

The weight and bias variation in row r, column c in an $m^{th}$ convolution core of a $k^{th}$ feature map of $l^{th}$ convolution layer C:

$$\Delta W_{r,c}^{k,m} = \sum_{x=0}^{fh}\sum_{y=0}^{fw} d(I_{x,y}^{C,m}) O_{x+r,y+c}^{l-1,m}$$

$$\Delta Bias^{C,k} = \sum_{x=0}^{fh}\sum_{y=0}^{fw} d(I_{x,y}^{C,k})$$

Residual Connections

Figure 9:
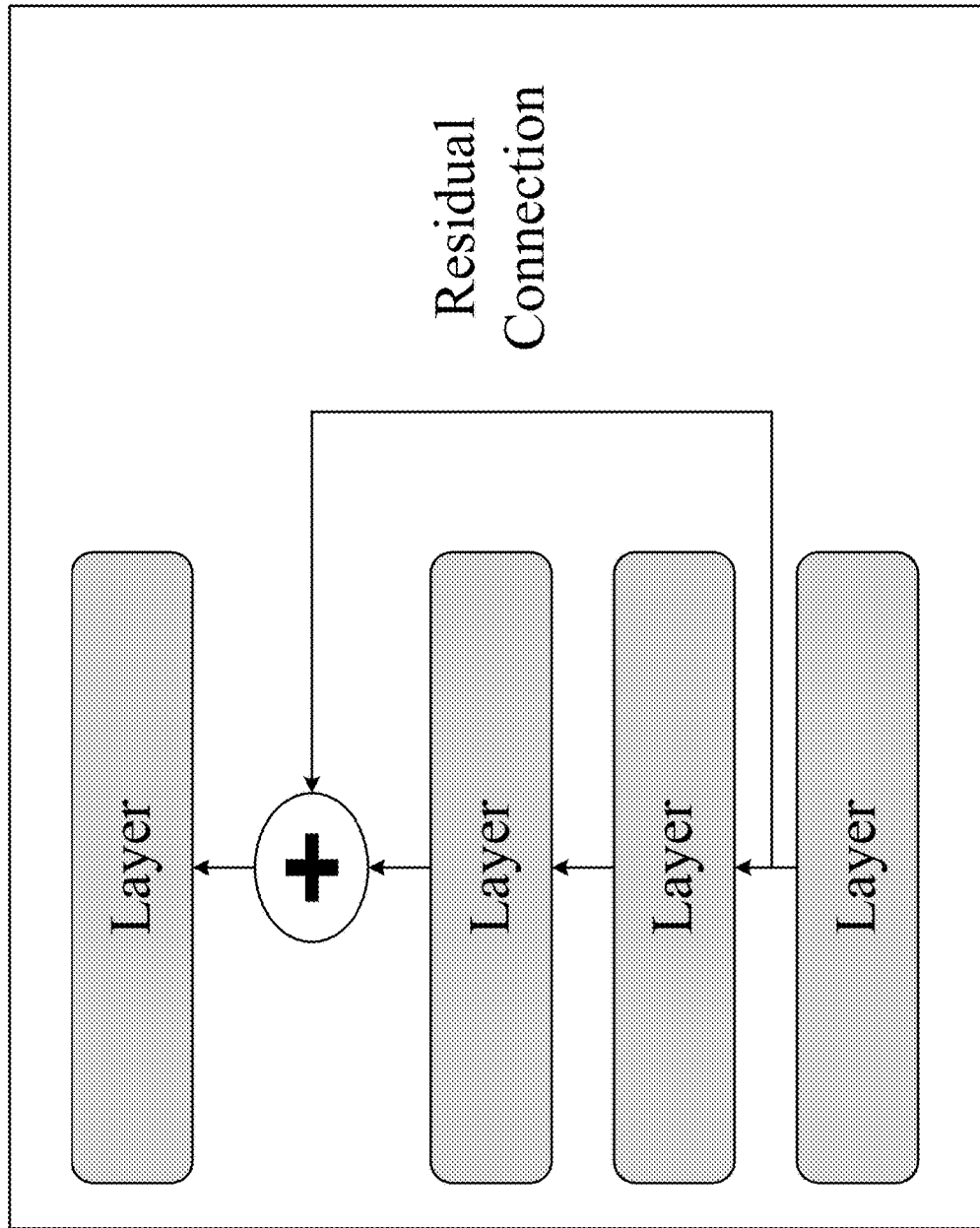
FIG. 9 depicts a residual connection that reinjects prior information downstream via feature-map addition.

FIG. 9 depicts a residual connection that reinjects prior information downstream via feature-map addition. A residual connection comprises reinjecting previous representations into the downstream flow of data by adding a past output tensor to a later output tensor, which helps prevent information loss along the data-processing flow. Residual connections tackle two common problems that plague any large-scale deep-learning model: vanishing gradients and representational bottlenecks. In general, adding residual connections to any model that has more than 10 layers is likely to be beneficial. As discussed above, a residual connection comprises making the output of an earlier layer available as input to a later layer, effectively creating a shortcut in a sequential network. Rather than being concatenated to the later activation, the earlier output is summed with the later activation, which assumes that both activations are the same size. If they are of different sizes, a linear transformation to reshape the earlier activation into the target shape can be used.

Residual Learning and Skip-Connections

Figure 10:
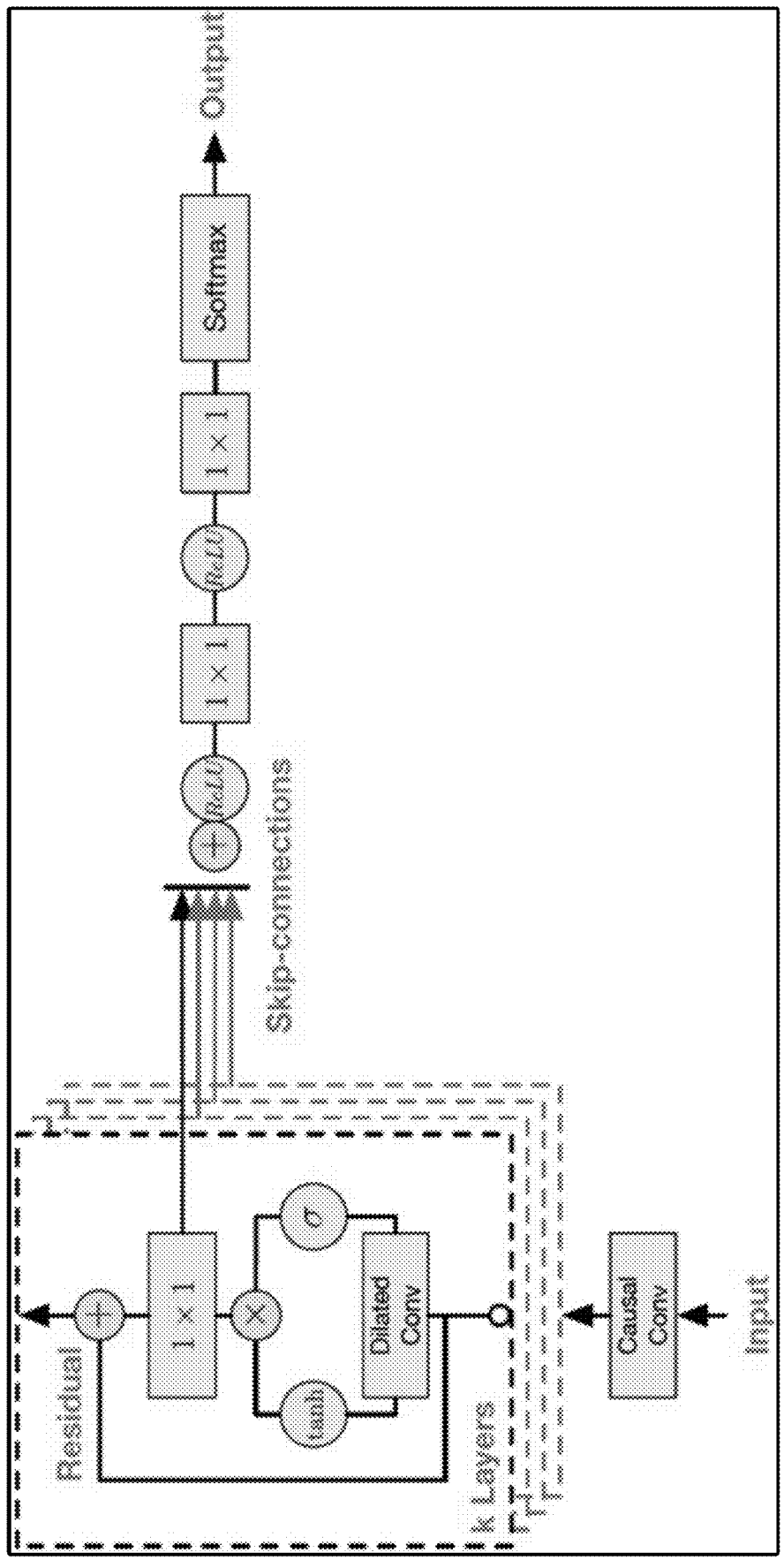
FIG. 10 depicts one implementation of residual blocks and skip-connections.

FIG. 10 depicts one implementation of residual blocks and skip-connections. The main idea of residual learning is that the residual mapping is much easier to be learned than the original mapping. Residual network stacks a number of residual units to alleviate the degradation of training accuracy. Residual blocks make use of special additive skip connections to combat vanishing gradients in deep neural networks. At the beginning of a residual block, the data flow is separated into two streams: the first carries the unchanged input of the block, while the second applies weights and non-linearities. At the end of the block, the two streams are merged using an element-wise sum. The main advantage of such constructs is to allow the gradient to flow through the network more easily.

Benefited from residual network, deep convolutional neural networks (CNNs) can be easily trained and improved accuracy has been achieved for image classification and object detection. Convolutional feed-forward networks connect the output of the $l^{th}$ layer as input to the $(l+1)^{th}$ layer, which gives rise to the following layer transition: $x_l = H_l(x_{l-1})$. Residual blocks add a skip-connection that bypasses the non-linear transformations with an identify function: $x_l = H_l(x_{l-1}) + x_{l-1}$. An advantage of residual blocks is that the gradient can flow directly through the identity function from later layers to the earlier layers. However, the identity function and the output of H, are combined by summation, which may impede the information flow in the network.

WaveNet

The WaveNet is a deep neural network for generating raw audio waveforms. The WaveNet distinguishes itself from other convolutional networks since it is able to take relatively large 'visual fields' at low cost. Moreover, it is able to add conditioning of the signals locally and globally, which allows the WaveNet to be used as a text to speech (TTS) engine with multiple voices, is the TTS gives local conditioning and the particular voice the global conditioning.

Figure 11:
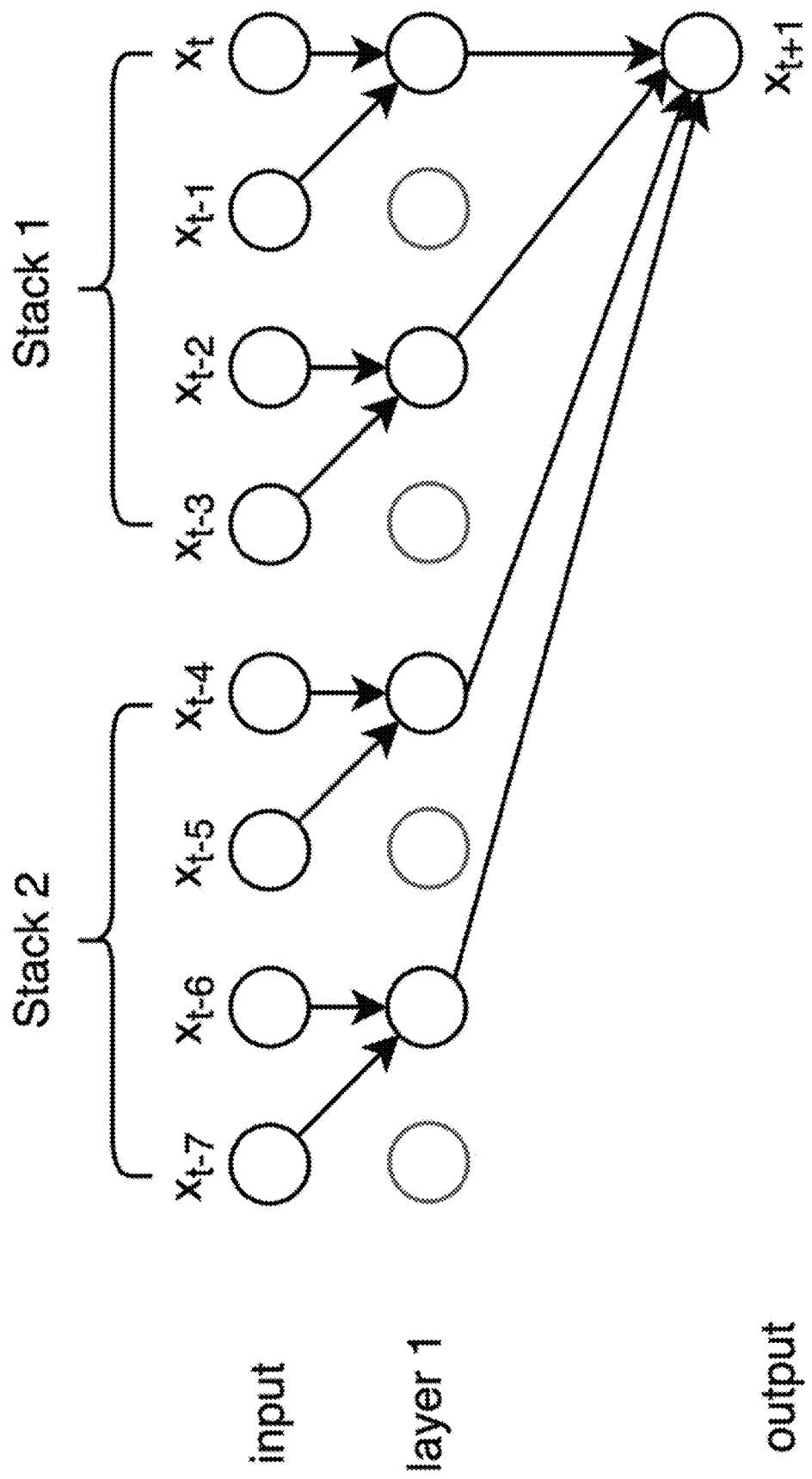
FIG. 11 shows one implementation of stacked dilated convolutions.

The main building blocks of the WaveNet are the causal dilated convolutions. As an extension on the causal dilated convolutions, the WaveNet also allows stacks of these convolutions, as shown in FIG. 11. To obtain the same receptive field with dilated convolutions in this figure, another dilation layer is required. The stacks are a repetition of the dilated convolutions, connecting the outputs of dilated convolution layer to a single output. This enables the WaveNet to get a large 'visual' field of one output node at a relatively low computational cost. For comparison, to get a visual field of 512 inputs, a fully convolutional network (FCN) would require 511 layers. In the case of a dilated convolutional network, we would need eight layers. The stacked dilated convolutions only need seven layers with two stacks or six layers with four stacks. To get an idea of the differences in computational power required for covering the same visual field, the following table shows the number of weights required in the network with the assumption of one filter per layer and a filter width of two. Furthermore, it is assumed that the network is using binary encoding of the 8 bits.

| Network type | No. stacks | No. weights per channel | Total No. of weights |
|---|---|---|---|
| FCN | 1 | $2.6 \cdot 10^5$ | $2.6 \cdot 10^6$ |
| WN | 1 | 1022 | 8176 |
| WN | 2 | 1022 | 8176 |
| WN | 4 | 508 | 4064 |

The WaveNet adds a skip connection before the residual connection is made, which bypasses all the following residual blocks. Each of these skip connections is summed before passing them through a series of activation functions and convolutions. Intuitively, this is the sum of the information extracted in each layer.

Batch Normalization

Batch normalization is a method for accelerating deep network training by making data standardization an integral part of the network architecture. Batch normalization can adaptively normalize data even as the mean and variance change over time during training. It works by internally maintaining an exponential moving average of the batch-wise mean and variance of the data seen during training. The main effect of batch normalization is that it helps with gradient propagation—much like residual connections—and thus allows for deep networks. Some very deep networks can only be trained if they include multiple Batch Normalization layers.

Batch normalization can be seen as yet another layer that can be inserted into the model architecture, just like the fully connected or convolutional layer. The BatchNormalization layer is typically used after a convolutional or densely connected layer. It can also be used before a convolutional or densely connected layer. Both implementations can be used by the technology disclosed and are shown in FIG. 15. The BatchNormalization layer takes an axis argument, which specifies the feature axis that should be normalized. This argument defaults to −1, the last axis in the input tensor. This is the correct value when using Dense layers, Conv1D layers, RNN layers, and Conv2D layers with data_format set to "channels_last". But in the niche use case of Conv2D layers with data_format set to "channels_first", the features axis is axis 1; the axis argument in BatchNormalization can be set to 1.

Batch normalization provides a definition for feed-forwarding the input and computing the gradients with respect to the parameters and its own input via a backward pass. In practice, batch normalization layers are inserted after a convolutional or fully connected layer, but before the outputs are fed into an activation function. For convolutional layers, the different elements of the same feature map—i.e. the activations—at different locations are normalized in the same way in order to obey the convolutional property. Thus, all activations in a mini-batch are normalized over all locations, rather than per activation.

The internal covariate shift is the major reason why deep architectures have been notoriously slow to train. This stems from the fact that deep networks do not only have to learn a new representation at each layer, but also have to account for the change in their distribution.

The covariate shift in general is a known problem in the deep learning domain and frequently occurs in real-world problems. A common covariate shift problem is the difference in the distribution of the training and test set which can lead to suboptimal generalization performance. This problem is usually handled with a standardization or whitening preprocessing step. However, especially the whitening operation is computationally expensive and thus impractical in an online setting, especially if the covariate shift occurs throughout different layers.

The internal covariate shift is the phenomenon where the distribution of network activations change across layers due to the change in network parameters during training. Ideally, each layer should be transformed into a space where they have the same distribution but the functional relationship stays the same. In order to avoid costly calculations of covariance matrices to decorrelate and whiten the data at every layer and step, we normalize the distribution of each input feature in each layer across each mini-batch to have zero mean and a standard deviation of one.

Forward Pass

During the forward pass, the mini-batch mean and variance are calculated. With these mini-batch statistics, the data is normalized by subtracting the mean and dividing by the standard deviation. Finally, the data is scaled and shifted with the learned scale and shift parameters. The batch normalization forward pass $f_{BN}$ is depicted in FIG. 12.

In FIG. 12, $\mu_B$ is the batch mean and $\sigma_B^2$ is the batch variance, respectively. The learned scale and shift parameters are denoted by $\gamma$ and $\beta$, respectively. For clarity, the batch normalization procedure is described herein per activation and omit the corresponding indices.

Since normalization is a differentiable transform, the errors are propagated into these learned parameters and are thus able to restore the representational power of the network by learning the identity transform. Conversely, by learning scale and shift parameters that are identical to the corresponding batch statistics, the batch normalization transform would have no effect on the network, if that was the optimal operation to perform. At test time, the batch mean and variance are replaced by the respective population statistics since the input does not depend on other samples from a mini-batch. Another method is to keep running averages of the batch statistics during training and to use these to compute the network output at test time. At test time, the batch normalization transform can be expressed as illustrated in FIG. 13. In FIG. 13, $\mu_D$ and $\sigma_D^2$ denote the population mean and variance, rather than the batch statistics, respectively.

Backward Pass

Since normalization is a differentiable operation, the backward pass can be computed as depicted in FIG. 14.

Figure 16:
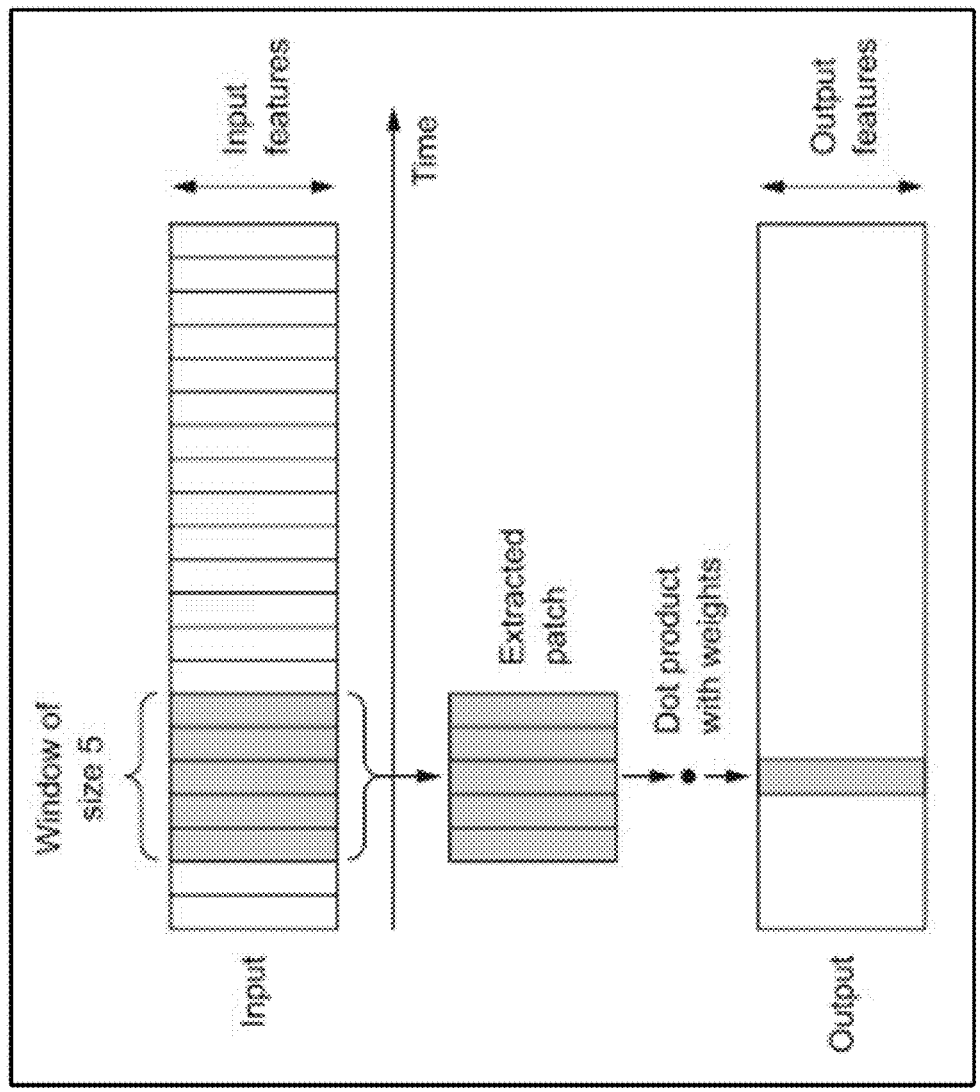
FIG. 16 shows one implementation of 1D convolution.

1D Convolution 1D convolutions extract local 1D patches or subsequences from sequences, as shown in FIG. 16. 1D convolution obtains each output timestep from a temporal patch in the input sequence. 1D convolution layers recognize local patterns in a sequence. Because the same input transformation is performed on every patch, a pattern learned at a certain position in the input sequences can be later recognized at a different position, making 1D convolution layers translation invariant for temporal translations. For instance, a 1D convolution layer processing sequences of bases using convolution windows of size 5 should be able to learn bases or base sequences of length 5 or less, and it should be able to recognize the base motifs in any context in an input sequence. A base-level 1D convolution is thus able to learn about base morphology.

Global Average Pooling

Figure 17:
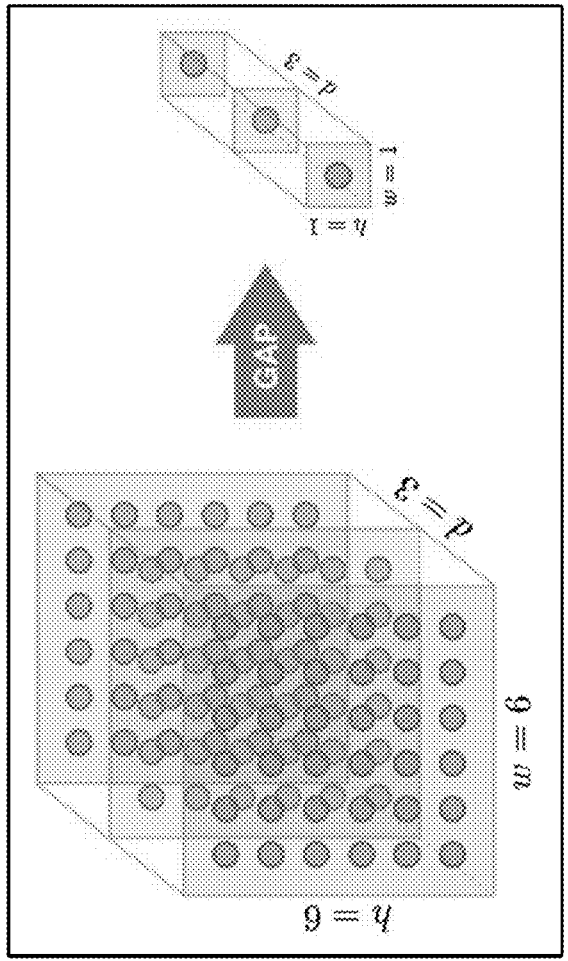
FIG. 17 illustrates how global average pooling (GAP) works.
Figure 17:
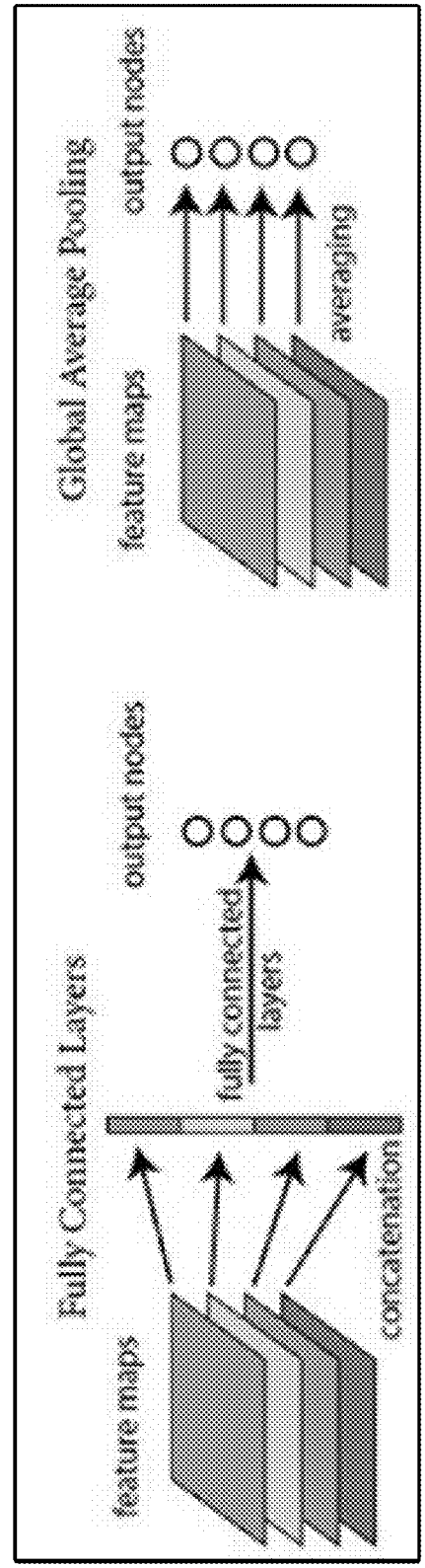

FIG. 17 illustrates how global average pooling (GAP) works. Global average pooling can be use used to replace fully connected (FC) layers for classification, by taking the spatial average of features in the last layer for scoring. The reduces the training load and bypasses overfitting issues. Global average pooling applies a structural prior to the model and it is equivalent to linear transformation with predefined weights. Global average pooling reduces the number of parameters and eliminates the fully connected layer. Fully connected layers are typically the most parameter and connection intensive layers, and global average pooling provides much lower-cost approach to achieve similar results. The main idea of global average pooling is to generate the average value from each last layer feature map as the confidence factor for scoring, feeding directly into the softmax layer.

Global average pooling have three benefits: (1) there are no extra parameters in global average pooling layers thus overfitting is avoided at global average pooling layers; (2) since the output of global average pooling is the average of the whole feature map, global average pooling will be more robust to spatial translations; and (3) because of the huge number of parameters in fully connected layers which usually take over 50% in all the parameters of the whole network, replacing them by global average pooling layers can significantly reduce the size of the model, and this makes global average pooling very useful in model compression.

Global average pooling makes sense, since stronger features in the last layer are expected to have a higher average value. In some implementations, global average pooling can be used as a proxy for the classification score. The feature maps under global average pooling can be interpreted as confidence maps, and force correspondence between the feature maps and the categories. Global average pooling can be particularly effective if the last layer features are at a sufficient abstraction for direct classification; however, global average pooling alone is not enough if multilevel features should be combined into groups like parts models, which is best performed by adding a simple fully connected layer or other classifier after the global average pooling.

Deep Learning in Genomics

Genetic variations can help explain many diseases. Every human being has a unique genetic code and there are lots of genetic variants within a group of individuals. Most of the deleterious genetic variants have been depleted from genomes by natural selection. It is important to identify which genetics variations are likely to be pathogenic or deleterious. This will help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of variants remains a great challenge due to the complexity of cell type-specific transcription regulation systems.

Regarding pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, a powerful computational model for predicting the pathogenicity of variants can have enormous benefits for both basic science and translational research.

Particular Implementations

We describe systems, methods, and articles of manufacture for using a trained atrous convolutional neural network to detect splice sites in a genomic sequence (e.g., a nucleotide sequence or an amino acid sequence). One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections— these recitations are hereby incorporated forward by reference into each of the following implementations.

A system implementation of the technology disclosed includes one or more processors coupled to the memory. The memory is loaded with computer instructions to train a splice site detector that identifies splice sites in genomic sequences (e.g., nucleotide sequences).

Figure 30:
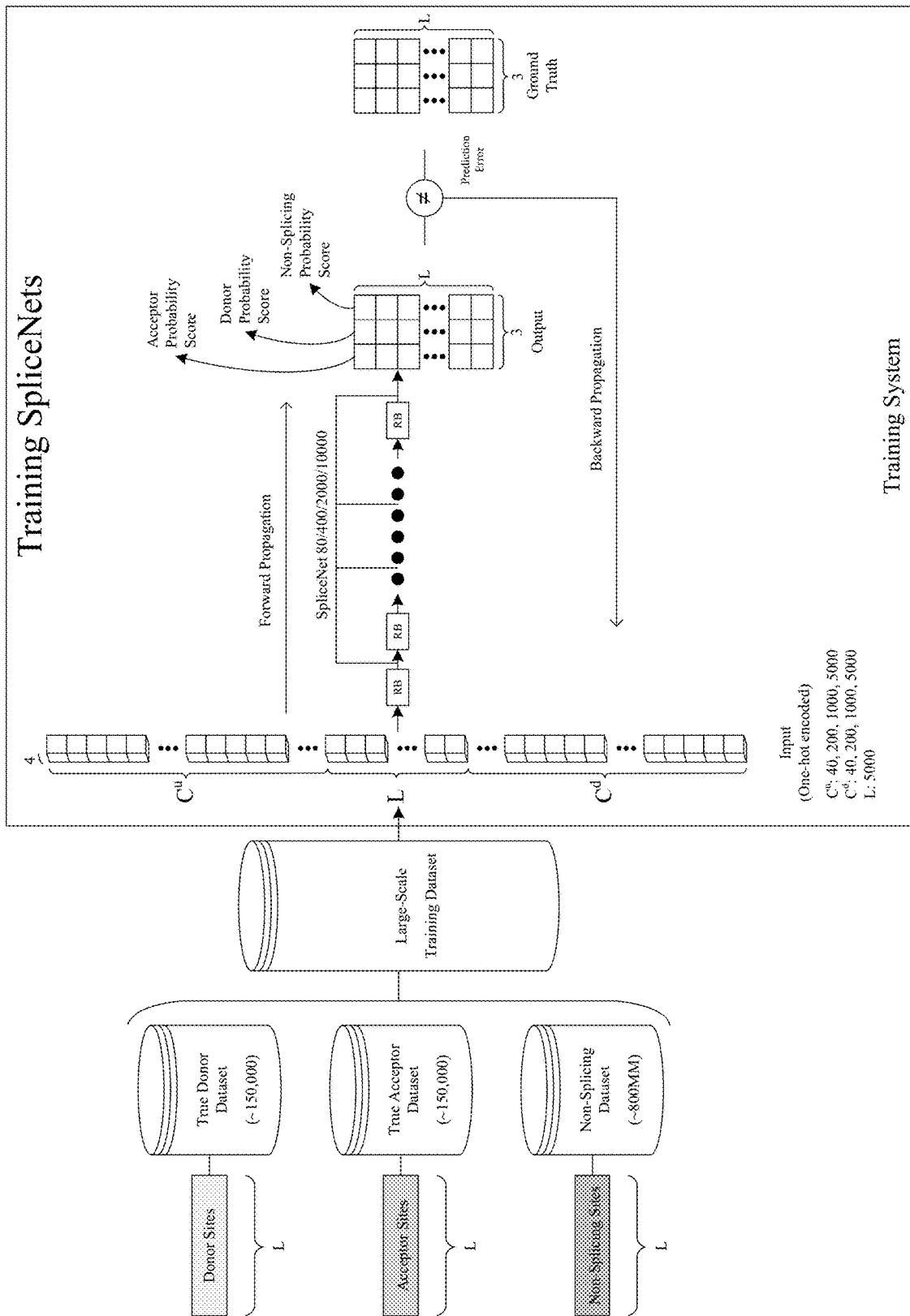
FIG. 30 depicts training of the ACNN.

As shown in FIG. 30, the system trains an atrous convolutional neural network (abbreviated ACNN) on at least 50000 training examples of donor splice sites, at least 50000 training examples of acceptor splice sites, and at least 100000 training examples of non-splicing sites. Each training example is a target nucleotide sequence having at least one target nucleotide flanked by at least 20 nucleotides on each side.

An ACNN is a convolutional neural network that uses atrous/dilated convolutions which allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

As shown in FIG. 30, for evaluating a training example using the ACNN, the system provides, as input to the ACNN, a target nucleotide sequence further flanked by at least 40 upstream context nucleotides and at least 40 downstream context nucleotides.

As shown in FIG. 30, based on the evaluation, the ACNN then produces, as output, triplet scores for likelihood that each nucleotide in the target nucleotide sequence is a donor splice site, an acceptor splice site, or a non-splicing site.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Figure 25:
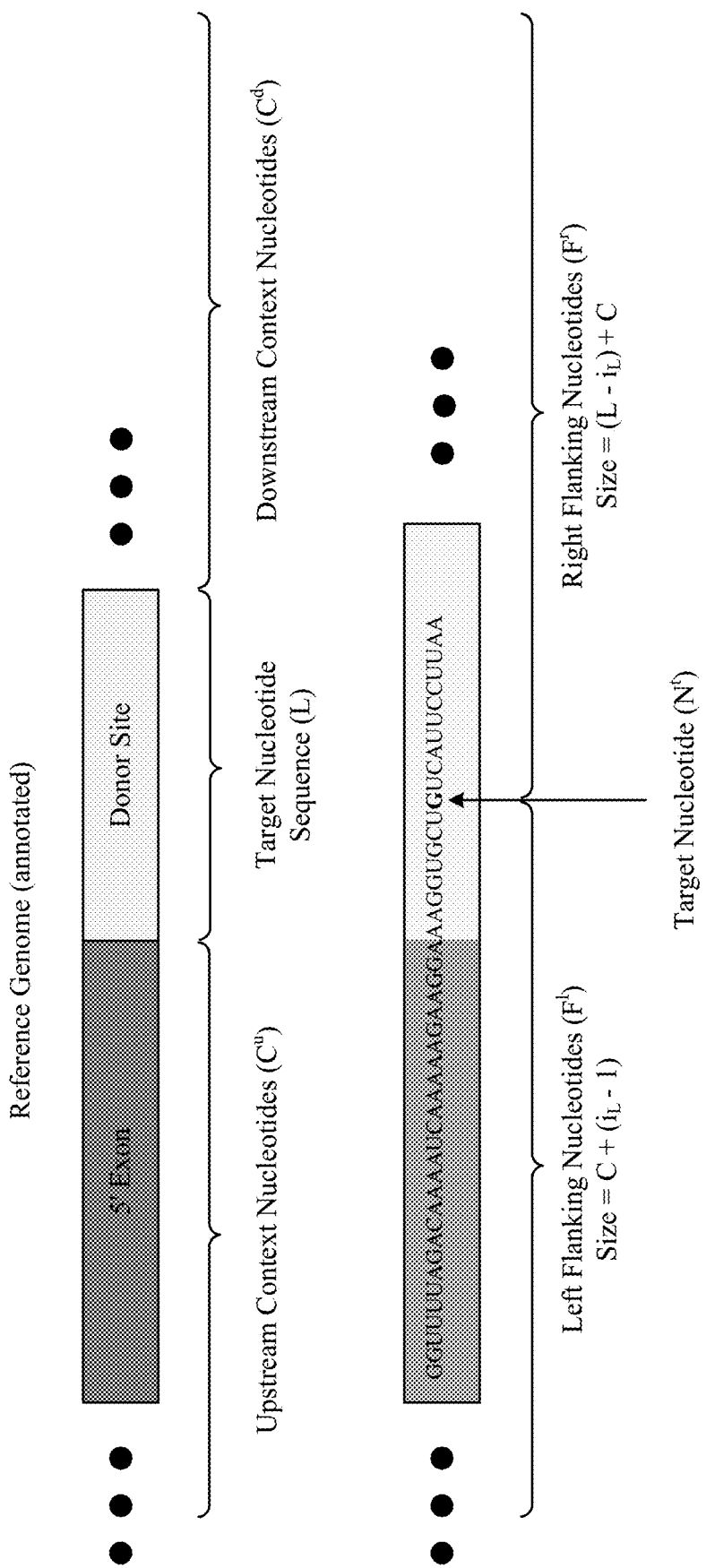
FIGS. 25, 26, and 27 show various types of inputs processed by the ACNN and the CNN.
Figure 26:
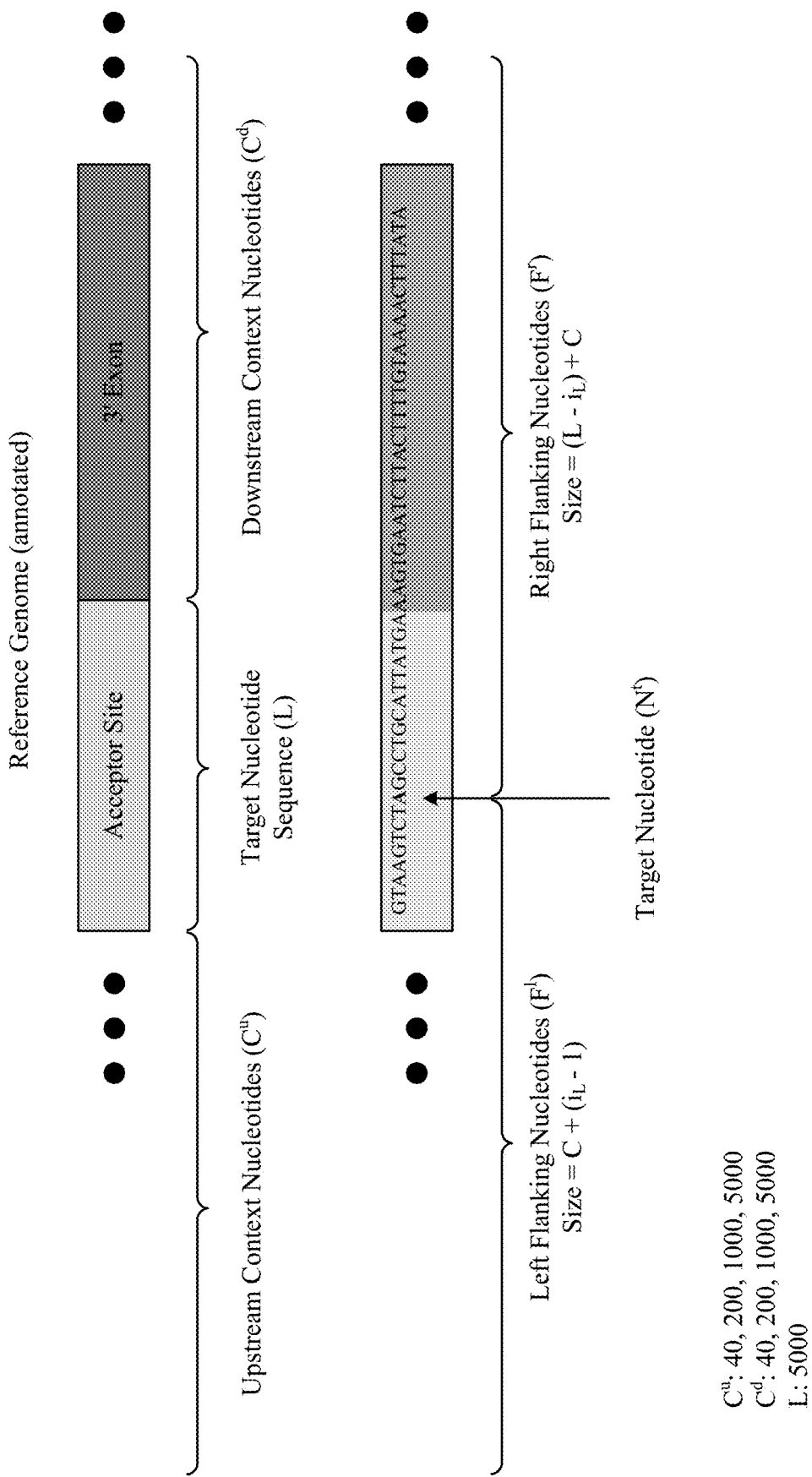
Figure 27:
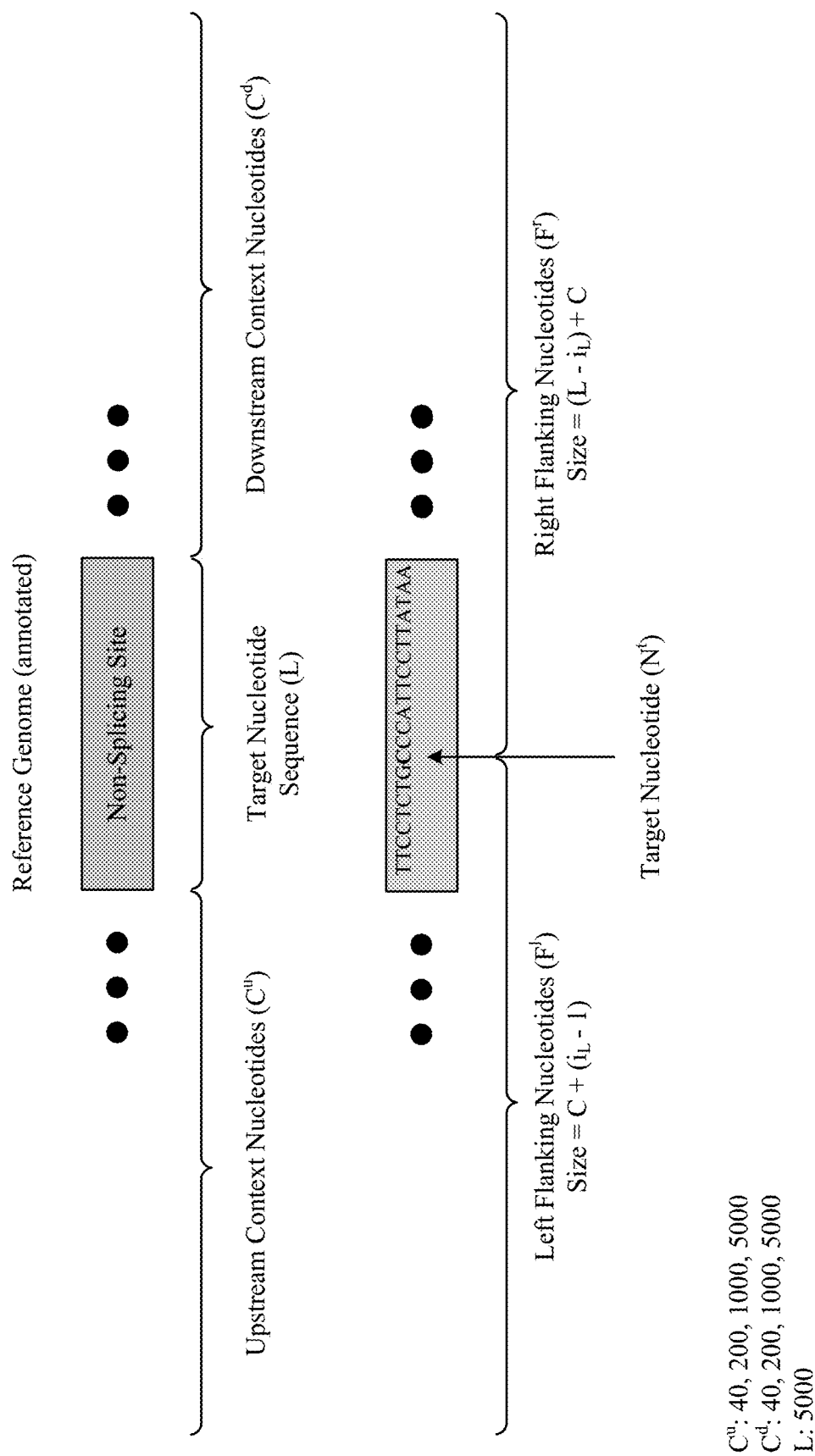

As shown in FIGS. 25, 26, and 27, the input can comprise a target nucleotide sequence that has a target nucleotide flanked by 2500 nucleotides on each side. In such an implementation, the target nucleotide sequence is further flanked by 5000 upstream context nucleotides and 5000 downstream context nucleotides.

The input can comprise a target nucleotide sequence that has a target nucleotide flanked by 100 nucleotides on each side. In such an implementation, the target nucleotide sequence is further flanked by 200 upstream context nucleotides and 200 downstream context nucleotides.

The input can comprise a target nucleotide sequence that has a target nucleotide flanked by 500 nucleotides on each side. In such an implementation, the target nucleotide sequence is further flanked by 1000 upstream context nucleotides and 1000 downstream context nucleotides.

Figure 28:
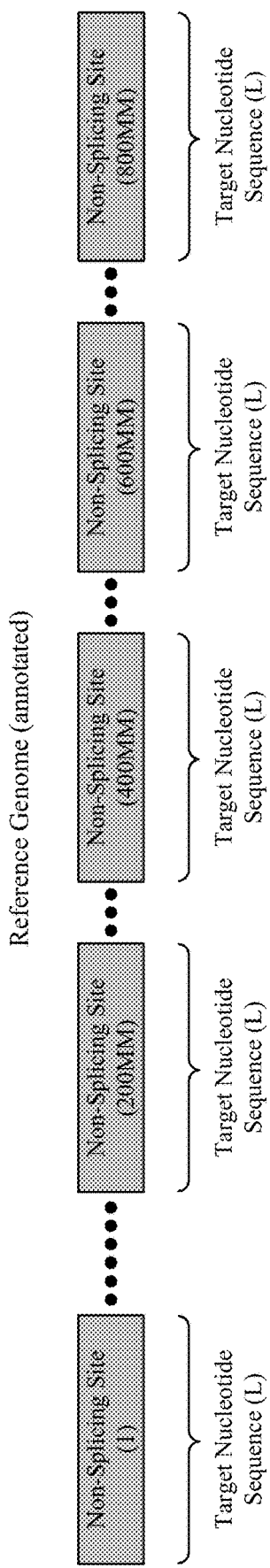
FIG. 28 shows that the ACNN can be trained on at least 800 million non-splicing sites and the CNN can be trained on at least 1 million non-splicing sites.

As shown in FIG. 28, the system can train the ACNN on 150000 training examples of donor splice sites, 150000 training examples of acceptor splice sites, and 800000000 training examples of non-splicing sites.

Figure 19:
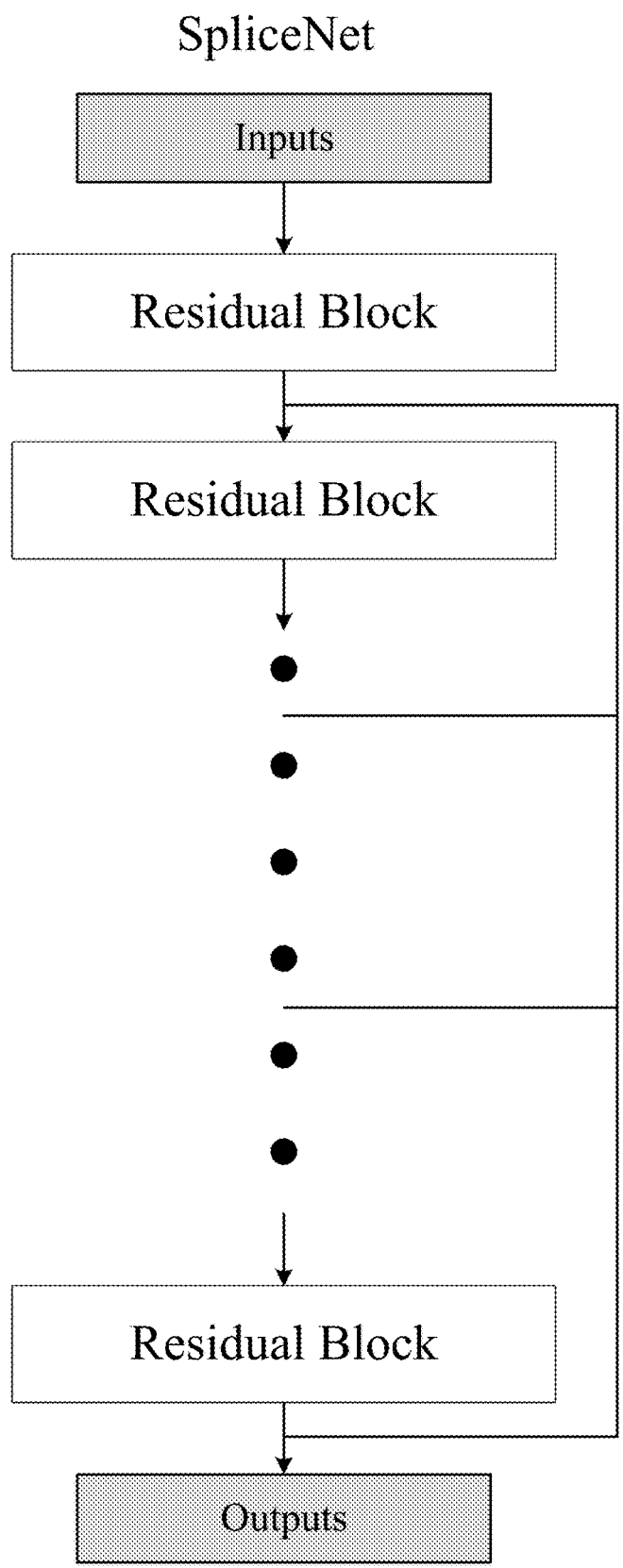
FIG. 19 depicts one implementation of the architecture of an atrous convolutional neural network (abbreviated ACNN), referred to herein as "SpliceNet".

As shown in FIG. 19, the ACNN can comprise groups of residual blocks arranged in a sequence from lowest to highest. Each group of residual blocks is parameterized by a number of convolution filters in the residual blocks, a convolution window size of the residual blocks, and an atrous convolution rate of the residual blocks.

As shown in FIGS. 21, 22, 23, and 24, in the ACNN, the atrous convolution rate progresses non-exponentially from a lower residual block group to a higher residual block group.

As shown in FIGS. 21, 22, 23, and 24, in the ACNN, the convolution window size varies between groups of residual blocks.

Figure 21:
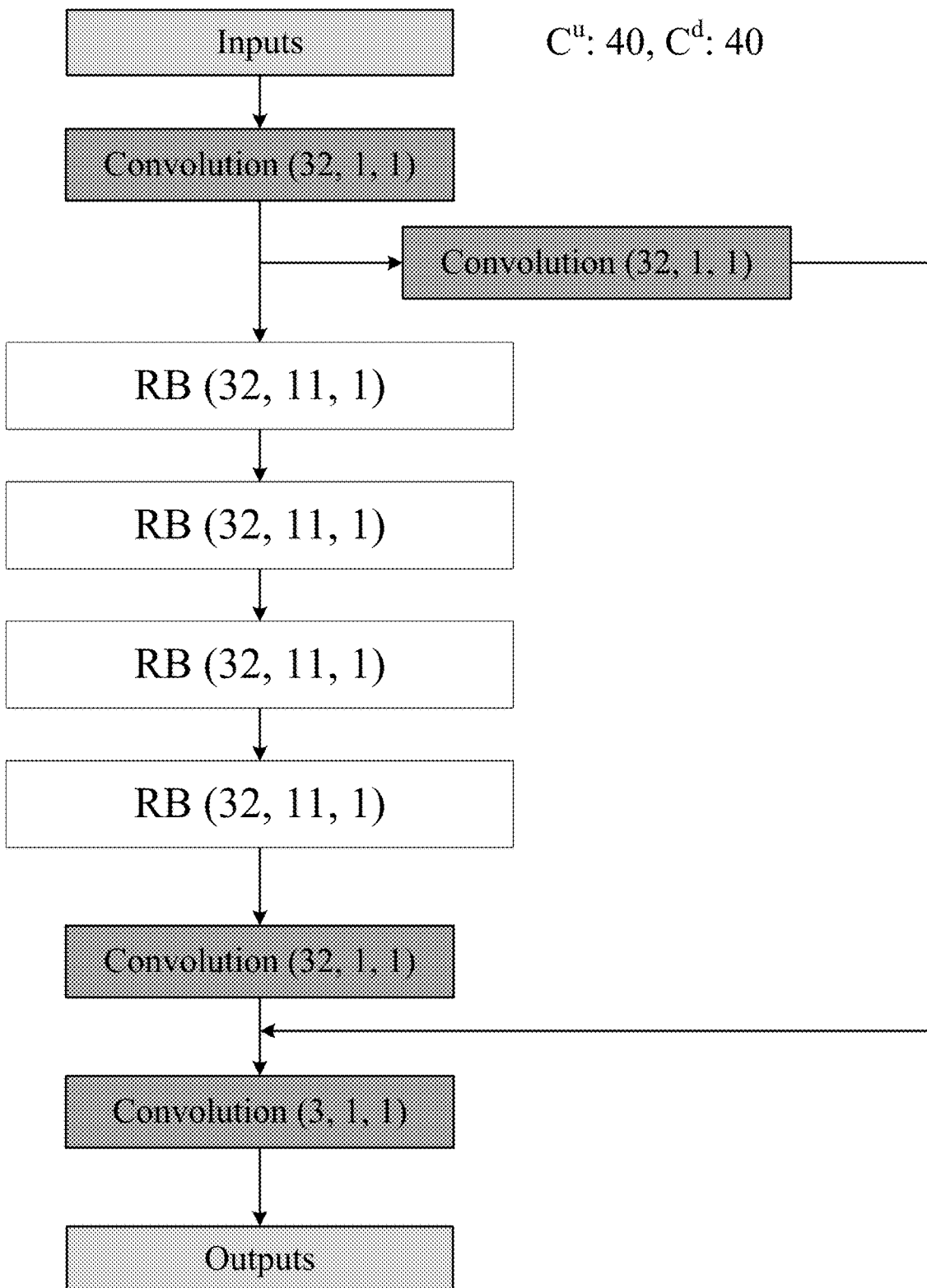
FIG. 21 depicts another implementation of the architecture of the ACNN, referred to herein as "SpliceNet80".

The ACNN can be configured to evaluate an input that comprises a target nucleotide sequence further flanked by 40 upstream context nucleotides and 40 downstream context nucleotides. In such an implementation, the ACNN includes one group of four residual blocks and at least one skip connection. Each residual block has 32 convolution filters, 11 convolution window size, and 1 atrous convolution rate. This implementation of the ACNN is referred to herein as "SpliceNet80" and is shown in FIG. 21.

Figure 22:
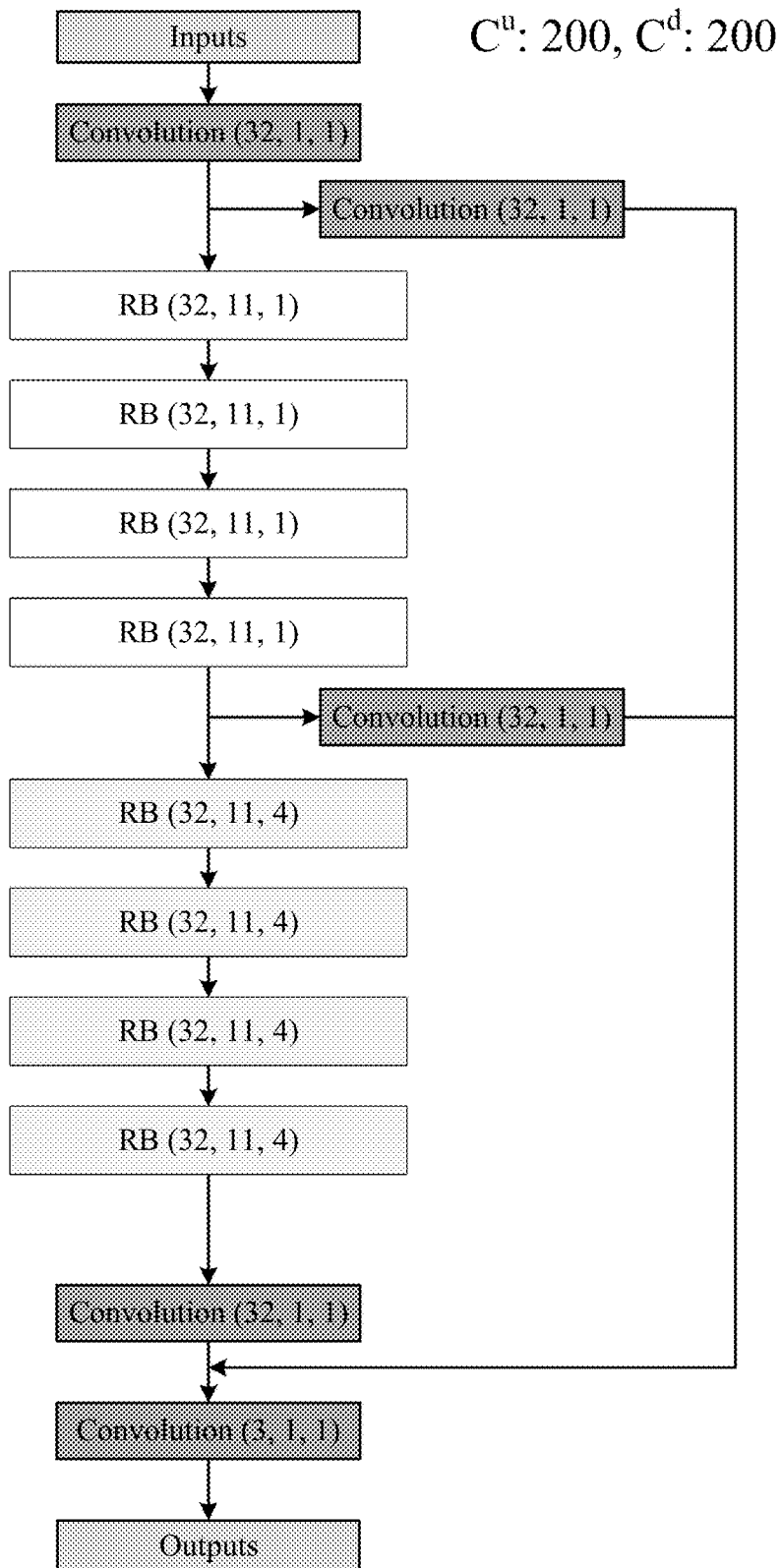
FIG. 22 depicts yet another implementation of the architecture of the ACNN, referred to herein as "SpliceNet400".

The ACNN can be configured to evaluate an input that comprises the target nucleotide sequence further flanked by 200 upstream context nucleotides and 200 downstream context nucleotides. In such an implementation, the ACNN includes at least two groups of four residual blocks and at least two skip connections. Each residual block in a first group has 32 convolution filters, 11 convolution window size, and 1 atrous convolution rate. Each residual block in a second group has 32 convolution filters, 11 convolution window size, and 4 atrous convolution rate. This implementation of the ACNN is referred to herein as "SpliceNet400" and is shown in FIG. 22.

Figure 23:
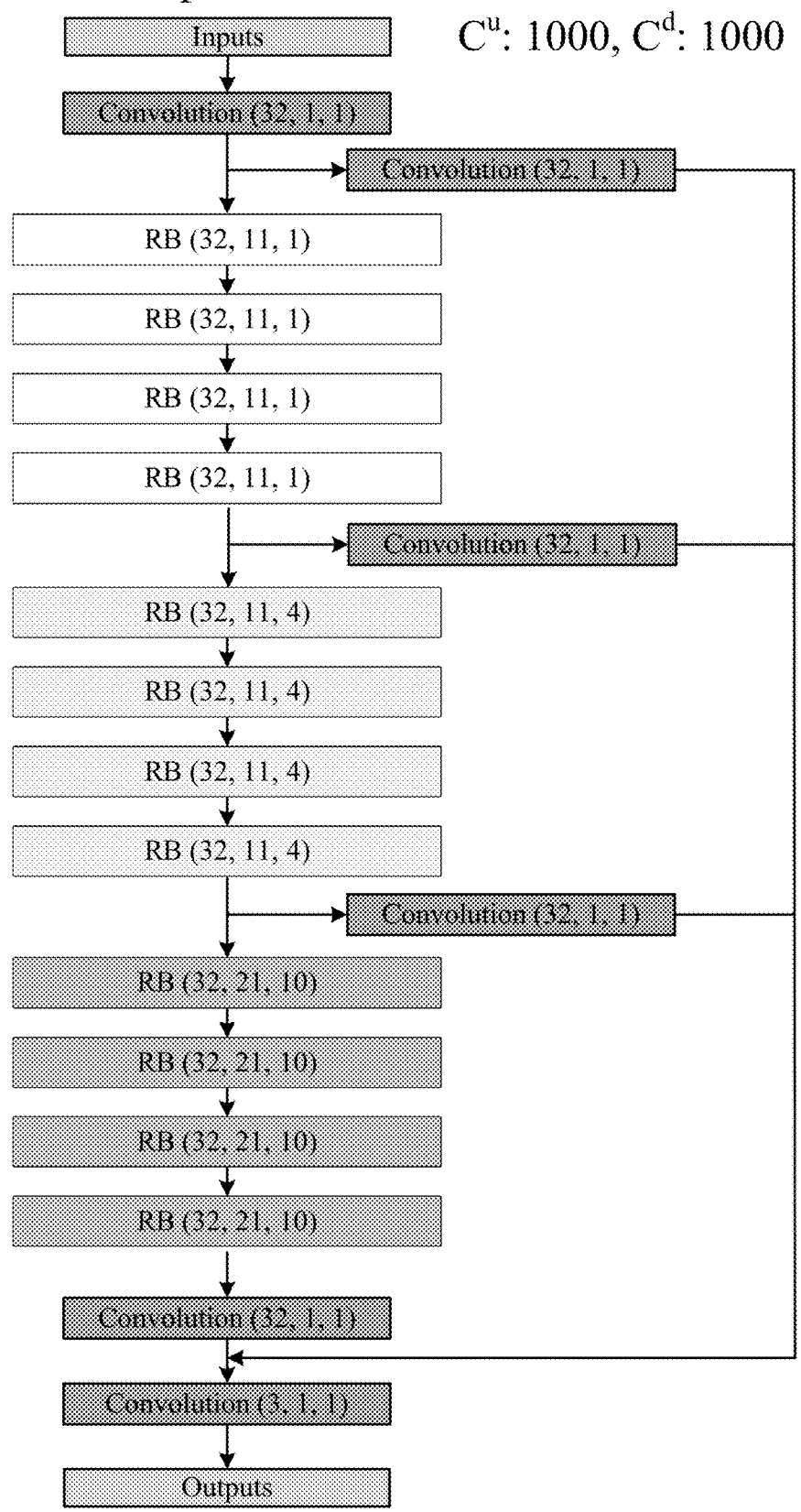
FIG. 23 depicts yet further implementation of the architecture of the ACNN, referred to herein as "SpliceNet2000".

The ACNN can be configured to evaluate an input that comprises a target nucleotide sequence further flanked by 1000 upstream context nucleotides and 1000 downstream context nucleotides. In such an implementation, the ACNN includes at least three groups of four residual blocks and at least three skip connections. Each residual block in a first group has 32 convolution filters, 11 convolution window size, and 1 atrous convolution rate. Each residual block in a second group has 32 convolution filters, 11 convolution window size, and 4 atrous convolution rate. Each residual block in a third group has 32 convolution filters, 21 convolution window size, and 19 atrous convolution rate. This implementation of the ACNN is referred to herein as "SpliceNet2000" and is shown in FIG. 23.

Figure 24:
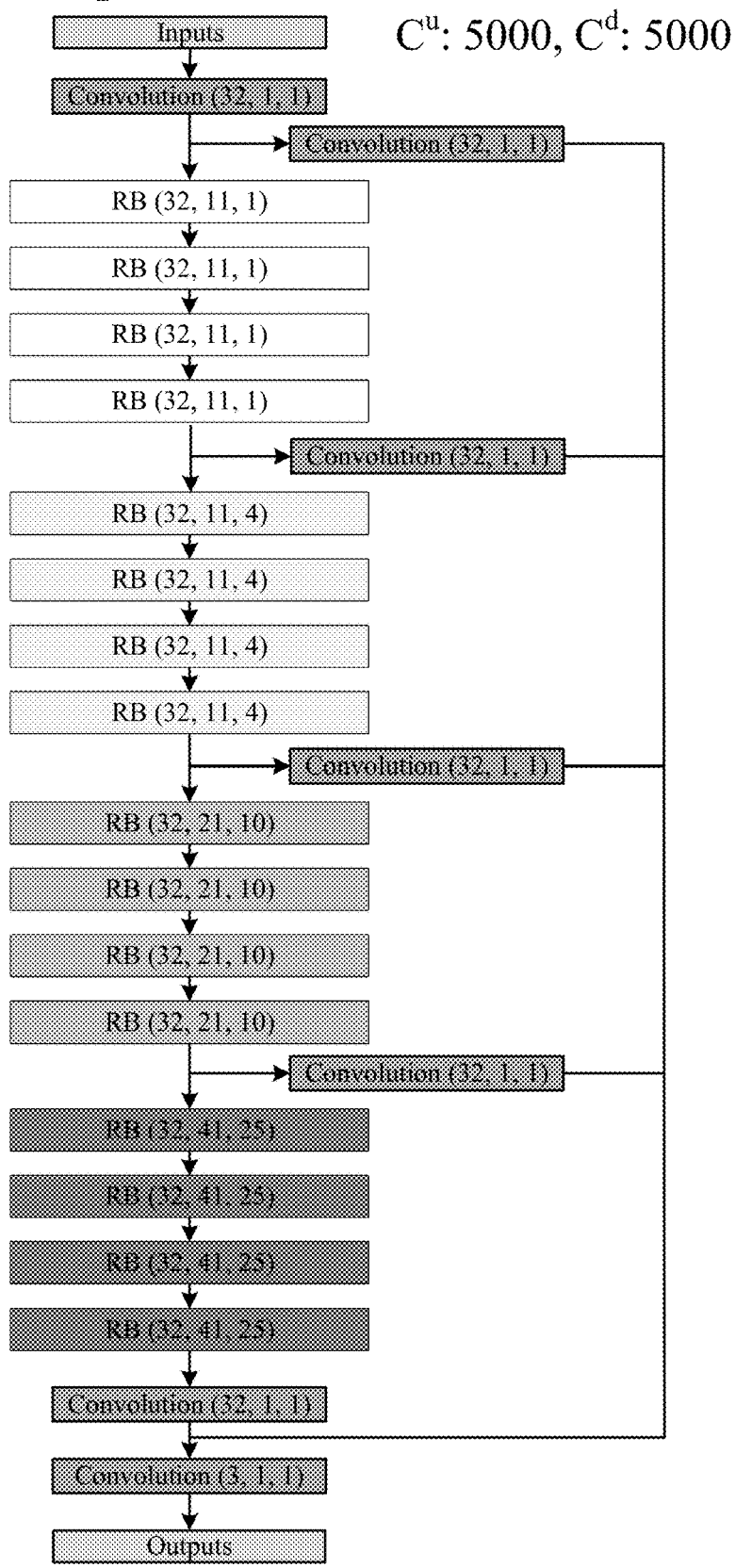
FIG. 24 depicts yet another implementation of the architecture of the ACNN, referred to herein as "SpliceNet10000".

The ACNN can be configured to evaluate an input that comprises a target nucleotide sequence further flanked by 5000 upstream context nucleotides and 5000 downstream context nucleotides. In such an implementation, the ACNN includes at least four groups of four residual blocks and at least four skip connections. Each residual block in a first group has 32 convolution filters, 11 convolution window size, and 1 atrous convolution rate. Each residual block in a second group has 32 convolution filters, 11 convolution window size, and 4 atrous convolution rate. Each residual block in a third group has 32 convolution filters, 21 convolution window size, and 19 atrous convolution rate. Each residual block in a fourth group has 32 convolution filters, 41 convolution window size, and 25 atrous convolution rate. This implementation of the ACNN is referred to herein as "SpliceNet10000" and is shown in FIG. 24.

The triplet scores for each nucleotide in the target nucleotide sequence can be exponentially normalized to sum to unity. In such an implementation, the system classifies each nucleotide in the target nucleotide as the donor splice site, the acceptor splice site, or the non-splicing site based on a highest score in the respective triplet scores.

Figure 35:
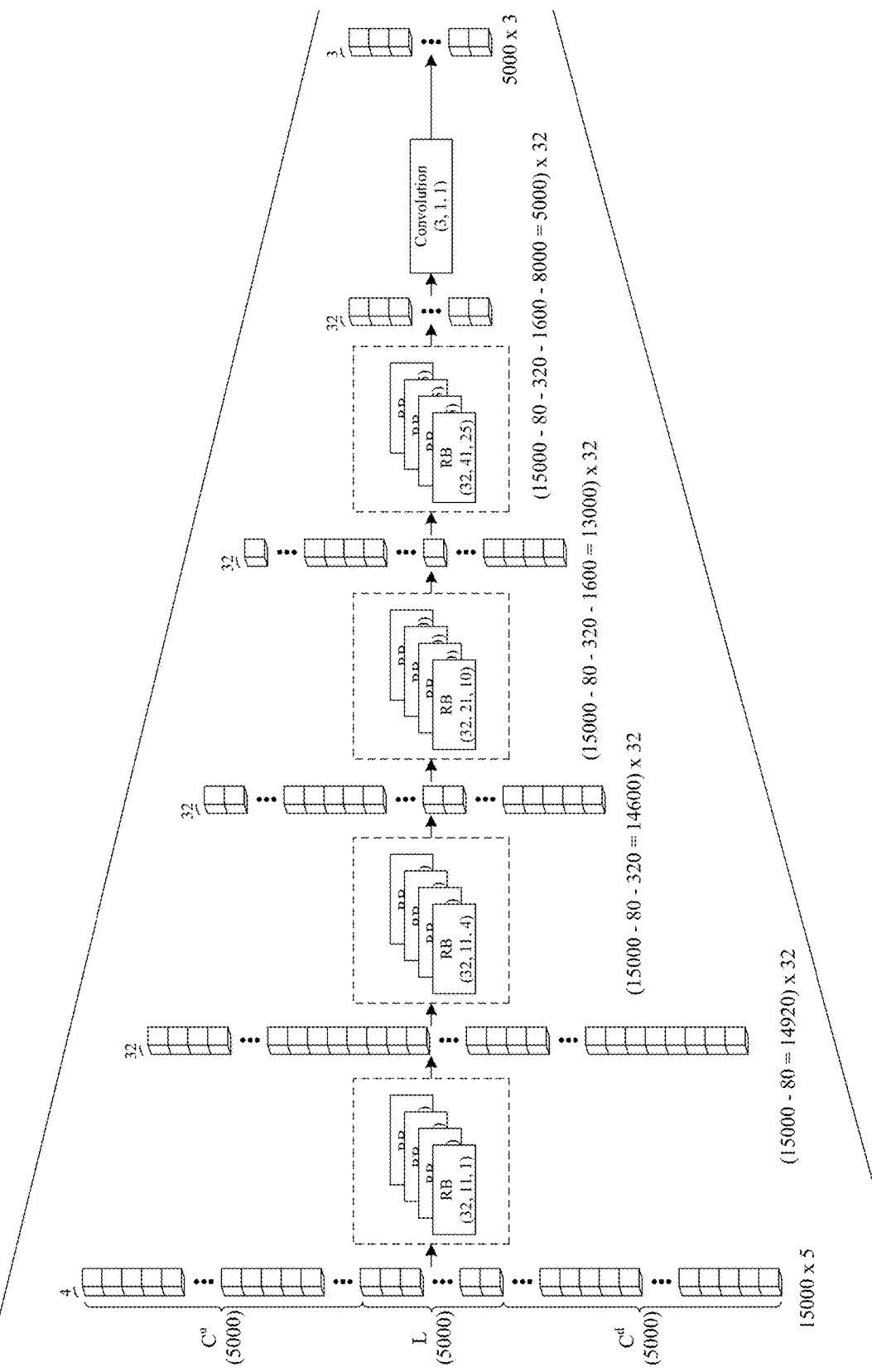
FIG. 35 illustrates processing pyramid of SpliceNet10000 for splice site classification.

As shown in FIG. 35, dimensionality of the ACNN's input can be defined as $(C^u+L+C^d)\times 4$, where $C^u$ is a number of upstream context nucleotides, $C^d$ is a number of downstream context nucleotides, and L is a number of nucleotides in the target nucleotide sequence. In one implementation, the dimensionality of the input is $(5000+5000+5000)\times 4$.

As shown in FIG. 35, dimensionality of the ACNN's output can be defined as $L\times 3$. In one implementation, the dimensionality of the output is $5000\times 3$.

As shown in FIG. 35, each group of residual blocks can produce an intermediate output by processing a preceding input. Dimensionality of the intermediate output can be defined as $(I-[\{(W-1)*D\}*A])\times N$, where I is dimensionality of the preceding input, W is convolution window size of the residual blocks, D is atrous convolution rate of the residual blocks, A is a number of atrous convolution layers in the group, and N is a number of convolution filters in the residual blocks.

Figure 32:
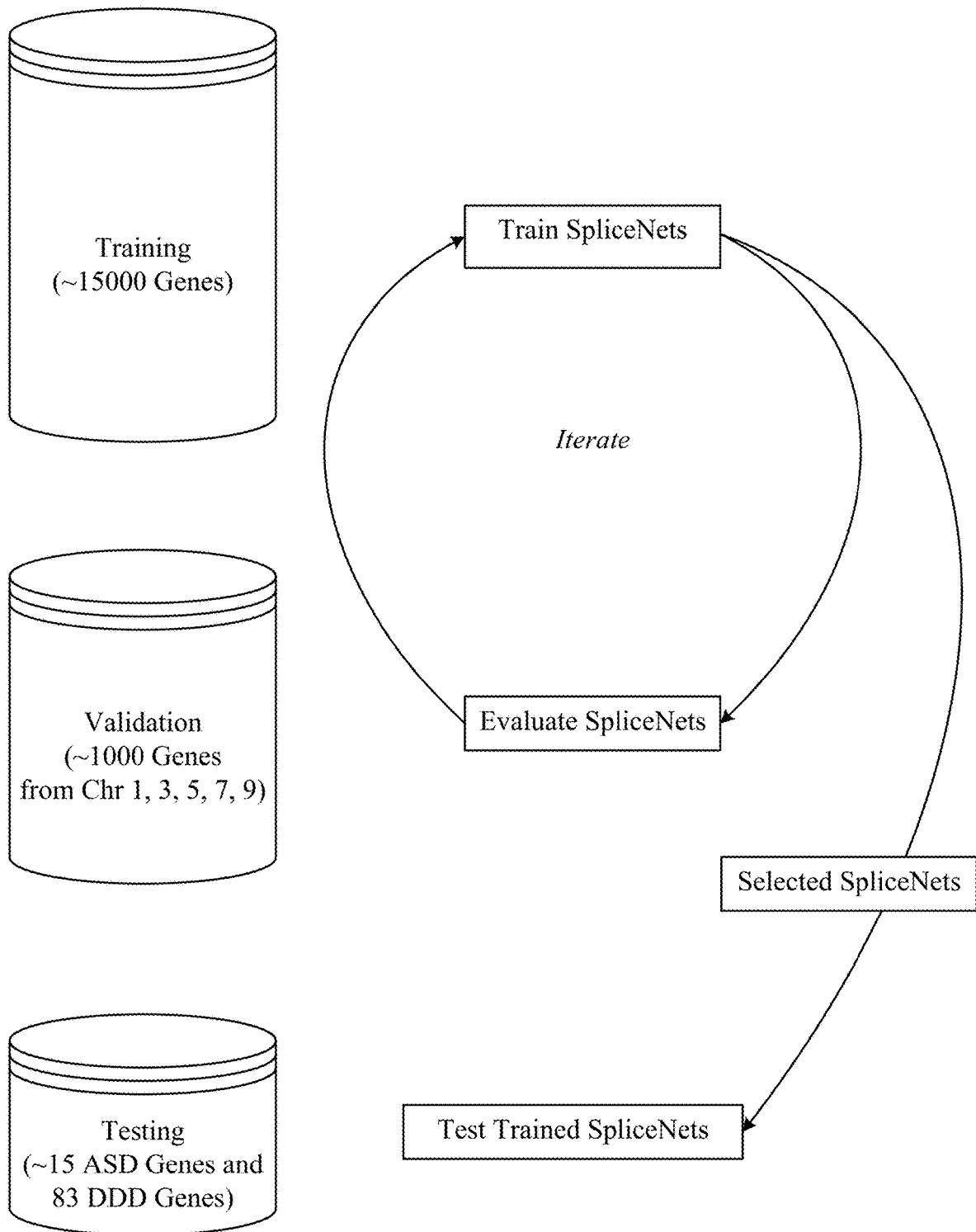
FIG. 32 shows training, validation, and testing of the ACNN and the CNN.

As shown in FIG. 32, ACNN batch-wise evaluates the training examples during an epoch. The training examples are randomly sampled into batches. Each batch has a predetermined batch size. The ACNN iterates evaluation of the training examples over a plurality of epochs (e.g., 1-10).

The input can comprise a target nucleotide sequence that has two adjacent target nucleotides. The two adjacent target nucleotides can be adenine (abbreviated A) and guanine (abbreviated G). The two adjacent target nucleotides can be guanine (abbreviated G) and uracil (abbreviated U).

The system includes a one-hot encoder (shown in FIG. 29) that sparsely encodes the training examples and provides one-hot encodings as input.

The ACNN can be parameterized by a number of residual blocks, a number of skip connections, and a number of residual connections.

The ACNN can comprise dimensionality altering convolution layers that reshape spatial and feature dimensions of a preceding input.

Figure 20:
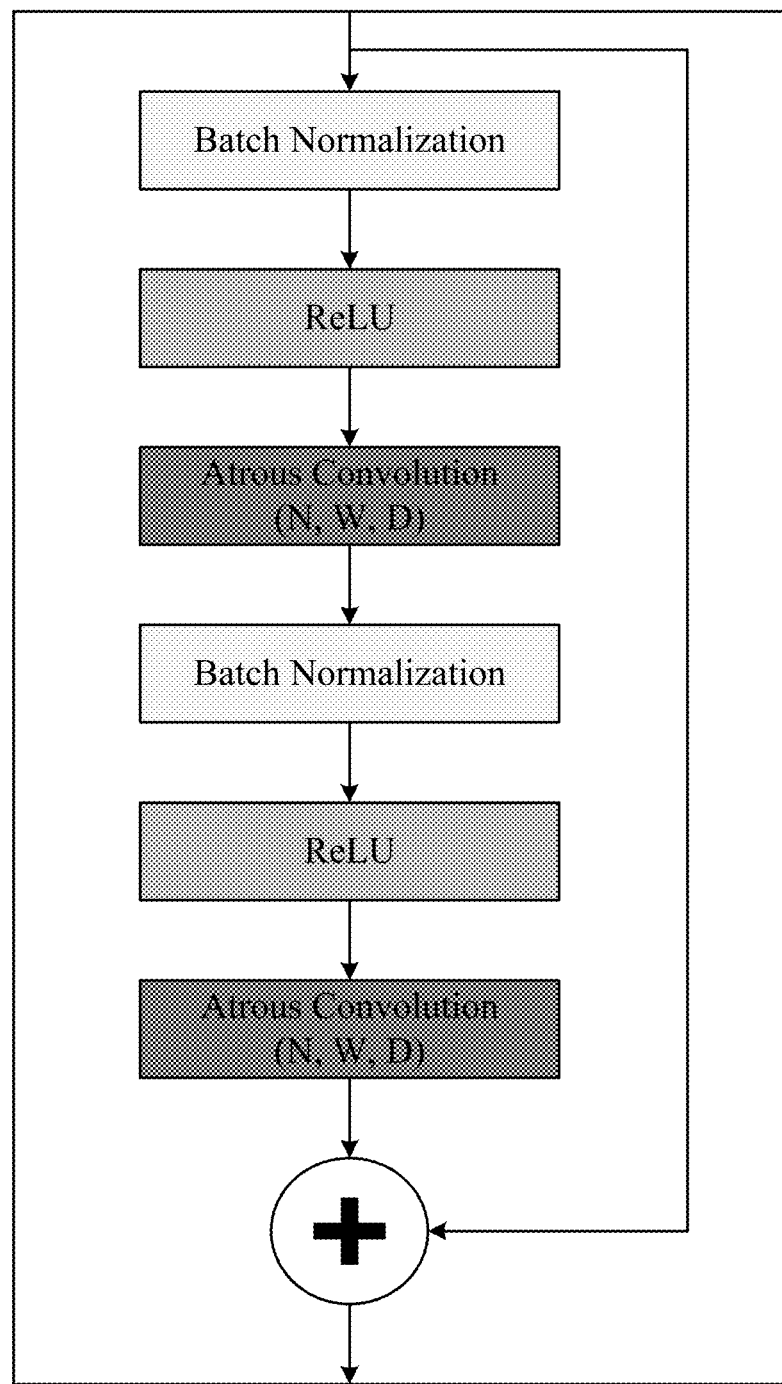
FIG. 20 shows one implementation of a residual block that can used by the ACNN and a convolutional neural network (abbreviated CNN).

As shown in FIG. 20, each residual block can comprise at least one batch normalization layer, at least one rectified linear unit (abbreviated ReLU) layer, at least one atrous convolution layer, and at least one residual connection. In such an implementation, each residual block comprises two batch normalization layers, two ReLU non-linearity layers, two atrous convolution layers, and one residual connection.

Other implementations may include a non-transitory computer readable storage medium storing instructions executable by a processor to perform actions of the system described above. Yet another implementation may include a method performing actions of the system described above.

Another system implementation of the of the technology disclosed includes a trained splice site predictor that runs on numerous processors operating in parallel and coupled to memory. The system trains an atrous convolutional neural network (abbreviated ACNN), running on the numerous processors, on at least 50000 training examples of donor splice sites, at least 50000 training examples of acceptor splice sites, and at least 100000 training examples of non-splicing sites. Each of the training examples used in the training is a nucleotide sequence that includes a target nucleotide flanked by at least 400 nucleotides on each side.

The system includes an input stage of the ACNN which runs on at least one of the numerous processors and feeds an input sequence of at least 801 nucleotides for evaluation of target nucleotides. Each target nucleotide is flanked by at least 400 nucleotides on each side.

The system includes an output stage of the ACNN which runs on at least one of the numerous processors and translates analysis by the ACNN into classification scores for likelihood that each of the target nucleotides is a donor splice site, an acceptor splice site, or a non-splicing site.

Each of the features discussed in this particular implementation section for the first system implementation apply equally to this system implementation. As indicated above, all the system features are not repeated here and should be considered repeated by reference.

The ACNN can be trained on 150000 training examples of donor splice sites, 150000 training examples of acceptor splice sites, and 800000000 training examples of non-splicing sites. In another implementation of the system, the ACNN comprises groups of residual blocks arranged in a sequence from lowest to highest. In yet another implementation of the system, each group of residual blocks is parameterized by a number of convolution filters in the residual blocks, a convolution window size of the residual blocks, and an atrous convolution rate of the residual blocks.

The ACNN can comprise groups of residual blocks arranged in a sequence from lowest to highest. Each group of residual blocks is parameterized by a number of convolution filters in the residual blocks, a convolution window size of the residual blocks, and an atrous convolution rate of the residual blocks.

In the ACNN, the atrous convolution rate progresses non-exponentially from a lower residual block group to a higher residual block group. Also in the ACNN, the convolution window size varies between groups of residual blocks.

Figure 18:
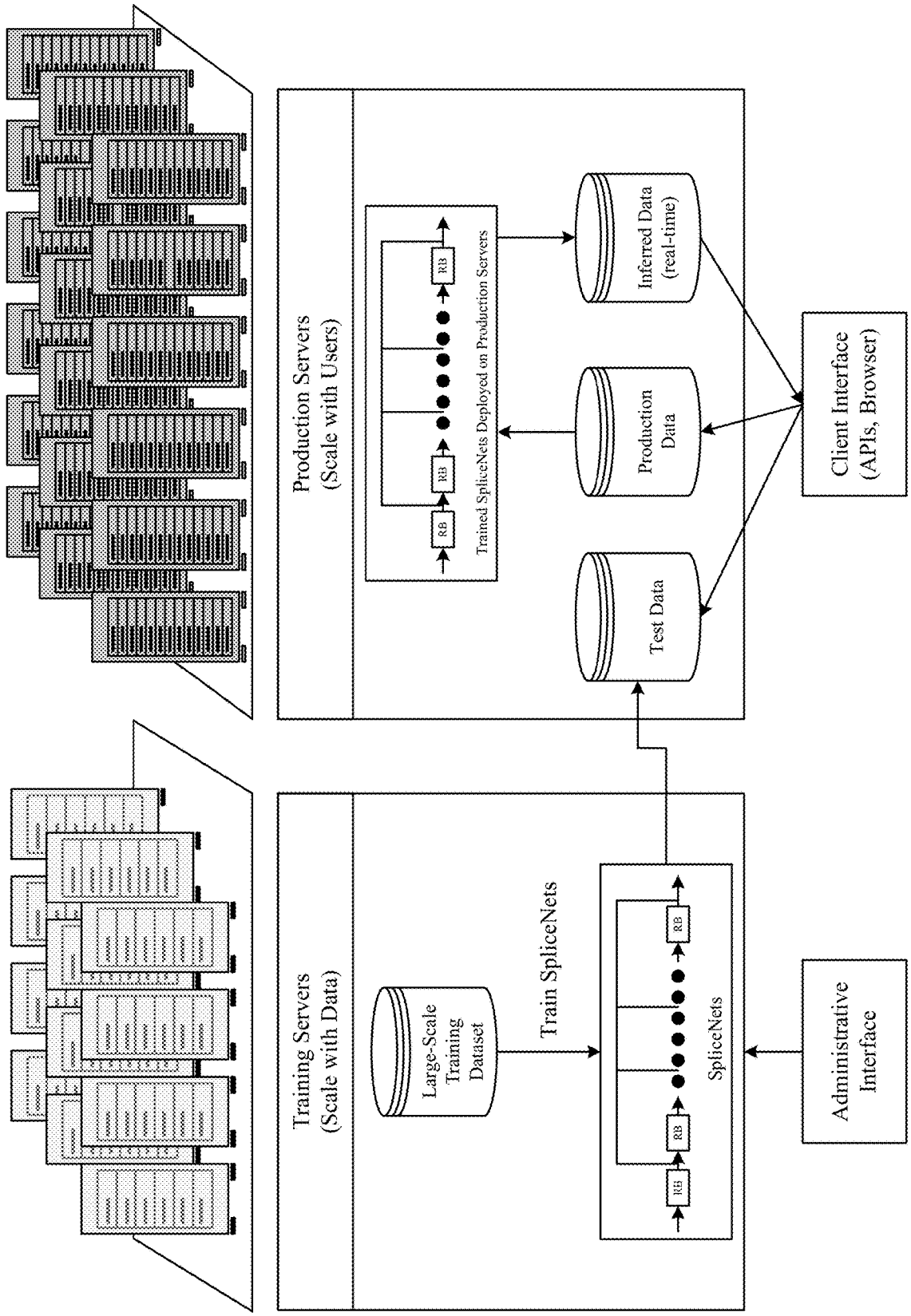
FIG. 18 illustrates one implementation of a computing environment with training servers and production servers that can be used to implement the technology disclosed.

The ACNN can be trained on one or more training servers, as shown in FIG. 18.

The trained ACNN can be deployed on one or more production servers that receive input sequences from requesting clients, as shown in FIG. 18. In such an implementation, the production servers process the input sequences through the input and output stages of the ACNN to produce outputs that are transmitted to the clients, as shown in FIG. 18.

Other implementations may include a non-transitory computer readable storage medium storing instructions executable by a processor to perform actions of the system described above. Yet another implementation may include a method performing actions of the system described above.

A method implementation of the technology disclosed includes training a splice site detector that identifies splice sites in genomic sequences (e.g., nucleotide sequences).

The method includes feeding, an atrous convolutional neural network (abbreviated ACNN), an input sequence of at least 801 nucleotides for evaluation of target nucleotides that are each flanked by at least 400 nucleotides on each side.

The ACNN is trained on at least 50000 training examples of donor splice sites, at least 50000 training examples of acceptor splice sites, and at least 100000 training examples of non-splicing sites. Each of the training examples used in the training is a nucleotide sequence that includes a target nucleotide flanked by at least 400 nucleotides on each side.

The method further includes translating analysis by the ACNN into classification scores for likelihood that each of the target nucleotides is a donor splice site, an acceptor splice site, or a non-splicing site.

Each of the features discussed in this particular implementation section for the first system implementation apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

We describe systems, methods, and articles of manufacture for using a trained atrous convolutional neural network to detect aberrant splicing in genomic sequences (e.g., nucleotide sequences). One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to the memory. The memory is loaded with computer instructions to implement an aberrant splicing detector running on numerous processors operating in parallel and coupled to memory.

Figure 34:
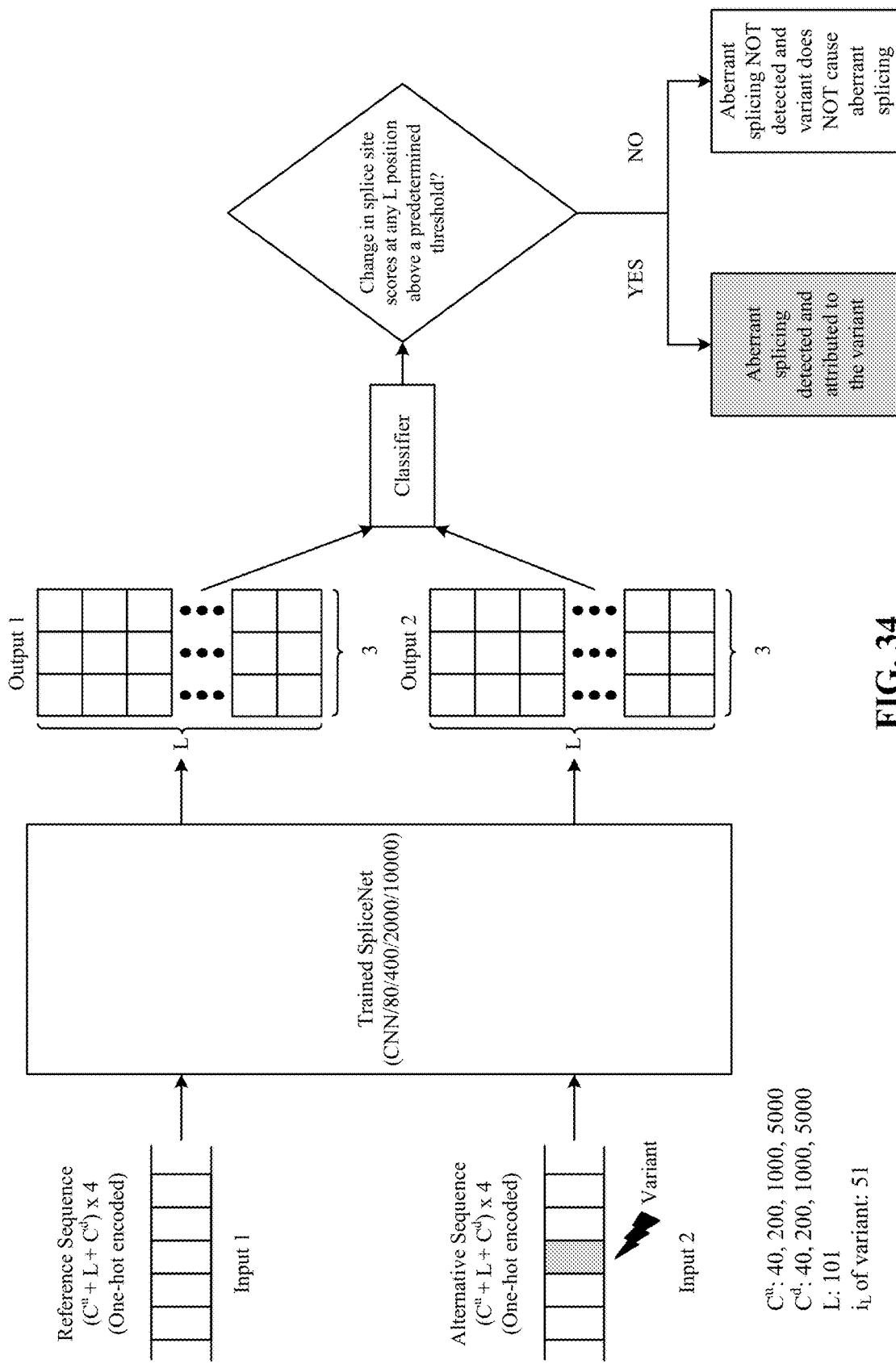
FIG. 34 illustrates aberrant splicing detection.

As shown in FIG. 34, the system includes a trained atrous convolutional neural network (abbreviated ACNN) running on the numerous processors. An ACNN is a convolutional neural network that uses atrous/dilated convolutions which allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

As shown in FIG. 34, the ACNN classifies target nucleotides in an input sequence and assigns splice site scores for likelihood that each of the target nucleotides is a donor splice site, an acceptor splice site, or a non-splicing site. The input sequence comprises at least 801 nucleotides and each target nucleotide is flanked by at least 400 nucleotides on each side.

Figure 33:
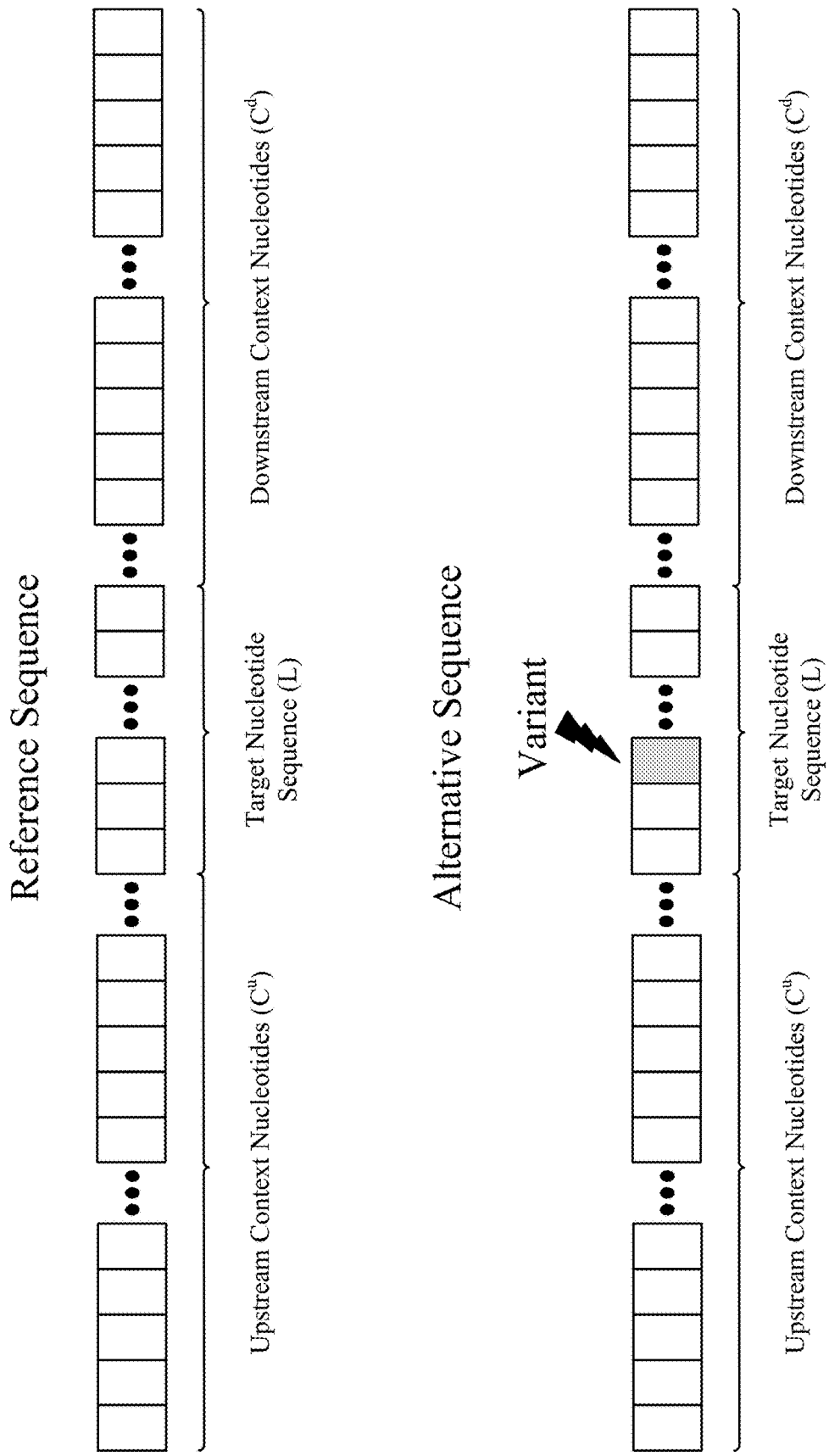
FIG. 33 depicts a reference sequence and an alternative sequence.

As shown in FIG. 34, the system also includes a classifier, running on at least one of the numerous processors, that processes a reference sequence and a variant sequence through the ACNN to produce splice site scores for a likelihood that each target nucleotide in the reference sequence and in the variant sequence is a donor splice site, an acceptor splice site, or a non-splicing site. The reference sequence and the variant sequence each have at least 101 target nucleotides and each target nucleotide is flanked by at least 400 nucleotides on each side. FIG. 33 depicts a reference sequence and an alternative/variant sequence.

As shown in FIG. 34, the system then determines, from differences in the splice site scores of the target nucleotides in the reference sequence and in the variant sequence, whether a variant that generated the variant sequence causes aberrant splicing and is therefore pathogenic.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

As shown in FIG. 34, the differences in the splice site scores can be determined position-wise between the target nucleotides in the reference sequence and in the variant sequence.

As shown in FIG. 34, for at least one target nucleotide position, when a global maximum difference in the splice site scores is above a predetermined threshold, the ACNN classifies the variant as causing aberrant splicing and therefore pathogenic.

As shown in FIG. 17, for at least one target nucleotide position, when a global maximum difference in the splice site scores is below a predetermined threshold, the ACNN classifies the variant as not causing aberrant splicing and therefore benign.

The threshold can be determined from for a plurality of candidate thresholds. This includes processing a first set of reference and variant sequence pairs generated by benign common variants to produce a first set of aberrant splicing detections, processing a second set of reference and variant sequence pairs generated by pathogenic rare variants to produce a second set of aberrant splicing detections, and selecting at least one threshold, for use by the classifier, that maximizes a count of aberrant splicing detections in the second set and minimizes a count of aberrant splicing detections in the first set.

In one implementation, the ACNN identifies variants that cause autism spectrum disorder (abbreviated ASD). In another implementation, the ACNN identifies variants that cause developmental delay disorder (abbreviated DDD).

Figure 36:
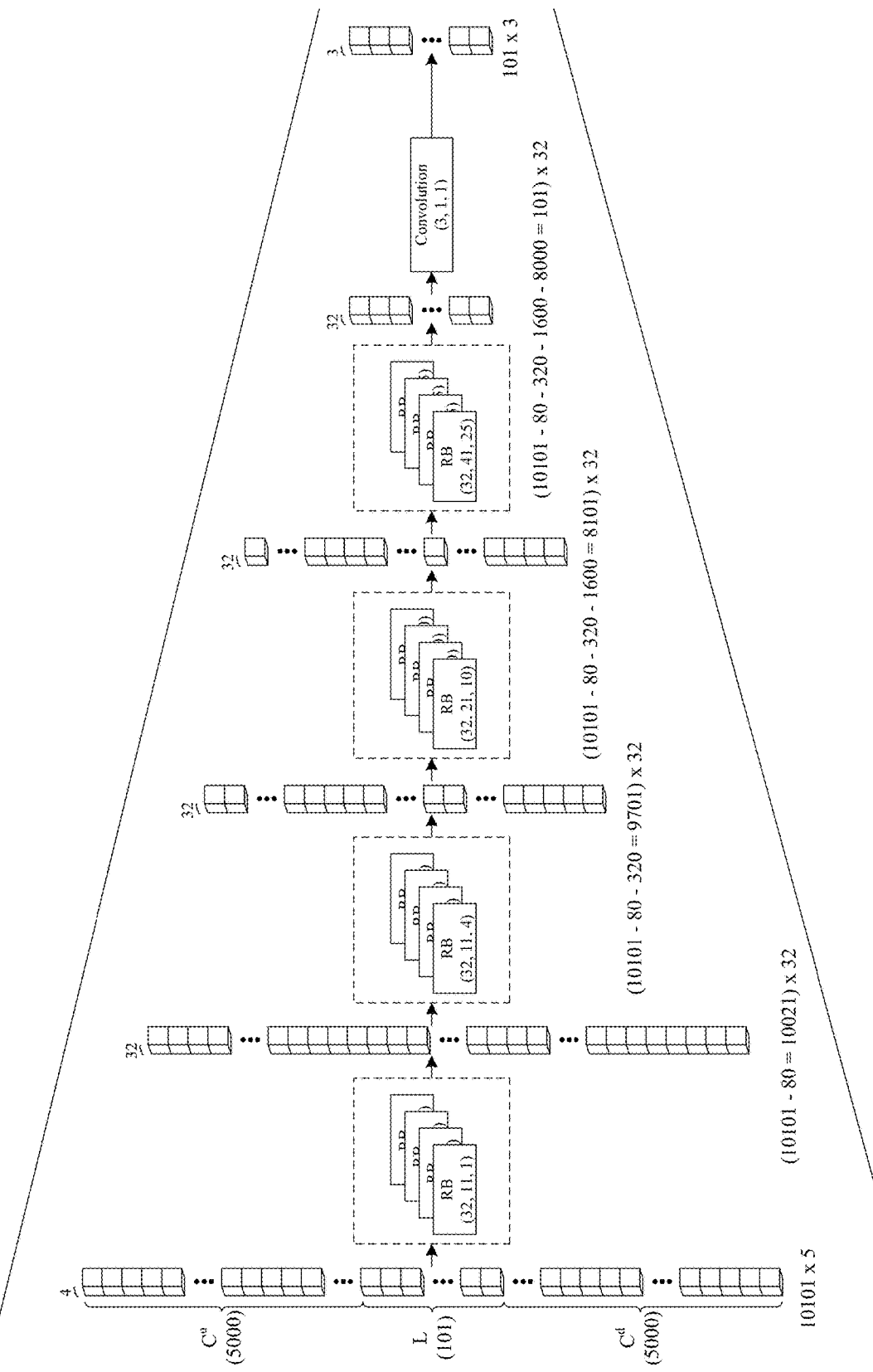
FIG. 36 depicts processing pyramid of SpliceNet10000 for aberrant splicing detection.

As shown in FIG. 36, the reference sequence and the variant sequence can each have at least 101 target nucleotides and each target nucleotide can be flanked by at least 5000 nucleotides on each side.

As shown in FIG. 36, the splice site scores of the target nucleotides in the reference sequence can be encoded in a first output of the ACNN and the splice site scores of the target nucleotides in the variant sequence can be encoded in a second output of the ACNN. In one implementation, the first output is encoded as a first 101×3 matrix and the second output is encoded as a second 101×3 matrix.

As shown in FIG. 36, in such an implementation, each row in the first 101×3 matrix uniquely represents splice site scores for a likelihood that a target nucleotide in the reference sequence is a donor splice site, an acceptor splice site, or a non-splicing site.

As shown in FIG. 36, also in such an implementation, each row in the second 101×3 matrix uniquely represents splice site scores for a likelihood that a target nucleotide in the variant sequence is a donor splice site, an acceptor splice site, or a non-splicing site.

As shown in FIG. 36, in some implementations, splice site scores in each row of the first 101×3 matrix and the second 101×3 matrix can be exponentially normalized to sum to unity.

As shown in FIG. 36, the classifier can perform a row-to-row comparison of the first 101×3 matrix and the second 101×3 matrix and determine, on a row-wise basis, changes in distribution of splice site scores. For at least one instance of the row-to-row comparison, when the change in distribution is above a predetermined threshold, the ACNN classifies the variant as causing aberrant splicing and therefore pathogenic.

The system includes a one-hot encoder (shown in FIG. 29) that sparsely encodes the reference sequence and the variant sequence.

Each of the features discussed in this particular implementation section for other system and method implementations apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a method performing actions of the system described above.

A method implementation of the technology disclosed includes detecting genomic variants that cause aberrant splicing.

The method includes processing a reference sequence through an atrous convolutional neural network (abbreviated ACNN) trained to detect differential splicing patterns in a target sub-sequence of an input sequence by classifying each nucleotide in the target sub-sequence as a donor splice site, an acceptor splice site, or a non-splicing site.

The method includes, based on the processing, detecting a first differential splicing pattern in a reference target sub-sequence by classifying each nucleotide in the reference target sub-sequence as a donor splice site, an acceptor splice site, or a non-splicing site.

The method includes processing a variant sequence through the ACNN. The variant sequence and the reference sequence differ by at least one variant nucleotide located in a variant target sub-sequence.

The method includes, based on the processing, detecting a second differential splicing pattern in the variant target sub-sequence by classifying each nucleotide in the variant target sub-sequence as a donor splice site, an acceptor splice site, or a non-splicing site.

The method includes determining a difference between the first differential splicing pattern and the second differential splicing pattern by comparing, on a nucleotide-by-nucleotide basis, splice site classifications of the reference target sub-sequence and the variant target sub-sequence.

When the difference is above a predetermined threshold, the method includes classifying the variant as causing aberrant splicing and therefore pathogenic and storing the classification in memory.

Each of the features discussed in this particular implementation section for other system and method implementations apply equally to this method implementation. As indicated above, all the system features are not repeated here and should be considered repeated by reference.

A differential splicing pattern can identify positional distribution of occurrence of splicing events in a target sub-sequence. Examples of splicing events include at least one of cryptic splicing, exon skipping, mutually exclusive exons, alternative donor site, alternative acceptor site, and intron retention.

The reference target sub-sequence and the variant target sub-sequence can be aligned with respect to nucleotide positions and can differ by the at least one variant nucleotide.

The reference target sub-sequence and the variant target sub-sequence can each have at least 40 nucleotides and can each be flanked by at least 40 nucleotides on each side.

The reference target sub-sequence and the variant target sub-sequence can each have at least 101 nucleotides and can each be flanked by at least 5000 nucleotides on each side.

The variant target sub-sequence can include two variants.

Other implementations may include a non-transitory computer readable storage medium storing instructions executable by a processor to perform the method described above. Yet another implementation may include a system including memory and one or more processors operable to execute instructions, stored in the memory, to perform the method described above.

We describe systems, methods, and articles of manufacture for using a trained convolutional neural network to detect splice sites and aberrant splicing in genomic sequences (e.g., nucleotide sequences). One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to the memory. The memory is loaded with computer instructions to train a splice site detector that identifies splice sites in genomic sequences (e.g., nucleotide sequences).

The system trains a convolutional neural network (abbreviated CNN) on at least 50000 training examples of donor splice sites, at least 50000 training examples of acceptor splice sites, and at least 100000 training examples of non-splicing sites. Each training example is a target nucleotide sequence having at least one target nucleotide flanked by at least 20 nucleotides on each side.

For evaluating a training example using the CNN, the system provides, as input to the CNN, a target nucleotide sequence further flanked by at least 40 upstream context nucleotides and at least 40 downstream context nucleotides.

Based on the evaluation, the CNN then produces, as output, triplet scores for likelihood that each nucleotide in the target nucleotide sequence is a donor splice site, an acceptor splice site, or a non-splicing site.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The input can comprise a target nucleotide sequence that has a target nucleotide flanked by 100 nucleotides on each side. In such an implementation, the target nucleotide sequence is further flanked by 200 upstream context nucleotides and 200 downstream context nucleotides.

As shown in FIG. 28, the system can train the CNN on 150000 training examples of donor splice sites, 150000 training examples of acceptor splice sites, and 1000000 training examples of non-splicing sites.

Figure 31:
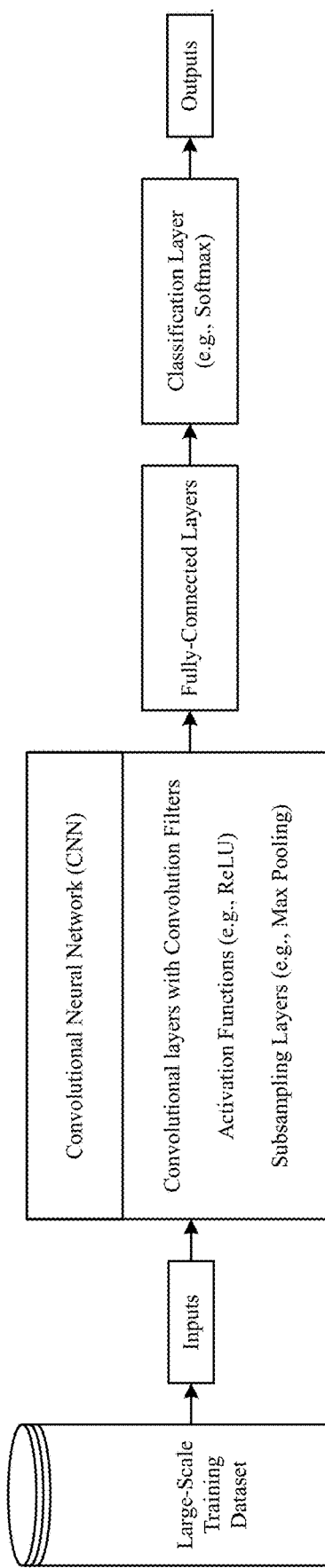
FIG. 31 shows a CNN.

As shown in FIG. 31, the CNN can be parameterized by a number of convolution layers, a number of convolution filters, and a number of subsampling layers (e.g., max pooling and average pooling).

As shown in FIG. 31, the CNN can include one or more fully-connected layers and a terminal classification layer.

The CNN can comprise dimensionality altering convolution layers that reshape spatial and feature dimensions of a preceding input.

The triplet scores for each nucleotide in the target nucleotide sequence can be exponentially normalized to sum to unity. In such an implementation, the system classifies each nucleotide in the target nucleotide as the donor splice site, the acceptor splice site, or the non-splicing site based on a highest score in the respective triplet scores.

As shown in FIG. 32, CNN batch-wise evaluates the training examples during an epoch. The training examples are randomly sampled into batches. Each batch has a predetermined batch size. The CNN iterates evaluation of the training examples over a plurality of epochs (e.g., 1-10).

The input can comprise a target nucleotide sequence that has two adjacent target nucleotides. The two adjacent target nucleotides can be adenine (abbreviated A) and guanine (abbreviated G). The two adjacent target nucleotides can be guanine (abbreviated G) and uracil (abbreviated U).

The system includes a one-hot encoder (shown in FIG. 32) that sparsely encodes the training examples and provides one-hot encodings as input.

The CNN can be parameterized by a number of residual blocks, a number of skip connections, and a number of residual connections.

Each residual block can comprise at least one batch normalization layer, at least one rectified linear unit (abbreviated ReLU) layer, at least one dimensionality altering layer, and at least one residual connection. Each residual block can comprise two batch normalization layers, two ReLU non-linearity layers, two dimensionality altering layers, and one residual connection.

Each of the features discussed in this particular implementation section for other system and method implementations apply equally to this system implementation. As indicated above, all the system features are not repeated here and should be considered repeated by reference.

Other implementations may include a non-transitory computer readable storage medium storing instructions executable by a processor to perform actions of the system described above. Yet another implementation may include a method performing actions of the system described above.

Another system implementation of the of the technology disclosed includes a trained splice site predictor that runs on numerous processors operating in parallel and coupled to memory. The system trains a convolutional neural network (abbreviated CNN), running on the numerous processors, on at least 50000 training examples of donor splice sites, at least 50000 training examples of acceptor splice sites, and at least 100000 training examples of non-splicing sites. Each of the training examples used in the training is a nucleotide sequence that includes a target nucleotide flanked by at least 400 nucleotides on each side.

The system includes an input stage of the CNN which runs on at least one of the numerous processors and feeds an input sequence of at least 801 nucleotides for evaluation of target nucleotides. Each target nucleotide is flanked by at least 400 nucleotides on each side.

The system includes an output stage of the CNN which runs on at least one of the numerous processors and translates analysis by the CNN into classification scores for likelihood that each of the target nucleotides is a donor splice site, an acceptor splice site, or a non-splicing site.

Each of the features discussed in this particular implementation section for other system and method implementations apply equally to this system implementation. As indicated above, all the system features are not repeated here and should be considered repeated by reference.

The CNN can be trained on 150000 training examples of donor splice sites, 150000 training examples of acceptor splice sites, and 800000000 training examples of non-splicing sites.

The CNN can be trained on one or more training servers.

The trained CNN can be deployed on one or more production servers that receive input sequences from requesting clients. In such an implementation, the production servers process the input sequences through the input and output stages of the CNN to produce outputs that are transmitted to the clients.

Other implementations may include a non-transitory computer readable storage medium storing instructions executable by a processor to perform actions of the system described above. Yet another implementation may include a method performing actions of the system described above.

A method implementation of the technology disclosed includes training a splice site detector that identifies splice sites in genomic sequences (e.g., nucleotide sequences). The method includes feeding, a convolutional neural network (abbreviated CNN), an input sequence of at least 801 nucleotides for evaluation of target nucleotides that are each flanked by at least 400 nucleotides on each side.

The CNN is trained on at least 50000 training examples of donor splice sites, at least 50000 training examples of acceptor splice sites, and at least 100000 training examples of non-splicing sites. Each of the training examples used in the training is a nucleotide sequence that includes a target nucleotide flanked by at least 400 nucleotides on each side.

The method further includes translating analysis by the CNN into classification scores for likelihood that each of the target nucleotides is a donor splice site, an acceptor splice site, or a non-splicing site.

Each of the features discussed in this particular implementation section for other system and method implementations apply equally to this method implementation. As indicated above, all the system features are not repeated here and should be considered repeated by reference.

Other implementations may include a non-transitory computer readable storage medium storing instructions executable by a processor to perform the method described above. Yet another implementation may include a system including memory and one or more processors operable to execute instructions, stored in the memory, to perform the method described above.

Yet another system implementation of the technology disclosed includes one or more processors coupled to the memory. The memory is loaded with computer instructions to implement an aberrant splicing detector running on numerous processors operating in parallel and coupled to memory.

The system includes a trained convolutional neural network (abbreviated CNN) running on the numerous processors.

As shown in FIG. 34, the CNN classifies target nucleotides in an input sequence and assigns splice site scores for likelihood that each of the target nucleotides is a donor splice site, an acceptor splice site, or a non-splicing site. The input sequence comprises at least 801 nucleotides and each target nucleotide is flanked by at least 400 nucleotides on each side.

As shown in FIG. 34, the system also includes a classifier, running on at least one of the numerous processors, that processes a reference sequence and a variant sequence through the CNN to produce splice site scores for a likelihood that each target nucleotide in the reference sequence and in the variant sequence is a donor splice site, an acceptor splice site, or a non-splicing site. The reference sequence and the variant sequence each have at least 101 target nucleotides and each target nucleotide is flanked by at least 400 nucleotides on each side.

As shown in FIG. 34, the system then determines, from differences in the splice site scores of the target nucleotides in the reference sequence and in the variant sequence, whether a variant that generated the variant sequence causes aberrant splicing and is therefore pathogenic.

Each of the features discussed in this particular implementation section for other system and method implementations apply equally to this system implementation. As indicated above, all the system features are not repeated here and should be considered repeated by reference.

The differences in the splice site scores can be determined position-wise between the target nucleotides in the reference sequence and in the variant sequence.

For at least one target nucleotide position, when a global maximum difference in the splice site scores is above a predetermined threshold, the CNN classifies the variant as causing aberrant splicing and therefore pathogenic.

For at least one target nucleotide position, when a global maximum difference in the splice site scores is below a predetermined threshold, the CNN classifies the variant as not causing aberrant splicing and therefore benign.

The threshold can be determined from for a plurality of candidate thresholds. This includes processing a first set of reference and variant sequence pairs generated by benign common variants to produce a first set of aberrant splicing detections, processing a second set of reference and variant sequence pairs generated by pathogenic rare variants to produce a second set of aberrant splicing detections, and selecting at least one threshold, for use by the classifier, that maximizes a count of aberrant splicing detections in the second set and minimizes a count of aberrant splicing detections in the first set.

In one implementation, the CNN identifies variants that cause autism spectrum disorder (abbreviated ASD). In another implementation, the CNN identifies variants that cause developmental delay disorder (abbreviated DDD).

The reference sequence and the variant sequence can each have at least 101 target nucleotides and each target nucleotide can be flanked by at least 1000 nucleotides on each side.

The splice site scores of the target nucleotides in the reference sequence can be encoded in a first output of the CNN and the splice site scores of the target nucleotides in the variant sequence can be encoded in a second output of the CNN. In one implementation, the first output is encoded as a first 101×3 matrix and the second output is encoded as a second 101×3 matrix.

In such an implementation, each row in the first 101×3 matrix uniquely represents splice site scores for a likelihood that a target nucleotide in the reference sequence is a donor splice site, an acceptor splice site, or a non-splicing site.

Also in such an implementation, each row in the second 101×3 matrix uniquely represents splice site scores for a likelihood that a target nucleotide in the variant sequence is a donor splice site, an acceptor splice site, or a non-splicing site.

In some implementations, splice site scores in each row of the first 101×3 matrix and the second 101×3 matrix can be exponentially normalized to sum to unity.

The classifier can perform a row-to-row comparison of the first 101×3 matrix and the second 101×3 matrix and determine, on a row-wise basis, changes in distribution of splice site scores. For at least one instance of the row-to-row comparison, when the change in distribution is above a predetermined threshold, the CNN classifies the variant as causing aberrant splicing and therefore pathogenic.

The system includes a one-hot encoder (shown in FIG. 29) that sparsely encodes the reference sequence and the variant sequence.

Other implementations may include a non-transitory computer readable storage medium storing instructions executable by a processor to perform actions of the system described above. Yet another implementation may include a method performing actions of the system described above.

A method implementation of the technology disclosed includes detecting genomic variants that cause aberrant splicing.

The method includes processing a reference sequence through an atrous convolutional neural network (abbreviated CNN) trained to detect differential splicing patterns in a target sub-sequence of an input sequence by classifying each nucleotide in the target sub-sequence as a donor splice site, an acceptor splice site, or a non-splicing site.

The method includes, based on the processing, detecting a first differential splicing pattern in a reference target sub-sequence by classifying each nucleotide in the reference target sub-sequence as a donor splice site, an acceptor splice site, or a non-splicing site.

The method includes processing a variant sequence through the CNN. The variant sequence and the reference sequence differ by at least one variant nucleotide located in a variant target sub-sequence.

The method includes, based on the processing, detecting a second differential splicing pattern in the variant target sub-sequence by classifying each nucleotide in the variant target sub-sequence as a donor splice site, an acceptor splice site, or a non-splicing site.

The method includes determining a difference between the first differential splicing pattern and the second differential splicing pattern by comparing, on a nucleotide-by-nucleotide basis, splice site classifications of the reference target sub-sequence and the variant target sub-sequence.

When the difference is above a predetermined threshold, the method includes classifying the variant as causing aberrant splicing and therefore pathogenic and storing the classification in memory.

Each of the features discussed in this particular implementation section for other system and method implementations apply equally to this method implementation. As indicated above, all the system features are not repeated here and should be considered repeated by reference.

A differential splicing pattern can identify positional distribution of occurrence of splicing events in a target sub-sequence. Examples of splicing events include at least one of cryptic splicing, exon skipping, mutually exclusive exons, alternative donor site, alternative acceptor site, and intron retention.

The reference target sub-sequence and the variant target sub-sequence can be aligned with respect to nucleotide positions and can differ by the at least one variant nucleotide.

The reference target sub-sequence and the variant target sub-sequence can each have at least 40 nucleotides and can each be flanked by at least 40 nucleotides on each side.

The reference target sub-sequence and the variant target sub-sequence can each have at least 101 nucleotides and can each be flanked by at least 1000 nucleotides on each side.

The variant target sub-sequence can include two variants.

Other implementations may include a non-transitory computer readable storage medium storing instructions executable by a processor to perform the method described above. Yet another implementation may include a system including memory and one or more processors operable to execute instructions, stored in the memory, to perform the method described above.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

Deep learning is a relatively new technique in biology, and is not without potential trade-offs. By learning to automatically extract features from sequence, deep learning models can utilize novel sequence determinants not well-described by human experts, but there is also the risk that the model may incorporate features that do not reflect the true behavior of the spliceosome. I. Deep learning for splice prediction SpliceNet Architecture We trained several ultra-deep convolutional neural network-based models to computationally predict splicing from pre-mRNA nucleotide sequence. We designed four architectures, namely, SpliceNet-80nt, SpliceNet-400nt, SpliceNet-2 k and SpliceNet-10 k, which use 40, 200, 1,000 and 5,000 nucleotides on each side of a position of interest as input respectively, and output the probability of the position being a splice acceptor and donor. More precisely, the input to the models is a sequence of one-hot encoded nucleotides, where A, C, G and T (or equivalently U) are encoded as [1, 0, 0, 0], [0, 1, 0, 0], [0, 0, 1, 0] and [0, 0, 0, 1] respectively and the output of the models consists of three scores which sum to one, corresponding to the probability of the position of interest being a splice acceptor, splice donor and neither.

The basic unit of the SpliceNet architectures is a residual block (He et al., 2016b), which consists of batch-normalization layers (Ioffe and Szegedy, 2015), rectified linear units (ReLU), and convolutional units organized in a specific manner (FIGS. 21, 22, 23, and 24). Residual blocks are commonly used when designing deep neural networks. Prior to the development of residual blocks, deep neural networks consisting of many convolutional units stacked one after the other were very difficult to train due to the problem of exploding/vanishing gradients (Glorot and Bengio, 2010), and increasing the depth of such neural networks often resulted in a higher training error (He et al., 2016a). Through a comprehensive set of computational experiments, architectures consisting of many residual blocks stacked one after the other were shown to overcome these issues (He et al., 2016a).

The complete SpliceNet architectures are provided in FIGS. 21, 22, 23, and 24. The architectures consist of K stacked residual blocks connecting the input layer to the penultimate layer, and a convolutional unit with softmax activation connecting the penultimate layer to the output layer. The residual blocks are stacked such that the output of the $i^{th}$ residual block is connected to the input of the $i+1^{th}$ residual block. Further, the output of every fourth residual block is added to the input of the penultimate layer. Such "skip connections" are commonly used in deep neural networks to increase convergence speed during training (Oord et al., 2016).

Each residual block has three hyper-parameters N, W and D, where N denotes the number of convolutional kernels, W denotes the window size and D denotes the dilation rate (Yu and Koltun, 2016) of each convolutional kernel. Since a convolutional kernel of window size W and dilation rate D extracts features spanning (W−1)D neighboring positions, a residual block with hyper-parameters N, W and D extracts features spanning 2(W−1)D neighboring positions. Hence, the total neighbor span of the SpliceNet architectures is given by $S=\Sigma_{i=1}^{K} 2(W_i-1)D_i$, where $N_i$, $W_i$ and $D_i$ are the hyper-parameters of the $i^{th}$ residual block. For SpliceNet-80nt, SpliceNet-400nt, SpliceNet-2 k and SpliceNet-10 k architectures, the number of residual blocks and the hyper-parameters for each residual block were chosen so that S is equal to 80, 400, 2,000 and 10,000 respectively.

The SpliceNet architectures only have normalization and non-linear activation units in addition to convolutional units. Consequently, the models can be used in a sequence-to-sequence mode with variable sequence length (Oord et al., 2016). For example, the input to the SpliceNet-10 k model (S=10,000) is a one-hot encoded nucleotide sequence of length S/2+1+S/2, and the output is an l×3 matrix, corresponding to the three scores of the l central positions in the input, i.e., the positions remaining after excluding the first and last S/2 nucleotides. This feature can be leveraged to obtain a tremendous amount of computational saving during training as well as testing. This is due to the fact that most of the computations for positions which are close to each other are common, and the shared computations need to be done only once by the models when they are used in a sequence-to-sequence mode.

Our models adopted the architecture of residual blocks, which has become widely adopted due to its success in image classification. The residual blocks comprise repeating units of convolution, interspersed with skip connections that allow information from earlier layers to skip over residual blocks. In each residual block, the input layer is first batch normalized, followed by an activation layer using rectified linear units (ReLU). The activation is then passed through a 1D convolution layer. This intermediate output from the 1D convolution layer is again batch normalized and ReLU activated, followed by another 1D convolution layer. At the end of the second 1D convolution, we summed its output with the original input into the residual block, which acts as a skip connection by allowing the original input information to bypass the residual block. In such an architecture, termed a deep residual learning network by its authors, the input is preserved in its original state and the residual connections are kept free of nonlinear activations from the model, allowing effective training of deeper networks.

Following the residual blocks, the softmax layer computes probabilities of the three states for each amino acid, among which the largest softmax probability determines the state of the amino acid. The model is trained with accumulated categorical cross entropy loss function for the whole protein sequence using the ADAM optimizer.

Atrous/dilated convolutions allow for large receptive fields with few trainable parameters. An atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed.

The illustrated example uses 1D convolutions. In other implementations, the model can use different types of convolutions such as 2D convolutions, 3D convolutions, dilated or atrous convolutions, transposed convolutions, separable convolutions, and depthwise separable convolutions. Some layers also use ReLU activation function which greatly accelerates the convergence of stochastic gradient descent compared to saturating nonlinearities such as sigmoid or hyperbolic tangent. Other examples of activation functions that can be used by the technology disclosed include parametric ReLU, leaky ReLU, and exponential linear unit (ELU).

Some layers also use batch normalization (Ioffe and Szegedy 2015). Regarding batch normalization, distribution of each layer in a convolution neural network (CNN) changes during training and it varies from one layer to another. This reduces the convergence speed of the optimization algorithm. Batch normalization is a technique to overcome this problem. Denoting the input of a batch normalization layer with x and its output using z, batch normalization applies the following transformation on x:

$$z = \frac{x-\mu}{\sqrt{\sigma^2+\varepsilon}} \gamma + \beta$$

Batch normalization applies mean-variance normalization on the input x using t and c and linearly scales and shifts it using γ and β. The normalization parameters μ and σ are computed for the current layer over the training set using a method called exponential moving average. In other words, they are not trainable parameters. In contrast, γ and β are trainable parameters. The values for μ and σ calculated during training are used in forward pass during inference.

Computer System

Figure 37:
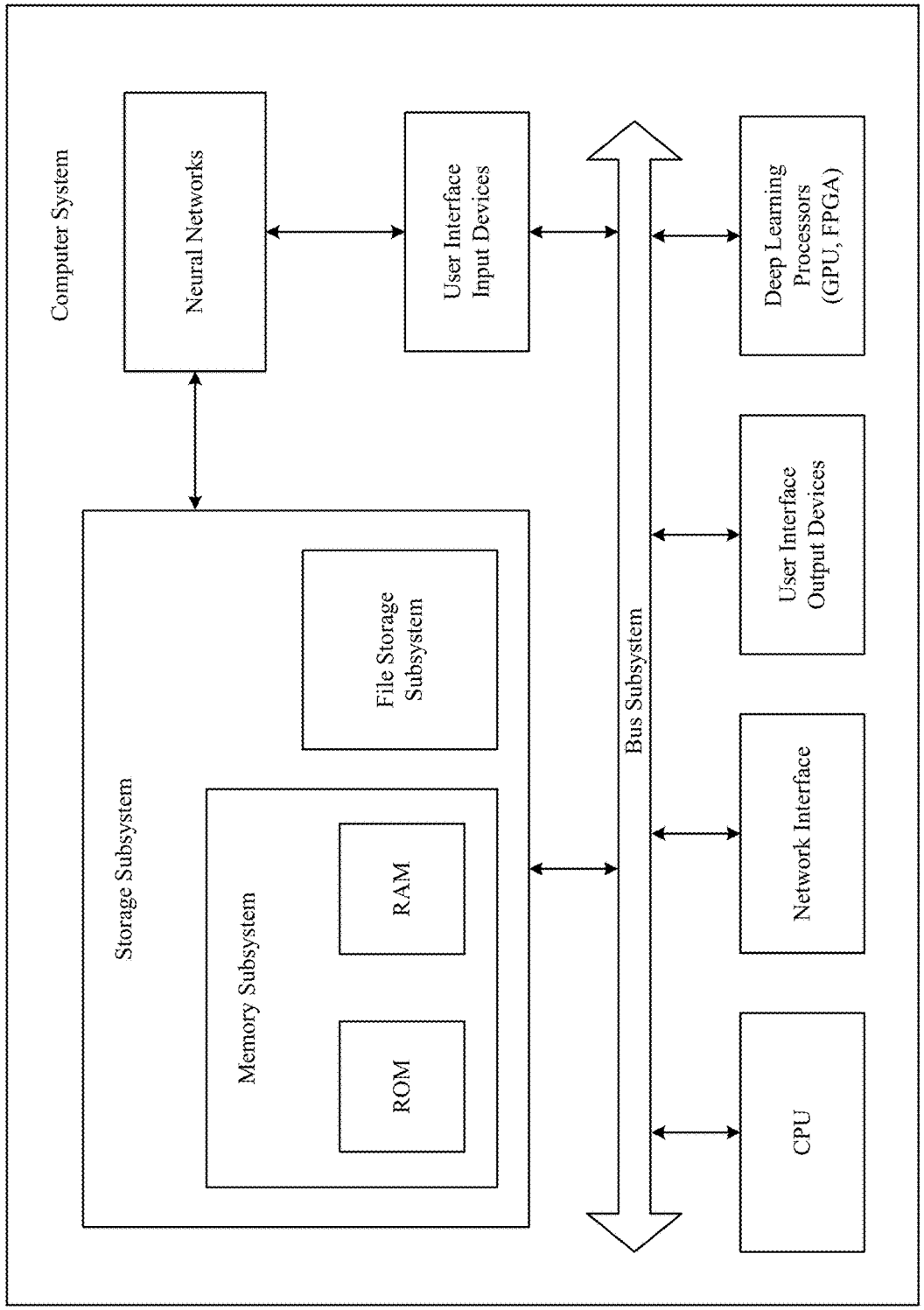
FIG. 37 is a simplified block diagram of a computer system that can be used to implement the technology disclosed.

FIG. 37 is a simplified block diagram of a computer system that can be used to implement the technology disclosed. Computer system typically includes at least one processor that communicates with a number of peripheral devices via bus subsystem. These peripheral devices can include a storage subsystem including, for example, memory devices and a file storage subsystem, user interface input devices, user interface output devices, and a network interface subsystem. The input and output devices allow user interaction with computer system. Network interface subsystem provides an interface to outside networks, including an interface to corresponding interface devices in other computer systems.

In one implementation, the neural networks such as ACNN and CNN are communicably linked to the storage subsystem and user interface input devices.

User interface input devices can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem stores programming and data constructs that provide the functionality of some or all of the modules and methods described herein. These software modules are generally executed by processor alone or in combination with other processors.

Memory used in the storage subsystem can include a number of memories including a main random access memory (RAM) for storage of instructions and data during program execution and a read only memory (ROM) in which fixed instructions are stored. A file storage subsystem can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 37 is intended only as a specific example for purposes of illustrating the technology disclosed. Many other configurations of computer system are possible having more or less components than the computer system depicted in FIG. 37.

The deep learning processors can be GPUs or FPGAs and can be hosted by a deep learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

What is claimed is:

1. A neural network-implemented method of training a convolutional neural network, the method including:
    training a convolutional neural network on at least 50000 training examples of donor sites, at least 50000 training examples of acceptor sites, and at least 100000 training examples of non-occurrence sites using a backpropagation-based gradient update technique that progressively matches outputs of the convolutional neural network with corresponding ground truth labels;
    wherein each training example is a target base sequence having at least one target base flanked by at least 20 bases on each side;
    for evaluating a training example using the convolutional neural network, providing, as input to the convolutional neural network, a target base sequence further flanked by at least 40 upstream context bases and at least 40 downstream context bases; and
    based on the evaluation, the convolutional neural network producing, as output, triplet scores for likelihood that each base in the target base sequence is a donor site, an acceptor site, or a non-occurrence site.

2. The neural network-implemented method of claim 1, wherein the convolutional neural network is parameterized by a number of convolution layers, a number of convolution filters, and a number of subsampling layers.

3. The neural network-implemented method of claim 1, wherein the convolutional neural network includes one or more fully-connected layers and a terminal classification layer.

4. The neural network-implemented method of claim 1, wherein the convolutional neural network comprises dimensionality altering layers that reshape spatial and feature dimensions of a preceding input.

5. The neural network-implemented method of claim 1, wherein the convolutional neural network is parameterized by a number of residual blocks, a number of skip connections, and a number of residual connections.

6. The neural network-implemented method of claim 1, wherein each residual block comprises at least one batch normalization layer, at least one rectified linear unit (abbreviated ReLU) layer, at least one dimensionality altering layer, and at least one residual connection.

7. The neural network-implemented method of claim 6, wherein each residual block comprises two batch normalization layers, two ReLU non-linearity layers, two dimensionality altering layers, and one residual connection.

8. The neural network-implemented method of claim 1, wherein the convolutional neural network batch-wise evaluates the training examples during an epoch.

9. The neural network-implemented method of claim 8, wherein the training examples are randomly sampled into batches, wherein each batch has a predetermined batch size.

10. The neural network-implemented method of claim 9, wherein the convolutional neural network iterates evaluation of the training examples over 10 epochs.

11. The neural network-implemented method of claim 1, further including one-hot encoding the training examples and providing one-hot encodings as input.

12. A system including one or more processors coupled to memory, the memory loaded with computer instructions to train a convolutional neural network, the instructions, when executed on the processors, implement actions comprising:
training a convolutional neural network on at least 50000 training examples of donor sites, at least 50000 training examples of acceptor sites, and at least 100000 training examples of non-occurrence sites using a backpropagation-based gradient update technique that progressively matches outputs of the convolutional neural network with corresponding ground truth labels;
wherein each training example is a target base sequence having at least one target base flanked by at least 20 bases on each side;
for evaluating a training example using the convolutional neural network, providing, as input to the convolutional neural network, a target base sequence further flanked by at least 40 upstream context bases and at least 40 downstream context bases; and
based on the evaluation, the convolutional neural network producing, as output, triplet scores for likelihood that each base in the target base sequence is a donor site, an acceptor site, or a non-occurrence site.

13. The system of claim 12, wherein the convolutional neural network is parameterized by a number of convolution layers, a number of convolution filters, and a number of subsampling layers.

14. The system of claim 12, wherein the convolutional neural network includes one or more fully-connected layers and a terminal classification layer.

15. The system of claim 12, wherein the convolutional neural network batch-wise evaluates the training examples during an epoch.

16. The system of claim 15, wherein the training examples are randomly sampled into batches, wherein each batch has a predetermined batch size.

17. The system of claim 16, wherein the convolutional neural network iterates evaluation of the training examples over 10 epochs.

18. A non-transitory computer readable storage medium impressed with computer program instructions to train a convolutional neural network, the instructions, when executed on a processor, implement a method comprising:
training a convolutional neural network on at least 50000 training examples of donor sites, at least 50000 training examples of acceptor sites, and at least 100000 training examples of non-occurrence sites using a backpropagation-based gradient update technique that progressively matches outputs of the convolutional neural network with corresponding ground truth labels;
wherein each training example is a target base sequence having at least one target base flanked by at least 20 bases on each side;
for evaluating a training example using the convolutional neural network, providing, as input to the convolutional neural network, a target base sequence further flanked by at least 40 upstream context bases and at least 40 downstream context bases; and
based on the evaluation, the convolutional neural network producing, as output, triplet scores for likelihood that each base in the target base sequence is a donor site, an acceptor site, or a non-occurrence site.

19. The non-transitory computer readable storage medium of claim 18, wherein the convolutional neural network is parameterized by a number of convolution layers, a number of convolution filters, and a number of subsampling layers.

20. The non-transitory computer readable storage medium of claim 18, wherein the convolutional neural network includes one or more fully-connected layers and a terminal classification layer.

* * * * *

UNITED STATES PATENT AND TRADEMARK OFFICE
CERTIFICATE OF CORRECTION

PATENT NO. : 11,397,889 B2
APPLICATION NO. : 16/160984
DATED : July 26, 2022
INVENTOR(S) : Kishore Jaganathan et al.

It is certified that error appears in the above-identified patent and that said Letters Patent is hereby corrected as shown below:

On the Title Page

Item (57), Column 2, Lines 6-7 of the Abstract: Delete "network network-based" and insert -- neural network-based --.

Signed and Sealed this
Fifteenth Day of November, 2022

Katherine Kelly Vidal
*Director of the United States Patent and Trademark Office*